US010076515B2

(12) United States Patent
Ostrow et al.

(10) Patent No.: US 10,076,515 B2
(45) Date of Patent: *Sep. 18, 2018

(54) OPHTHALMIC COMPOSITION

(71) Applicant: Sydnexis, Inc., Del Mar, CA (US)

(72) Inventors: Gregory I. Ostrow, San Diego, CA (US); Kenneth J. Widder, Rancho Santa Fe, CA (US); David S. Baker, Carlsbad, CA (US)

(73) Assignee: SYDNEXIS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/661,816

(22) Filed: Jul. 27, 2017

(65) Prior Publication Data

US 2018/0042911 A1    Feb. 15, 2018

Related U.S. Application Data

(63) Continuation of application No. 15/208,537, filed on Jul. 12, 2016, now Pat. No. 9,770,447, which is a continuation of application No. 14/726,139, filed on May 29, 2015, now Pat. No. 9,421,199.

(60) Provisional application No. 62/151,926, filed on Apr. 23, 2015, provisional application No. 62/096,433, filed on Dec. 23, 2014, provisional application No. 62/016,502, filed on Jun. 24, 2014.

(51) Int. Cl.
*A61K 31/46* (2006.01)
*A61K 9/00* (2006.01)
*A61K 47/02* (2006.01)

(52) U.S. Cl.
CPC ............ *A61K 31/46* (2013.01); *A61K 9/0048* (2013.01); *A61K 47/02* (2013.01)

(58) Field of Classification Search
CPC ........... A61K 31/46; A61K 47/02; A61K 9/00
See application file for complete search history.

(56) References Cited

U.S. PATENT DOCUMENTS

| | | | |
|---|---|---|---|
| 3,863,633 A | 2/1975 | Ryde et al. | |
| 4,014,335 A | 3/1977 | Arnold | |
| 4,474,751 A | 10/1984 | Haslam et al. | |
| 4,938,763 A | 7/1990 | Dunn et al. | |
| 5,033,252 A | 7/1991 | Carter | |
| 5,052,558 A | 10/1991 | Carter | |
| 5,147,647 A | 9/1992 | Darougar | |
| 5,259,998 A | 11/1993 | Reich et al. | |
| 5,260,000 A | 11/1993 | Nandu et al. | |
| 5,323,907 A | 6/1994 | Kalvelage | |
| 5,324,519 A | 6/1994 | Dunn et al. | |
| 5,702,716 A | 12/1997 | Dunn et al. | |
| 5,716,952 A | 2/1998 | Woldemussie et al. | |
| 5,744,153 A | 4/1998 | Yewey et al. | |
| 5,858,375 A | 1/1999 | Furminger et al. | |
| 5,900,360 A | 5/1999 | Welch et al. | |
| 5,990,194 A | 11/1999 | Dunn et al. | |
| 6,139,870 A | 10/2000 | Verrecchia | |
| 6,218,428 B1 | 4/2001 | Chynn | |
| 6,270,954 B1 | 8/2001 | Welch et al. | |
| 6,410,048 B1 | 6/2002 | Fotinos | |
| 6,503,497 B2 | 1/2003 | Chowhan et al. | |
| 6,720,001 B2 | 4/2004 | Chen et al. | |
| 7,691,099 B2 | 4/2010 | Berry | |
| 7,858,582 B2 | 12/2010 | Jin et al. | |
| 8,333,985 B2 | 12/2012 | Knaack et al. | |
| 8,980,839 B2 | 3/2015 | Mitra et al. | |
| 9,421,199 B2 | 8/2016 | Ostrow et al. | |
| 2003/0157187 A1 | 8/2003 | Hunter | |
| 2005/0249770 A1 | 11/2005 | Hunter | |
| 2006/0159771 A1 | 7/2006 | Kadrmas et al. | |
| 2007/0207192 A1 | 9/2007 | Holl et al. | |
| 2007/0280992 A1 | 12/2007 | Margaron et al. | |
| 2008/0113035 A1 | 5/2008 | Hunter | |
| 2008/0153900 A1 | 6/2008 | Hunter | |
| 2010/0022495 A1 | 1/2010 | Hotamisligil et al. | |
| 2010/0196285 A1 | 8/2010 | Bayerl | |

(Continued)

FOREIGN PATENT DOCUMENTS

| CN | 1456161 A | 11/2003 |
|---|---|---|
| CN | 101327216 A | 12/2008 |

(Continued)

OTHER PUBLICATIONS

Abraham et al. Draize rabbit eye test compatibility with eye irritation thresholds in humans: a quantitative structure-activity relationship analysis. Toxicol Sci 76:384-391 (2003).
Badaro et al. Retinal biocompatibility of brilliant Blue G with deuterated water for chromovitrectomy. J. Ophthalmic and Vision Research 9(2): 204-209 (2014).
Cheng et al. Water movement in the rabbit eye. Exp. Eye Res. 52:337-339 (1991).
Cheng. Fate of water in the soft contact lens immediately after lens placement onto the cornea. Optometry and Vision Science 68(6):414-417 (1991).

(Continued)

*Primary Examiner* — Zohreh A Fay
(74) *Attorney, Agent, or Firm* — Wilson, Sonsini, Goodrich & Rosati

(57) ABSTRACT

Provided herein is an ophthalmic composition. In some embodiments, the ophthalmic composition includes a low concentration of an ophthalmic agent for treatment of an ophthalmic disorder or condition; and an ophthalmically acceptable carrier, wherein the ophthalmic agent is distributed with substantial uniformity throughout the ophthalmically acceptable carrier. Further disclosed herein include an ophthalmic composition including a low concentration of an ophthalmic agent and deuterated water. Also disclosed herein are methods of arresting or preventing myopia development by administering to an eye of an individual in need thereof an effective amount of an ophthalmic composition as described herein.

20 Claims, 10 Drawing Sheets

(56) References Cited

U.S. PATENT DOCUMENTS

| | | |
|---|---|---|
| 2010/0256557 A1 | 10/2010 | Lust et al. |
| 2012/0015035 A1 | 1/2012 | Wildsoet et al. |
| 2012/0028910 A1 | 2/2012 | Combal et al. |
| 2012/0135084 A1 | 5/2012 | Bayerl |
| 2012/0203161 A1 | 8/2012 | Herekar |
| 2012/0277694 A1 | 11/2012 | Odrich et al. |
| 2013/0302855 A1 | 11/2013 | Selber et al. |
| 2014/0011761 A1 | 1/2014 | Hotamisligil et al. |
| 2014/0088199 A1 | 3/2014 | Sharma |
| 2014/0350049 A1 | 11/2014 | Hovnanian et al. |
| 2015/0290125 A1 | 10/2015 | Horn et al. |
| 2016/0009705 A1 | 1/2016 | Ostrow et al. |
| 2016/0339007 A1 | 11/2016 | Ostrow et al. |

FOREIGN PATENT DOCUMENTS

| | | |
|---|---|---|
| CN | 101468214 A | 7/2009 |
| DE | 1182388 B | 11/1964 |
| DE | 1518819 B1 | 12/1969 |
| EP | 0332826 A1 | 9/1989 |
| WO | WO-9421298 A1 | 9/1994 |
| WO | WO-9624331 A1 | 8/1996 |
| WO | WO-9716192 A1 | 5/1997 |
| WO | WO-0049990 A2 | 8/2000 |
| WO | WO-02096418 A1 | 12/2002 |
| WO | WO-2008005053 A1 | 1/2008 |
| WO | WO-2008008330 A2 | 1/2008 |
| WO | WO-2010083129 A1 | 7/2010 |
| WO | WO-2011019940 A2 | 2/2011 |
| WO | WO-2011098578 A2 | 8/2011 |
| WO | WO-2011137449 A2 | 11/2011 |
| WO | WO-2012111029 A2 | 8/2012 |
| WO | WO-2012161655 A1 | 11/2012 |
| WO | WO-2013166385 A1 | 11/2013 |
| WO | WO-2014140105 A1 | 9/2014 |
| WO | WO-2015200361 A1 | 12/2015 |
| WO | WO-2016172712 A2 | 10/2016 |
| WO | WO-2016196367 A1 | 12/2016 |

OTHER PUBLICATIONS

Chirieri et al. Investigations concerning the changes induced by deuterium for hydrogen substitution in bioelectric activity of the frog retina. Physiologie 14(2):119-123 (1977).

Criado et al. Scavenging of photogenerated oxidative species by antimuscarinic drugs: atropine and derivatives. Redoc Rep 7(6):385-394 (2002).

Ganea. Heavy water effect on certain energetic processes in retina. Physiologie 6(1):59-62 (1979).

Gettings et al. A comparison of low volume, Draize and in vitro eye irritation test data. III. Surfactant-based formulations. Food Chem Toxicol 36(3):209-231 (1998).

Glasoe et al. Use of glass electrodes to measure acidities in deuterium oxide. Journal of Physical Chemistry.64:188-190 (1960).

Guidance for Industry: Q1A (R2) Stability Testing of New Drug Substances and Products. U.S. Department of Health and Human Services, Food and Drug Administration. Retrieved from the internet http://fda.gov/downloads/drugs/guidancecomplianceregulatoryinformation/guideances/ucm073369.pdf (25 pgs.) (Nov. 2013/retrieved Jul. 27, 2016).

Januschowski et al. Evaluating retinal toxicity of a new heavy intraocular dye, using a model of perfused and isolated retinal cultures of bovine and human origins. Graefes Arch Clin Exp Ophthalmol. 250:1013-1022 (2012).

Jeong et al. Biodegradable block copolymers as injectable drug-delivery systems. Nature 388(6645):860-862 (1997).

Jeong et al. Drug release from biodegradable injectable thermosensitive hydrogel of PEG-PLGA-PEG triblock copolymers. J Control Release 63(1-2):155-163 (2000).

Jeong et al. Thermosensitive sol-gel reversible hydrogels. Advanced Drug Delivery Reviews 54:37-51 (2002).

Krezel et al. A formula for correlating pKa values determined in D2O and H2O. Journal of Inorganic Chemistry 98:161-166 (2008).

Lai et al. Rapid transport of large polymeric nanoparticles in fresh undiluted human mucus. PNAS USA 104(5):1482-1487 (2007).

Lund et al. The Kinetics of atropine and apoatropine in aqueous solutions. ACTA Chemica Scandinavica 22:3085-3097 (1968).

McCall et al. Mechanisms of corneal tissue cross-linking in response to treatment with topical riboflavin and long-wavelength ultraviolet radiation (UVA). Investigative Ophthalmology & Visual Science 51(1):129-138 (2010).

Obata et al. Deuterium magnetic resonance imaging of rabbit eye in Vivo. Magnetic Resonance in Medicine.33(4):569-572 (1995).

Obata et al. Deuterium MR in vivo imaging of the rat eye using 2H2O. Acta Radiologica,36:552-555 (1995).

PCT/US2015/037249 International Search Report and Written Opinion dated Sep. 30, 2015.

PCT/US2016/029222 International Search Report and Written Opinion dated Oct. 21, 2016.

PCT/US2016/34823 International Search Report and Written Opinion dated Aug. 23, 2016.

Richard et al. Effects of sterilizing-grade filters on the physico-chemical properties of onion-like vesicles. Int J Pharm 312(1-2):144-150 (2006).

Siegel et al. Stability of procaine in deuterium oxide. J Pharm Sci 53:978-979 (1964).

Taktak et al. Assay of Pyrogens by Interleukin-6 Release from Monocytic Cell Lines. J. Pharm. Pharmacol. 43:578-582 (1991).

The U. S. Food and Drug Administration has provided regulatory guidance in the publication: Guidance for Industry: Sterile Drug Products Produced by Aseptic Processing. available at: http://www.fda.gov/cder/guidance/5882fn1.htm (Aug. 2003) (63 pgs.).

U.S. Appl. No. 14/859,042 Office Action dated May 18, 2017.

U.S. Appl. No. 14/859,042 Office Action dated Oct. 25, 2016.

U.S. Appl. No. 15/208,537 Office Action dated Jan. 25, 2017.

U.S. Appl. No. 15/208,537 Office Action dated Sep. 30, 2016.

Viegas et al. Osmotic behavior of poloxamer 407 and other non-ionic surfactants in aqueous solutions. Int J Pharm 160:157-162 (1998).

PCT/US2016/034823 International Preliminary Report on Patentability dated Dec. 14, 2017.

Chasin et al. Polyanhdrides for Controlled Drug Delivery. Biopharm pp. 33-46 (1988).

Douglas et al. Nanoparticles in Drug Delivery. CRC Crit. Rev. Therap. Drug Carr Syst 3:233-261 (1987).

PCT/US2016/029222 International Preliminary Report on Patentability dated Nov. 2, 2017.

| | Temp (°C) | Weeks | | | | |
|---|---|---|---|---|---|---|
| | | 0 | 1 | 1.571429 | 2.142857 | 3.428571 | 6.571429 |
| T1 | 25 | 0.08 | | | 0.88 | | 2.81 |
| T2 | 40 | 0.08 | | 3.47 | | 4.48 | |

| Formulation: | Average of Analysis | | | |
|---|---|---|---|---|
| Stability Prediction: | RRT 0.87 | | | |
| | spec limit: | 0.50 | % (not more than) | |
| | | | shelf life | |
| | | | weeks | months |
| rate | 1.24844 | at 40C | 0.4 | 0.1 |
| rate | 0.60617 | at 30C | 0.8 | 0.2 |
| rate | 0.41477 | at 25C | 1.2 | 0.3 |
| rate | 0.07932 | at 2-8C | 6.3 | 1.6 |
| rate | 0.00694 | at -20C | N/A | N/A |

| | Temp (°C) | Weeks | | | | |
|---|---|---|---|---|---|---|
| | | 0 | 1 | 2.142857 | 4 | 6.571429 |
| T1 | 25 | 0.08 | | 0.9 | | 2.8 |
| T2 | 60 | 0.08 | 10.5 | | 11.3 | |

| Formulation: | Average of Analysts | | | |
|---|---|---|---|---|
| Stability Prediction: | RRT 0.87 | | | |
| | spec limit: | 0.50 | % (not more than) | |
| | | | shelf life | |
| | | | weeks | months |
| rate | 0.88876 | at 40C | 0.6 | 0.1 |
| rate | 0.54051 | at 30C | 0.9 | 0.2 |
| rate | 0.41627 | at 25C | 1.2 | 0.3 |
| rate | 0.13331 | at 2-8C | 3.8 | 0.9 |
| rate | 0.02493 | at -20C | N/A | N/A |

OPHTHALMIC COMPOSITION

CROSS-REFERENCE TO RELATED APPLICATIONS

This application is a continuation of U.S. application Ser. No. 15/208,537, filed Jul. 12, 2016, which is a continuation of U.S. application Ser. No. 14/726,139, filed May 29, 2015, now U.S. Pat. No. 9,421,199, issued Aug. 23, 2016, which claims the benefit of U.S. Provisional Application Ser. No. 62/151,926, filed Apr. 23, 2015, U.S. Provisional Application Ser. No. 62/096,433, filed Dec. 23, 2014, and U.S. Provisional Application Ser. No. 62/016,502, filed Jun. 24, 2014, each of which are incorporated herein in their entirety.

BACKGROUND OF THE DISCLOSURE

Pharmaceutical formulations have an expiration date which is based on the degradation of the active ingredient.

SUMMARY OF THE DISCLOSURE

Provided herein are ophthalmic compositions. In some embodiments, disclosed herein is an ophthalmic composition, comprising from about 0.001 wt % to about 0.05 wt % of a muscarinic antagonist and deuterated water, at a pD of from about 4.2 to about 7.9.

In some embodiments, the muscarinic antagonist comprises atropine, atropine sulfate, noratropine, atropine-N-oxide, tropine, tropic acid, hyoscine, scopolomine, tropicamide, cyclopentolate, pirenzapine, homatropine, or a combination thereof. In some embodiments, the muscarinic antagonist is atropine, or atropine sulfate.

In some embodiments, the ophthalmic composition has a pD of one of: less than about 7.3, less than about 7.2, less than about 7.1, less than about 7, less than about 6.8, less than about 6.5, less than about 6.4, less than about 6.3, less than about 6.2, less than about 6.1, less than about 6, less than about 5.9, less than about 5.8, less than about 5.2, or less than about 4.8 after extended period of time under storage condition.

In some embodiments, the ophthalmic composition comprises one of: at least about 80%, at least about 85%, at least about 90%, at least about 93%, at least about 95%, at least about 97%, at least about 98%, or at least about 99% of the muscarinic antagonist based on initial concentration after extended period of time under storage condition. As described in this disclosure, the percentage of the ophthalmic agent in the composition after storage is based on the amount of ophthalmic agent that is initially present in the composition (i.e. prior to the storage condition).

In some embodiments, the ophthalmic composition further has a potency of one of: at least 80%, at least 85%, at least 90%, at least 93%, at least 95%, at least 97%, at least 98%, or at least 99% after extended period of time under storage condition. As described in this disclosure, the potency of the ophthalmic agent in the composition after storage is based on the potency of ophthalmic agent that is initially present in the composition (i.e. prior to the storage condition).

In some embodiments, the extended period of time is one of: about 1 week, about 2 weeks, about 3 weeks, about 1 month, about 2 months, about 3 months, about 4 months, about 5 months, about 6 months, about 8 months, about 10 months, about 12 months, about 18 months, about 24 months, about 36 months, about 4 years, or about 5 years.

In some embodiments, the storage condition has a storage temperature of from about 2° C. to about 10° C. or from about 16° C. to about 26° C. In some embodiments, the storage condition has a storage temperature of about 25° C. In some embodiments, the storage condition has a storage temperature of about 40° C. In some embodiments, the storage condition has a storage temperature of about 60° C.

In some embodiments, the storage condition has a relative humidity of about 60%. In some embodiments, the storage condition has a relative humidity of about 75%.

In some embodiments, the muscarinic antagonist is present in the composition at a concentration of one of: from about 0.001 wt % to about 0.04 wt %, from about 0.001 wt % to about 0.03 wt %, from about 0.001 wt % to about 0.025 wt %, from about 0.001 wt % to about 0.02 wt %, from about 0.001 wt % to about 0.01 wt %, from about 0.001 wt % to about 0.008 wt %, or from about 0.001 wt % to about 0.005 wt %.

In some embodiments, the composition comprises less than 20% of major degradant based on the concentration of the ophthalmic agent after extended period of time under storage condition. In some embodiments, the composition comprises less than 15% of major degradant based on the concentration of the ophthalmic agent after extended period of time under storage condition.

In some embodiments, the composition comprises less than 10% of major degradant based on the concentration of the ophthalmic agent after extended period of time under storage condition. In some embodiments, the composition comprises less than 5% of major degradant based on the concentration of the ophthalmic agent after extended period of time under storage condition. In some embodiments, the composition comprises less than 2.5% of major degradant based on the concentration of the ophthalmic agent after extended period of time under storage condition. In some embodiments, the composition comprises less than 2.0% of major degradant based on the concentration of the ophthalmic agent after extended period of time under storage condition. In some embodiments, the composition comprises less than 1.5% of major degradant based on the concentration of the ophthalmic agent after extended period of time under storage condition. In some embodiments, the composition comprises less than 1.0% of major degradant based on the concentration of the ophthalmic agent after extended period of time under storage condition. In some embodiments, the composition comprises less than 0.5% of major degradant based on the concentration of the ophthalmic agent after extended period of time under storage condition. In some embodiments, the composition comprises less than 0.4% of major degradant based on the concentration of the ophthalmic agent after extended period of time under storage condition. In some embodiments, the composition comprises less than 0.3% of major degradant based on the concentration of the ophthalmic agent after extended period of time under storage condition. In some embodiments, the composition comprises less than 0.2% of major degradant based on the concentration of the ophthalmic agent after extended period of time under storage condition. In some embodiments, the composition comprises less than 0.1% of major degradant based on the concentration of the ophthalmic agent after extended period of time under storage condition. In some embodiments, the major degradant is tropic acid. As described in this disclosure, the percentage of the primary degradant in the composition after storage is based on the amount of ophthalmic agent that is initially present in the composition (i.e. prior to the storage condition).

In some embodiments, the composition is in a form of an aqueous solution.

In some embodiments, the composition further comprises an osmolarity adjusting agent. In some embodiments, the osmolarity adjusting agent is sodium chloride.

In some embodiments, the ophthalmic composition further comprises a preservative. In some embodiments, the preservative is selected from benzalkonium chloride, cetrimonium, sodium perborate, stabilized oxychloro complex, SofZia, polyquaternium-1, chlorobutanol, edetate disodium, polyhexamethylene biguanide, or combinations thereof.

In some embodiments, the ophthalmic composition further comprises a buffer agent. In some embodiments, the buffer agent is selected from borates, borate-polyol complexes, phosphate buffering agents, citrate buffering agents, acetate buffering agents, carbonate buffering agents, organic buffering agents, amino acid buffering agents, or combinations thereof.

In some embodiments, the ophthalmic composition further comprises a tonicity adjusting agent. In some embodiments, the tonicity adjusting agent is selected from sodium chloride, sodium nitrate, sodium sulfate, sodium bisulfate, potassium chloride, calcium chloride, magnesium chloride, zinc chloride, potassium acetate, sodium acetate, sodium bicarbonate, sodium carbonate, sodium thiosulfate, magnesium sulfate, disodium hydrogen phosphate, sodium dihydrogen phosphate, potassium dihydrogen phosphate, dextrose, mannitol, sorbitol, dextrose, sucrose, urea, propylene glycol, glycerin, or a combination thereof.

In some embodiments, the composition is stored in a plastic container. In some embodiments, the material of the plastic container comprises low-density polyethylene (LDPE).

In some embodiments, the ophthalmic composition is essentially free of procaine and benactyzine, or pharmaceutically acceptable salts thereof.

In some embodiments, the composition has a dose-to-dose ophthalmic agent concentration variation of less than 50%. In some embodiments, the composition has a dose-to-dose ophthalmic agent concentration variation of less than 40%. In some embodiments, the composition has a dose-to-dose ophthalmic agent concentration variation of less than 30%. In some embodiments, the composition has a dose-to-dose ophthalmic agent concentration variation of less than 20%. In some embodiments, the composition has a dose-to-dose ophthalmic agent concentration variation of less than 10%. In some embodiments, the composition has a dose-to-dose ophthalmic agent concentration variation of less than 5%. In some embodiments, the dose-to-dose ophthalmic agent concentration variation is based on 10 consecutive doses. In some embodiments, the dose-to-dose ophthalmic agent concentration variation is based on 8 consecutive doses. In some embodiments, the dose-to-dose ophthalmic agent concentration variation is based on 5 consecutive doses. In some embodiments, the dose-to-dose ophthalmic agent concentration variation is based on 3 consecutive doses. In some embodiments, the dose-to-dose ophthalmic agent concentration variation is based on 2 consecutive doses.

In some embodiments, the composition further comprises a pD adjusting agent. In some embodiments, the pD adjusting agent comprises DCl, NaOD, $CD_3COOD$, or $C_6D_8O_7$.

In some embodiments, the ophthalmically acceptable carrier further comprises at least one viscosity-enhancing agent. In some embodiments, the viscosity-enhancing agent is selected from cellulose-based polymers, polyoxyethylene-polyoxypropylene triblock copolymers, dextran-based polymers, polyvinyl alcohol, dextrin, polyvinylpyrrolidone, polyalkylene glycols, chitosan, collagen, gelatin, hyaluronic acid, or combinations thereof.

In some embodiments, the ophthalmic composition comprises one of: less than 60% of $H_2O$, less than 55% of $H_2O$, less than 50% of $H_2O$, less than 45% of $H_2O$, less than 40% of $H_2O$, less than 35% of $H_2O$, less than 30% of $H_2O$, less than 25% of $H_2O$, less than 20% of $H_2O$, less than 15% of $H_2O$, or less than 10% of $H_2O$.

In some embodiments, the ophthalmic composition comprises one of: less than 5% of $H_2O$, less than 4% of $H_2O$, less than 3% of $H_2O$, less than 2% of $H_2O$, less than 1% of $H_2O$, less than 0.5% of $H_2O$, less than 0.1% of $H_2O$, or 0% of $H_2O$.

In some embodiments, the ophthalmic composition is stored below room temperature prior to first use. In some embodiments, the ophthalmic composition is stored at between about 2° C. to about 10° C. prior to first use. In some embodiments, the ophthalmic composition is stored at between about 4° C. to about 8° C. prior to first use.

In some embodiments, the ophthalmic composition is stored at room temperature after first use. In some embodiments, the ophthalmic composition is stored at between about 16° C. to about 26° C. after first use.

In some embodiments, the ophthalmic composition is not formulated as an injectable formulation.

In some embodiments, the ophthalmic composition is formulated as an ophthalmic solution for the treatment of pre-myopia, myopia, or progression of myopia.

In some embodiments, disclosed herein is a method of arresting myopia development that comprises administering to an eye of an individual in need thereof an effective amount of an ophthalmic composition described herein. Also described herein is a method of preventing myopia development that comprises administering to an eye of an individual in need thereof an effective amount of an ophthalmic composition described herein. In some embodiments, described herein is a method of arresting or preventing myopia development, comprising administering to an eye of an individual in need thereof an effective amount of an ophthalmic composition comprising from about 0.001 wt % to about 0.05 wt % of a muscarinic antagonist and deuterated water, at a pD of from about 4.2 to about 7.9. In some embodiments, the ophthalmic composition is administered at predetermined time intervals over an extended period of time. In some embodiments, the ophthalmic composition is administered once every day. In some embodiments, the ophthalmic composition is administered every other day. In some embodiments, the ophthalmic composition is administered over 1 week, 2 weeks, 1 month, 2 months, 3 months, 6 months, 1 year, 2 years, 3 years, 4 years, 5 years, 6 years, 7 years, 8 years, 9 years, 10 years, 11 years, or 12-15 years. In some embodiments, the ophthalmic composition is stored at between about 2° C. to about 10° C. prior to first use. In some embodiments, the ophthalmic composition is stored at between about 16° C. to about 26° C. after first use.

In some embodiments, disclosed herein is an ophthalmic solution that comprises from about 0.001 wt % to about 0.05 wt % of a muscarinic antagonist and deuterated water, at a pD of from about 4.2 to about 7.9. In some embodiments, the ophthalmic solution has a pD of one of: less than about 7.3, less than about 7.2, less than about 7.1, less than about 7, less than about 6.8, less than about 6.5, less than about 6.4, less than about 6.3, less than about 6.2, less than about 6.1, less than about 6, less than about 5.9, less than about 5.8, less than about 5.2, or less than about 4.8 after extended period of time under storage condition. In some embodiments, the muscarinic antagonist comprises atropine, atropine sulfate, noratropine, atropine-N-oxide, tropine, tropic acid, hyoscine, scopolomine, tropicamide, cyclopentolate, pirenzapine, homatropine, or a combination thereof. In some embodiments, the ophthalmic solution comprises one of: less than 5% of $H_2O$, less than 4% of $H_2O$, less than 3% of $H_2O$, less than 2% of $H_2O$, less than 1% of $H_2O$, less than 0.5% of $H_2O$, less than 0.1% of $H_2O$, or 0% of $H_2O$. In some embodiments, the ophthalmic composition comprises one of: at least about 80%, at least about 85%, at least about 90%, at least about 93%, at least about 95%, at least about 97%, at least about 98%, or at least about 99% of the muscarinic antagonist based on initial concentration after extended period of time under storage condition. In some embodiments, the ophthalmic composition further has a potency of one of: at least 80%, at least 85%, at least 90%, at least 93%, at least 95%, at least 97%, at least 98%, or at least 99% after extended period of time under storage condition. In some embodiments, the extended period of time is one of: about 1 week, about 2 weeks, about 3 weeks, about 1 month, about 2 months, about 3 months, about 4 months, about 5 months, about 6 months, about 8 months, about 10 months, about 12 months, about 18 months, about 24 months, about 36 months, about 4 years, or about 5 years. In some embodiments, the muscarinic antagonist is present in the composition at a concentration of one of: from about 0.001 wt % to about 0.04 wt %, from about 0.001 wt % to about 0.03 wt %, from about 0.001 wt % to about 0.025 wt %, from about 0.001 wt % to about 0.02 wt %, from about 0.001 wt % to about 0.01 wt %, from about 0.001 wt % to about 0.008 wt %, or from about 0.001 wt % to about 0.005 wt %. In some embodiments, the storage condition has a storage temperature of from about 2° C. to about 10° C. or from about 16° C. to about 26° C. In some embodiments, the ophthalmic composition has a dose-to-dose muscarinic antagonist concentration variation of one of: less than 50%, less than 40%, less than 30%, less than 20%, less than 10%, or less than 5%. In some embodiments, the dose-to-dose muscarinic antagonist concentration variation is based on one of: 10 consecutive doses, 8 consecutive doses, 5 consecutive doses, 3 consecutive doses, or 2 consecutive doses.

Other features and technical effects of the methods and compositions described herein will become apparent from the following detailed description. It should be understood, however, that the detailed description and the specific examples, while indicating specific embodiments, are given by way of illustration only.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Figures 1A, 1B, 1C:
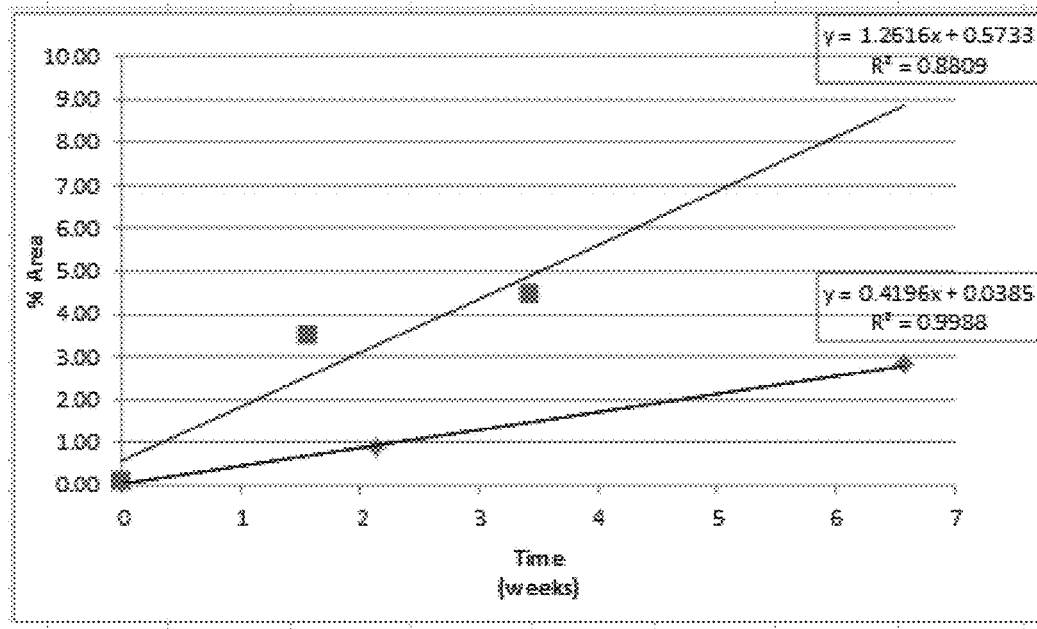
FIG. 1A-FIG. 1C show the shelf life prediction of 0.01% atropine sulfate solution with a primary degradant RRT 0.87-0.89, and a n.m.t. of 0.5% area, based on data obtained from samples stored at 25° C. and 40° C. The pH range of the atropine sulfate solution is from 5.9-6.2.

The present disclosure recognizes that there is a need for a stabilized ophthalmic composition with extended shelf life upon storage. The present disclosure also recognizes that there is a need for stabilizing an ophthalmic composition through arresting or reducing hydrolysis of at least some of its active agents. The present disclosure further recognizes that there is a need for an ophthalmic composition that provides convenient and effective delivery of a muscarinic antagonist such as atropine in the eye of a patient.

The present disclosure recognizes that muscarinic antagonist (e.g. atropine or its pharmaceutically acceptable salts) prevents or arrests the development of myopia in humans, for example as evidenced by reduction of the rate of increase of myopia in young people. The present disclosure also recognizes the effects of muscarinic antagonist (e.g. atropine or its pharmaceutically acceptable salts) on reduction of axial elongation and myopia in visually impaired chick eyes, and on ocular growth and muscarinic cholinergic receptors in young rhesus monkeys.

In addition, the present disclosure recognizes that systemic absorption of muscarinic antagonist (e.g. atropine) sometimes leads to undesirable side effect, and that localized delivery of muscarinic antagonist (e.g. atropine or its pharmaceutically acceptable salts) reduces or prevents the aforementioned systemic exposure.

Further, the present disclosure recognizes that some liquid muscarinic antagonist (e.g. atropine) compositions are formulated at a relatively lower pH range (e.g. less than 4.5) for stability of muscarinic antagonist (e.g. atropine or its pharmaceutically acceptable salts). For some individuals, the lower pH range in some instances causes discomfort or other side effects such as pain or burning sensation in the eye, which is prevented or alleviated by formulating muscarinic antagonist (e.g. atropine) compositions at higher pH ranges. For some individuals, the lower pH in some instances elicits a tear response which reduces the absorption of the drug in the eye and therefore the effectiveness.

Still further, the present disclosure recognizes that some muscarinic antagonist (e.g. atropine) liquid compositions formulated at lower concentrations (e.g. 0.001% to 0.05%) present stability challenges that are less so in higher concentrations (e.g. 0.1-1%). Without wishing to be bound by any particular theory, it is contemplated that the some muscarinic antagonist (e.g. atropine) contributes to the stability of an ophthalmic composition, such as an aqueous solution. For example, the concentration of the muscarinic antagonist (e.g. atropine) in some embodiments affects the pH or pD of the ophthalmic composition, such as with the muscarinic antagonist acting as a buffering agent. Furthermore, the concentration of the muscarinic antagonist (e.g. atropine) in some embodiments affects the interaction between the muscarinic antagonist and other ingredients of the ophthalmic composition, which in turn affects the stability of the ophthalmic composition.

Finally, the present disclosure recognizes that deuterated water stabilizes ophthalmic compositions. In some cases, the deuterated water is a weak acid as compared to $H_2O$, as such deuterated water comprises a lower concentration of the reactive species (e.g., —OD) which in some instances leads to base catalyzed hydrolysis of an active agent in the ophthalmic composition. As such, in some instances compositions comprising deuterated water leads to reduced base catalyzed hydrolysis when compared to compositions comprising $H_2O$. In some instances, deuterated water further lowers the buffering capacity of an ophthalmic composition, leading to less tear reflex in the eye.

Myopia, axial elongation of the eye, affects a large proportion of the population. The onset of myopia is generally during the grade school years and progresses until growth of the eye is completed. The present disclosure recognizes the importance of compositions and treatments for preventing or arresting the development of myopia, especially compositions and treatments that allow convenient administration, reduce potential side effects, has suitable stability, and/or provide relatively consistent therapeutic effects.

Ophthalmic Muscarinic Antagonist Composition

Provided herein is an ophthalmic composition containing low concentrations of an ophthalmic agent. In some embodiments, the ophthalmic composition includes from about 0.001 wt % to about 0.05 wt % of an ophthalmic agent for treatment of an ophthalmic disorder or condition; and an ophthalmically acceptable carrier, wherein the ophthalmic agent is distributed with substantial uniformity throughout the ophthalmically acceptable carrier. In some instances, the ophthalmic agent is a muscarinic antagonist.

Provided herein is an ophthalmic composition containing low concentrations of a muscarinic antagonist. In some embodiments, the ophthalmic composition includes from about 0.001 wt % to about 0.05 wt % of a muscarinic antagonist for treatment of an ophthalmic disorder or condition; and an ophthalmically acceptable carrier, wherein the muscarinic antagonist is distributed with substantial uniformity throughout the ophthalmically acceptable carrier.

In some instances, the muscarinic antagonist includes atropine, atropine sulfate, noratropine, atropine-N-oxide, tropine, tropic acid, atropine methonitrate, diphenhydramine, dimenhydrinate, dicyclomine, flavoxate, oxybutynin, tiotropium, hyoscine, scopolomine (L-hyoscine), hydroxyzine, ipratropium, tropicamide, cyclopentolate, pirenzapine, homatropine, solifenacin, darifenacin, benzatropine, mebeverine, procyclidine, aclidinium bromide, trihexyphenidyl/benzhexol, tolterodine, or a combination thereof. In some instances, the muscarinic antagonist includes atropine, atropine sulfate, noratropine, atropine-N-oxide, tropine, tropic acid, hyoscine, scopolomine, tropicamide, cyclopentolate, pirenzapine, homatropine, or a combination thereof. In some embodiments, the muscarinic antagonist is atropine, or a pharmaceutically acceptable salt or prodrug thereof. In some embodiments, the muscarinic antagonist is atropine sulfate.

In some embodiments, the ophthalmic composition comprise a muscarinic antagonist selected from atropine, atropine sulfate, noratropine, atropine-N-oxide, tropine, tropic acid, atropine methonitrate, diphenhydramine, dimenhydrinate, dicyclomine, flavoxate, oxybutynin, tiotropium, hyoscine, scopolomine (L-hyoscine), hydroxyzine, ipratropium, tropicamide, cyclopentolate, pirenzapine, homatropine, solifenacin, darifenacin, benzatropine, mebeverine, procyclidine, aclidinium bromide, trihexyphenidyl/benzhexol, tolterodine, or a combination thereof. In some instances, the muscarinic antagonist includes atropine, atropine sulfate, noratropine, atropine-N-oxide, tropine, tropic acid, hyoscine, scopolomine, tropicamide, cyclopentolate, pirenzapine, or homatropine.

In some embodiments, the ophthalmic composition comprise two or more muscarinic antagonists in which the two or more muscarinic antagonists comprises atropine, atropine sulfate, noratropine, atropine-N-oxide, tropine, tropic acid, atropine methonitrate, diphenhydramine, dimenhydrinate, dicyclomine, flavoxate, oxybutynin, tiotropium, hyoscine, scopolomine (L-hyoscine), hydroxyzine, ipratropium, tropicamide, cyclopentolate, pirenzapine, homatropine, solifenacin, darifenacin, benzatropine, mebeverine, procyclidine, aclidinium bromide, trihexyphenidyl/benzhexol, tolterodine, or a combination thereof. In some instances, the muscarinic antagonist includes atropine, atropine sulfate, noratropine, atropine-N-oxide, tropine, tropic acid, hyoscine, scopolomine, tropicamide, cyclopentolate, pirenzapine, homatropine, or any combination thereof.

In some embodiments, the ophthalmic composition comprises one or more muscarinic antagonist in combination with one or more sympathetic agonists. In some embodiments, the sympathetic agonist is selected from phenylephrine or hydroxyamphetamine. In some embodiments, the ophthalmic composition comprises one or more of muscarinic antagonist: atropine, atropine sulfate, noratropine, atropine-N-oxide, tropine, tropic acid, atropine methonitrate, diphenhydramine, dimenhydrinate, dicyclomine, flavoxate, oxybutynin, tiotropium, hyoscine, scopolomine (L-hyoscine), hydroxyzine, ipratropium, tropicamide, cyclopentolate, pirenzapine, homatropine, solifenacin, darifenacin, benzatropine, mebeverine, procyclidine, aclidinium bromide, trihexyphenidyl/benzhexol, or tolterodine; in combination with one or more of sympathetic agonists: phenylephrine or hydroxyamphetamine.

Provided herein is an ophthalmic composition containing low concentrations of atropine or its pharmaceutically acceptable salts. In some embodiments, the ophthalmic composition includes from about 0.001 wt % to about 0.05 wt % of atropine or its pharmaceutically acceptable salts for treatment of an ophthalmic disorder or condition; and an ophthalmically acceptable carrier, wherein the ophthalmic agent is distributed with substantial uniformity throughout the ophthalmically acceptable carrier.

Provided herein is an ophthalmic composition containing low concentrations of atropine sulfate. In some embodiments, the ophthalmic composition includes from about 0.001 wt % to about 0.05 wt % of atropine sulfate for treatment of an ophthalmic disorder or condition; and an ophthalmically acceptable carrier, wherein the ophthalmic agent is distributed with substantial uniformity throughout the ophthalmically acceptable carrier.

In some embodiments, the ophthalmic disorder or condition is pre-myopia, myopia or progression of myopia.

The present disclosure further recognizes that the clinical use of atropine as a therapy has been limited due to its ocular side effects including glare from pupillary dilation and blurred vision due to loss of accommodation. Without wishing to be bound by any particular theory, it is contemplated that the limited use of atropine against myopia development, include its ocular side effects, is attributable to the concentration of atropine used in known ophthalmic formulations (e.g. 1 wt % or higher).

The present disclosure further recognizes the challenges present in formulation of compositions that contain low concentrations, especially very low concentrations (e.g. from about 0.001 wt % to about 0.5 wt %), of ophthalmic agents, such as muscarinic antagonist (e.g. atropine or its pharmaceutically acceptable salts). In particular, pharmaceutical compositions with ophthalmic agent at such low concentrations are difficult to maintain dose-to-dose uniformity in term of ophthalmic agent content and/or distribution.

In some aspects, described herein are formulations or solutions of muscarinic antagonist (e.g., atropine) formulated in deuterated water. In some aspects, formulations or solutions of muscarinic antagonist (e.g., atropine) formulated in deuterated water are stable at different temperatures, at different relative humidity, with an acidic pD, and with a potency of at least 80% relative to the ophthalmic agent. In additional aspects, formulations or solutions of muscarinic antagonist (e.g., atropine) formulated in deuterated water has a lowered buffering capacity. In such instances, the lowered buffering capacity of the ophthalmic formulations or solutions when administered into the eye allows the ophthalmic formulation or solution to reach physiological pH at a faster rate than compared to an equivalent ophthalmic formulation or solution formulated in $H_2O$.

In some aspects, described herein are formulations of muscarinic antagonist (e.g. atropine) at low concentrations that does not have a dose-to-dose variation. In some aspects, described herein are formulations of muscarinic antagonist (e.g. atropine) at low concentrations that are stable at different temperatures, at different relative humidity, with an acidic pD, and with a potency of at least 80% relative to the ophthalmic agent.

In other aspects, described herein include formulating the ophthalmic composition as an ophthalmic gel or an ophthalmic ointment. For example, some ophthalmic gel or an ophthalmic ointment described herein allows desirable dose-to-dose uniformity, reduced or limited systemic exposure, or combinations thereof.

Ophthalmic Solution Muscarinic Antagonist Composition

Disclosed herein, in certain embodiments, is an ophthalmic composition formulated as an aqueous solution. In some embodiments, the ophthalmic composition comprises from about 0.001 wt % to about 0.05 wt % of a muscarinic antagonist and deuterated water. As used herein, deuterated water refers to $D_2O$, DHO, heavy water, and/or deuterium oxide.

In some embodiments, the composition comprises at least about 80% of the ophthalmic agent (e.g. muscarinic antagonist) for an extended period of time under storage condition. In some embodiments, the composition comprises at least about 81% of the ophthalmic agent (e.g. muscarinic antagonist) for an extended period of time under storage condition. In some embodiments, the composition comprises at least about 82% of the ophthalmic agent (e.g. muscarinic antagonist) for an extended period of time under storage condition. In some embodiments, the composition comprises at least about 83% of the ophthalmic agent (e.g. muscarinic antagonist) for an extended period of time under storage condition. In some embodiments, the composition comprises at least about 84% of the ophthalmic agent (e.g. muscarinic antagonist) for an extended period of time under storage condition. In some embodiments, the composition comprises at least about 85% of the ophthalmic agent (e.g. muscarinic antagonist) for an extended period of time under storage condition. In some embodiments, the composition comprises at least about 86% of the ophthalmic agent (e.g. muscarinic antagonist) for an extended period of time under storage condition. In some embodiments, the composition comprises at least about 87% of the ophthalmic agent (e.g. muscarinic antagonist) for an extended period of time under storage condition. In some embodiments, the composition comprises at least about 88% of the ophthalmic agent (e.g. muscarinic antagonist) for an extended period of time under storage condition. In some embodiments, the composition comprises at least about 89% of the ophthalmic agent (e.g. muscarinic antagonist) for an extended period of time under storage condition. In some embodiments, the composition comprises at least about 90% of the ophthalmic agent (e.g. muscarinic antagonist) for an extended period of time under storage condition. In some embodiments, the composition comprises at least about 91% of the ophthalmic agent (e.g. muscarinic antagonist) for an extended period of time under storage condition. In some embodiments, the composition comprises at least about 92% of the ophthalmic agent (e.g. muscarinic antagonist) for an extended period of time under storage condition. In some embodiments, the composition comprises at least about 93% of the ophthalmic agent (e.g. muscarinic antagonist) for an extended period of time under storage condition. In some embodiments, the composition comprises at least about 94% of the ophthalmic agent (e.g. muscarinic antagonist) for an extended period of time under storage condition. In some embodiments, the composition comprises at least about 95% of the ophthalmic agent (e.g. muscarinic antagonist) for an extended period of time under storage condition. In some embodiments, the composition comprises at least about 96% of the ophthalmic agent (e.g. muscarinic antagonist) for an extended period of time under storage condition. In some embodiments, the composition comprises at least about 97% of the ophthalmic agent (e.g. muscarinic antagonist) for an extended period of time under storage condition. In some embodiments, the composition comprises at least about 98% of the ophthalmic agent (e.g. muscarinic antagonist) for an extended period of time under storage condition. In some embodiments, the composition comprises at least about 99% of the ophthalmic agent (e.g. muscarinic antagonist) for an extended period of time under storage condition.

In some embodiments, the composition has a potency of at least about 80% after extended period of time under storage condition. In some embodiments, the composition has a potency of at least about 81% after extended period of time under storage condition. In some embodiments, the composition has a potency of at least about 82% after extended period of time under storage condition. In some embodiments, the composition has a potency of at least about 83% after extended period of time under storage condition. In some embodiments, the composition has a potency of at least about 84% after extended period of time under storage condition. In some embodiments, the composition has a potency of at least about 85% after extended period of time under storage condition. In some embodiments, the composition has a potency of at least about 86% after extended period of time under storage condition. In some embodiments, the composition has a potency of at least about 87% after extended period of time under storage condition. In some embodiments, the composition has a potency of at least about 88% after extended period of time under storage condition. In some embodiments, the composition has a potency of at least about 89% after extended period of time under storage condition. In some embodiments, the composition has a potency of at least 90% after extended period of time under storage condition. In some embodiments, the composition has a potency of at least 91% after extended period of time under storage condition. In some embodiments, the composition has a potency of at least 92% after extended period of time under storage condition. In some embodiments, the composition has a potency of at least 93% after extended period of time under storage condition. In some embodiments, the composition has a potency of at least 94% after extended period of time under storage condition. In some embodiments, the composition has a potency of at least 95% after extended period of time under storage condition. In some embodiments, the composition has a potency of at least 96% after extended period of time under storage condition. In some embodiments, the composition has a potency of at least 97% after extended period of time under storage condition. In some embodiments, the composition has a potency of at least 98% after extended period of time under storage condition. In some embodiments, the composition has a potency of at least 99% after extended period of time under storage condition.

In some embodiments, the extended period of time is at least 1 week. In some embodiments, the extended period of time is at least 2 weeks. In some embodiments, the extended period of time is at least 3 weeks. In some embodiments, the extended period of time is at least 1 month. In some embodiments, the extended period of time is at least 2 months. In some embodiments, the extended period of time is at least 3 months. In some embodiments, the extended period of time is at least 4 months. In some embodiments, the extended period of time is at least 5 months. In some embodiments, the extended period of time is at least 6 months. In some embodiments, the extended period of time is at least 7 months. In some embodiments, the extended period of time is at least 8 months. In some embodiments, the extended period of time is at least 9 months. In some embodiments, the extended period of time is at least 10 months. In some embodiments, the extended period of time is at least 11 months. In some embodiments, the extended period of time is at least 12 months (i.e. 1 year). In some embodiments, the extended period of time is at least 18 months (i.e. 1.5 years). In some embodiments, the extended period of time is at least 24 months (i.e. 2 years). In some embodiments, the extended period of time is at least 36 months (i.e. 3 years). In some embodiments, the extended period of time is at least 3 years. In some embodiments, the extended period of time is at least 5 years, or more.

In some embodiments, the temperature of the storage condition is between about 20° C. and about 70° C. In some embodiments, the temperature of the storage condition is between about 25° C. and about 65° C., about 30° C. and about 60° C., about 35° C. and about 55° C., or about 40° C. and about 50° C. In some embodiments, the temperature of the storage condition is about 25° C. In some embodiments, the temperature of the storage condition is about 40° C. In some embodiments, the temperature of the storage condition is about 60° C.

In some embodiments, the relative humidity of the storage condition is between about 50% and about 80%, or between about 60% and about 75%. In some embodiments, the relative humidity of the storage condition is about 60%. In some embodiments, the relative humidity of the storage condition is about 75%.

In some embodiments, the composition comprises less than 60% of $H_2O$. In some embodiments, the composition comprises less than 55% of $H_2O$. In some embodiments, the composition comprises less than 50% of $H_2O$. In some embodiments, the composition comprises less than 45% of $H_2O$. In some embodiments, the composition comprises less than 40% of $H_2O$. In some embodiments, the composition comprises less than 35% of $H_2O$. In some embodiments, the composition comprises less than 30% of $H_2O$. In some embodiments, the composition comprises less than 25% of $H_2O$. In some embodiments, the composition comprises less than 20% of $H_2O$. In some embodiments, the composition comprises less than 15% of $H_2O$. In some embodiments, the composition comprises less than 10% of $H_2O$.

In some embodiments, the composition comprises from less than 5% of $H_2O$ to 0% of $H_2O$. In some embodiments, the composition comprises less than 5% of $H_2O$. In some embodiments, the composition comprises less than 4.5% of $H_2O$. In some embodiments, the composition comprises less than 4% of $H_2O$. In some embodiments, the composition comprises less than 3.5% of $H_2O$. In some embodiments, the composition comprises less than 3% of $H_2O$. In some embodiments, the composition comprises less than 2.5% of $H_2O$. In some embodiments, the composition comprises less than 2% of $H_2O$. In some embodiments, the composition comprises less than 1.5% of $H_2O$. In some embodiments, the composition comprises less than 1% of $H_2O$. In some embodiments, the composition comprises less than 0.5% of $H_2O$. In some embodiments, the composition comprises less than 0.4% of $H_2O$. In some embodiments, the composition comprises less than 0.3% of $H_2O$. In some embodiments, the composition comprises less than 0.2% of $H_2O$. In some embodiments, the composition comprises less than 0.1% of $H_2O$. In some embodiments, the composition comprises 0% of $H_2O$.

In some embodiments, the composition has a pD of between about 4 and about 8, about 4.5 and about 7.8, about 5 and about 7.5, or about 5.5 and about 7. In some embodiments, the composition has a pD of less than about 7.5. In some embodiments, the composition has a pD of less than about 7.4. In some embodiments, the composition has a pD of less than about 7.3. In some embodiments, the composition has a pD of less than about 7.2. In some embodiments, the composition has a pD of less than about 7.1. In some embodiments, the composition has a pD of less than about 7. In some embodiments, the composition has a pD of less than about 6.9. In some embodiments, the composition has a pD of less than about 6.8. In some embodiments, the composition has a pD of less than about 6.7. In some embodiments, the composition has a pD of less than about 6.6. In some embodiments, the composition has a pD of less than about 6.5. In some embodiments, the composition has a pD of less than about 6.4. In some embodiments, the composition has a pD of less than about 6.3. In some embodiments, the composition has a pD of less than about 6.2. In some embodiments, the composition has a pD of less than about 6.1. In some embodiments, the composition has a pD of less than about 6. In some embodiments, the composition has a pD of less than about 5.9. In some embodiments, the composition has a pD of less than about 5.8. In some embodiments, the composition has a pD of less than about 5.7. In some embodiments, the composition has a pD of less than about 5.6. In some embodiments, the composition has a pD of less than about 5.5. In some embodiments, the composition has a pD of less than about 5.4. In some embodiments, the composition has a pD of less than about 5.3. In some embodiments, the composition has a pD of less than about 5.2. In some embodiments, the composition has a pD of less than about 5.1. In some embodiments, the composition has a pD of less than about 5. In some embodiments, the composition has a pD of less than about 4.9. In some embodiments, the composition has a pD of less than about 4.8. In some embodiments, the composition has a pD of less than about 4.7. In some embodiments, the composition has a pD of less than about 4.6. In some embodiments, the composition has a pD of less than about 4.5. In some embodiments, the composition has a pD of less than about 4.4. In some embodiments, the composition has a pD of less than about 4.3. In some embodiments, the composition has a pD of less than about 4.2. In some embodiments, the composition has a pD of less than about 4.1. In some embodiments, the composition has a pD of less than about 4.

In some embodiments, the composition comprising deuterated water has a lowered buffering capacity than an equivalent composition comprising $H_2O$. As described elsewhere herein, in some embodiments, the lowered buffering capacity allows the composition comprising deuterated water to normalize to physiological pH at a faster rate than a composition comprising $H_2O$. In some embodiments, the lowered buffering capacity allows the composition to induce less tear reflex than an equivalent composition comprising $H_2O$.

In some instances, the composition comprising deuterated water stabilizes muscarinic antagonist (e.g., atropine). In some embodiments, this is due to a lower concentration of the reactive species (e.g., —OD) in the $D_2O$ aqueous system compared to the concentration of the reactive species (e.g., —OH) in an equivalent $H_2O$ aqueous system. In some cases, base catalyzed hydrolysis leads to the presence of tropine degradant from atropine. In some cases, with a lower concentration of the reactive species that causes tropine degradant formation, atropine solution is more stable in a $D_2O$ aqueous system than compared to an equivalent $H_2O$ aqueous system. In some embodiments, the ophthalmic composition formulated with deuterated water allows for a more stable ophthalmic composition relative to the ophthalmic composition formulated with $H_2O$.

In some embodiments, the composition comprises less than 20% of major degradant based on the concentration of the ophthalmic agent after extended period of time under storage condition. In some embodiments, the composition comprises less than 15% of major degradant based on the concentration of the ophthalmic agent after extended period of time under storage condition.

In some embodiments, the composition comprises less than 10% of major degradant based on the concentration of the ophthalmic agent after extended period of time under storage condition. In some embodiments, the composition comprises less than 5% of major degradant based on the concentration of the ophthalmic agent after extended period of time under storage condition. In some embodiments, the composition comprises less than 2.0% of major degradant based on the concentration of the ophthalmic agent after extended period of time under storage condition. In some embodiments, the composition comprises less than 1.5% of major degradant based on the concentration of the ophthalmic agent after extended period of time under storage condition. In some embodiments, the composition comprises less than 1.0% of major degradant based on the concentration of the ophthalmic agent after extended period of time under storage condition. In some embodiments, the composition comprises less than 0.5% of major degradant based on the concentration of the ophthalmic agent after extended period of time under storage condition. In some embodiments, the composition comprises less than 0.4% of major degradant based on the concentration of the ophthalmic agent after extended period of time under storage condition. In some embodiments, the composition comprises less than 0.3% of major degradant based on the concentration of the ophthalmic agent after extended period of time under storage condition. In some embodiments, the composition comprises less than 0.2% of major degradant based on the concentration of the ophthalmic agent after extended period of time under storage condition. In some embodiments, the composition comprises less than 0.1% of major degradant based on the concentration of the ophthalmic agent after extended period of time under storage condition. In some embodiments, the major degradant is tropic acid.

In some embodiments, the primary degradant is an early eluting related substance at RRT of 0.87-0.89 according to the UPLC method described herein (Table 10). In some instances, the early eluting related substance is referred to as RRT 0.87-0.89. In some embodiments, the primary degradant is RRT 0.87-0.89.

Ophthalmic Muscarinic Antagonist Concentration

In some embodiments, the compositions described herein have a concentration of ophthalmic agent between about 0.001% to about 0.050%, between about 0.005% to about 0.050%, between about 0.010% to about 0.050%, between about 0.015% to about 0.050%, between about 0.020% to about 0.050%, between about 0.025% to about 0.050%, between about 0.030% to about 0.050%, between about 0.035% to about 0.050%, between about 0.040% to about 0.050%, or between about 0.045% to about 0.050% of the ophthalmic agent, or pharmaceutically acceptable prodrug or salt thereof, by weight of the composition. In some instances, the prodrug of the ophthalmic agent (e.g. muscarinic antagonist) is chemically converted into the ophthalmic agent (e.g. muscarinic antagonist) after the administration of the ophthalmic composition. In a non-limiting example, the muscarinic antagonist prodrug has a chemical bond that is cleavable by one or more enzymes in tears. In some embodiments, the ophthalmic agent is a muscarinic antagonist. In some embodiments, the muscarinic antagonist comprises atropine, atropine sulfate, noratropine, atropine-N-oxide, tropine, tropic acid, hyoscine, scopolomine, tropicamide, cyclopentolate, pirenzapine, homatropine, or a combination thereof. In some embodiments, the muscarinic antagonist is atropine, or a pharmaceutically acceptable salt thereof. In some embodiments, the muscarinic antagonist is atropine sulfate. As described herein, the ophthalmic agent includes optically pure stereoisomers, optically enriched stereoisomers, and a racemic mixture of stereoisomers. For example, some ophthalmic compositions disclosed herein includes atropine or atropine sulfate in which the atropine is a racemic mixture of D- and L-isomers; and some ophthalmic compositions disclosed herein includes atropine or atropine sulfate in which the atropine is a optically enriched in favor of the more ophthalmically active L-isomer.

In some embodiments, the compositions described herein have a concentration of ophthalmic agent between about 0.001% to about 0.045%, between about 0.005% to about 0.045%, between about 0.010% to about 0.045%, between about 0.015% to about 0.045%, between about 0.020% to about 0.045%, between about 0.025% to about 0.045%, between about 0.030% to about 0.045%, between about 0.035% to about 0.045%, or between about 0.040% to about 0.045% of the ophthalmic agent, or pharmaceutically acceptable prodrug or salt thereof, by weight of the composition. In some embodiments, the ophthalmic agent is a muscarinic antagonist. In some embodiments, the muscarinic antagonist comprises atropine, atropine sulfate, noratropine, atropine-N-oxide, tropine, tropic acid, hyoscine, scopolomine, tropicamide, cyclopentolate, pirenzapine, homatropine, or a combination thereof. In some embodiments, the muscarinic antagonist is atropine, or a pharmaceutically acceptable salt thereof. In some embodiments, the muscarinic antagonist is atropine sulfate.

In some embodiments, the compositions described herein have a concentration of ophthalmic agent between about 0.001% to about 0.040%, between about 0.005% to about 0.040%, between about 0.010% to about 0.040%, between about 0.015% to about 0.040%, between about 0.020% to about 0.040%, between about 0.025% to about 0.040%, between about 0.030% to about 0.040%, between about 0.035% to about 0.040% of the active ingredient, or pharmaceutically acceptable prodrug or salt thereof, by weight of the composition. In some embodiments, the ophthalmic agent is a muscarinic antagonist. In some embodiments, the muscarinic antagonist comprises atropine, atropine sulfate, noratropine, atropine-N-oxide, tropine, tropic acid, hyoscine, scopolomine, tropicamide, cyclopentolate, pirenzapine, homatropine, or a combination thereof. In some embodiments, the muscarinic antagonist is atropine, or a pharmaceutically acceptable salt thereof. In some embodiments, the muscarinic antagonist is atropine sulfate.

In some embodiments, the compositions described herein have a concentration of ophthalmic agent between about 0.001% to about 0.035%, between about 0.005% to about 0.035%, between about 0.010% to about 0.035%, between about 0.015% to about 0.035%, between about 0.020% to about 0.035%, between about 0.025% to about 0.035%, or between about 0.030% to about 0.035% of the ophthalmic agent, or pharmaceutically acceptable prodrug or salt thereof, by weight of the composition. In some embodiments, the ophthalmic agent is a muscarinic antagonist. In some embodiments, the muscarinic antagonist comprises atropine, atropine sulfate, noratropine, atropine-N-oxide, tropine, tropic acid, hyoscine, scopolomine, tropicamide, cyclopentolate, pirenzapine, homatropine, or a combination thereof. In some embodiments, the muscarinic antagonist is atropine, or a pharmaceutically acceptable salt thereof. In some embodiments, the muscarinic antagonist is atropine sulfate.

In some embodiments, the compositions described herein have a concentration of ophthalmic agent between about 0.001% to about 0.030%, between about 0.005% to about 0.030%, between about 0.010% to about 0.030%, between about 0.015% to about 0.030%, between about 0.020% to about 0.030%, or between about 0.025% to about 0.030% of the active ingredient, or pharmaceutically acceptable prodrug or salt thereof, by weight of the composition. In some embodiments, the ophthalmic agent is a muscarinic antagonist. In some embodiments, the muscarinic antagonist comprises atropine, atropine sulfate, noratropine, atropine-N-oxide, tropine, tropic acid, hyoscine, scopolomine, tropicamide, cyclopentolate, pirenzapine, homatropine, or a combination thereof. In some embodiments, the muscarinic antagonist is atropine, or a pharmaceutically acceptable salt thereof. In some embodiments, the muscarinic antagonist is atropine sulfate.

In some embodiments, the compositions described herein have a concentration of ophthalmic agent between about 0.001% to about 0.025%, between about 0.005% to about 0.025%, between about 0.010% to about 0.025%, between about 0.015% to about 0.025%, or between about 0.020% to about 0.025% of the ophthalmic agent, or pharmaceutically acceptable prodrug or salt thereof, by weight of the composition. In some embodiments, the ophthalmic agent is a muscarinic antagonist. In some embodiments, the muscarinic antagonist comprises atropine, atropine sulfate, noratropine, atropine-N-oxide, tropine, tropic acid, hyoscine, scopolomine, tropicamide, cyclopentolate, pirenzapine, homatropine, or a combination thereof. In some embodiments, the muscarinic antagonist is atropine, or a pharmaceutically acceptable salt thereof. In some embodiments, the muscarinic antagonist is atropine sulfate.

In some embodiments, the compositions described herein have a concentration of ophthalmic agent between about 0.001% to about 0.020%, between about 0.005% to about 0.020%, between about 0.010% to about 0.020%, or between about 0.015% to about 0.020% of the active ingredient, or pharmaceutically acceptable prodrug or salt thereof, by weight of the composition. In some embodiments, the ophthalmic agent is a muscarinic antagonist. In some embodiments, the muscarinic antagonist comprises atropine, atropine sulfate, noratropine, atropine-N-oxide, tropine, tropic acid, hyoscine, scopolomine, tropicamide, cyclopentolate, pirenzapine, homatropine, or a combination thereof. In some embodiments, the muscarinic antagonist is atropine, or a pharmaceutically acceptable salt thereof. In some embodiments, the muscarinic antagonist is atropine sulfate.

In some embodiments, the compositions described herein have a concentration of ophthalmic agent between about 0.001% to about 0.015%, between about 0.005% to about 0.015%, or between about 0.010% to about 0.015% of the ophthalmic agent, or pharmaceutically acceptable prodrug or salt thereof, by weight of the composition. In some embodiments, the ophthalmic agent is a muscarinic antagonist. In some embodiments, the muscarinic antagonist comprises atropine, atropine sulfate, noratropine, atropine-N-oxide, tropine, tropic acid, hyoscine, scopolomine, tropicamide, cyclopentolate, pirenzapine, homatropine, or a combination thereof. In some embodiments, the muscarinic antagonist is atropine, or a pharmaceutically acceptable salt thereof. In some embodiments, the muscarinic antagonist is atropine sulfate.

In some embodiments, the compositions described herein have a concentration of ophthalmic agent between about 0.001% to about 0.010%, between about 0.005% to about 0.010%, or between about 0.008% to about 0.010% of the ophthalmic agent, or pharmaceutically acceptable prodrug or salt thereof, by weight of the composition. In some embodiments, the ophthalmic agent is a muscarinic antagonist. In some embodiments, the muscarinic antagonist comprises atropine, atropine sulfate, noratropine, atropine-N-oxide, tropine, tropic acid, hyoscine, scopolomine, tropicamide, cyclopentolate, pirenzapine, homatropine, or a combination thereof. In some embodiments, the muscarinic antagonist is atropine, or a pharmaceutically acceptable salt thereof. In some embodiments, the muscarinic antagonist is atropine sulfate.

In some embodiments, the compositions described herein have a concentration of ophthalmic agent about 0.001%, 0.005%, 0.010%, 0.015%, 0.020%, 0.025%, 0.030%, 0.035%, 0.040%, 0.045%, or 0.050% of the ophthalmic agent, or pharmaceutically acceptable prodrug or salt thereof, by weight of the composition. In some embodiments, the ophthalmic agent is a muscarinic antagonist. In some embodiments, the muscarinic antagonist comprises atropine, atropine sulfate, noratropine, atropine-N-oxide, tropine, tropic acid, hyoscine, scopolomine, tropicamide, cyclopentolate, pirenzapine, homatropine, or a combination thereof. In some embodiments, the muscarinic antagonist is atropine, or a pharmaceutically acceptable salt thereof. In some embodiments, the muscarinic antagonist is atropine sulfate.

Without wishing to be bound by any particular theory, it is contemplated herein that the low concentration of the ophthalmic agent (e.g. muscarinic antagonist such as atropine or atropine sulfate) in the disclosed ophthalmic composition provides sufficient and consistent therapeutic benefits to an individual in need thereof, while reducing or avoiding the ocular side effects including glare from pupillary dilation and blurred vision due to loss of accommodation that are associated with ophthalmic formulations containing higher concentrations of the ophthalmic agent (e.g. muscarinic antagonist such as atropine or atropine sulfate).

Aqueous Solution Stability

In some embodiments, the composition described herein comprises a buffer. In some embodiments, a buffer is selected from borates, borate-polyol complexes, phosphate buffering agents, citrate buffering agents, acetate buffering agents, carbonate buffering agents, organic buffering agents, amino acid buffering agents, or combinations thereof. In some embodiments, the composition described herein comprises buffer comprising deuterated water. In some embodiments, a deuterated buffer is selected from borates, borate-polyol complexes, phosphate buffering agents, citrate buffering agents, acetate buffering agents, carbonate buffering agents, organic buffering agents, amino acid buffering agents, or combinations thereof, formulated in deuterated water.

In some instances, borates include boric acid, salts of boric acid, other pharmaceutically acceptable borates, and combinations thereof. In some cases, borates include boric acid, sodium borate, potassium borate, calcium borate, magnesium borate, manganese borate, and other such borate salts.

As used herein, the term polyol includes any compound having at least one hydroxyl group on each of two adjacent carbon atoms that are not in trans configuration relative to each other. In some embodiments, the polyols is linear or cyclic, substituted or unsubstituted, or mixtures thereof, so long as the resultant complex is water soluble and pharmaceutically acceptable. In some instances, examples of polyol include: sugars, sugar alcohols, sugar acids and uronic acids. In some cases, polyols include, but are not limited to; manritol, glycerin, xylitol and sorbitol.

In some embodiments, phosphate buffering agents include phosphoric acid; alkali metal phosphates such as disodium hydrogen phosphate, sodium dihydrogen phosphate, trisodium phosphate, dipotassium hydrogen phosphate, potassium dihydrogen phosphate, and tripotassium phosphate; alkaline earth metal phosphates such as calcium phosphate, calcium hydrogen phosphate, calcium dihydrogen phosphate, monomagnesium phosphate, dimagnesium phosphate (magnesium hydrogen phosphate), and trimagnesium phosphate; ammonium phosphates such as diammonium hydrogen phosphate and ammonium dihydrogen phosphate; or a combination thereof. In some instances, the phosphate buffering agent is an anhydride. In some instances, the phosphate buffering agent is a hydrate.

In some embodiments, borate-polyol complexes include those described in U.S. Pat. No. 6,503,497. In some instances, the borate-polyol complexes comprise borates in an amount of from about 0.01 to about 2.0% w/v, and one or more polyols in an amount of from about 0.01% to about 5.0% w/v.

In some cases, citrate buffering agents include citric acid and sodium citrate.

In some instances, acetate buffering agents include acetic acid, potassium acetate, and sodium acetate.

In some instances, carbonate buffering agents include sodium bicarbonate and sodium carbonate.

In some cases, organic buffering agents include Good's Buffer, such as for example 2-(N-morpholino)ethanesulfonic acid (MES), N-(2-Acetamido)iminodiacetic acid, N-(Carbamoylmethyl)iminodiacetic acid (ADA), piperazine-N,N'-bis(2-ethanesulfonic acid (PIPES), N-(2-acetamido)-2-aminoethanesulfonic acid (ACES), β-Hydroxy-4-morpholinepropanesulfonic acid, 3-Morpholino-2-hydroxypropanesulfonic acid (MOPSO), cholamine chloride, 3-(N-morpholino)propansulfonic acid (MOPS), N,N-bis(2-hydroxyethyl)-2-aminoethanesulfonic acid (BES), 2-[(2-Hydroxy-1,1-bis(hydroxymethyl)ethyl)amino] ethanesulfonic acid (TES), 4-(2-hydroxyethyl)-1-piperazineethanesulfonic acid (HEPES), 3-(N,N-Bis[2-hydroxyethyl]amino)-2-hydroxypropanesulfonic acid (DIPSO), acetamidoglycine, 3-{[1,3-Dihydroxy-2-(hydroxymethyl)-2-propanyl]amino}-2-hydroxy-1-propanesulfonic acid (TAPSO), piperazine-1,4,-bis (2-hydroxypropanesulphonic acid) (POPSO), 4-(2-hydroxyethyl)piperazine-1-(2-hydroxypropanesulfonic acid) hydrate (HEPPSO), 3-[4-(2-hydroxyethyl)-1-piperazinyl]propanesulfonic acid (HEPPS), tricine, glycinamide, bicine or N-tris(hydroxymethyl) methyl-3-aminopropanesulfonic acid sodium (TAPS); glycine; and diethanolamine (DEA).

In some cases, amino acid buffering agents include taurine, aspartic acid and its salts (e.g., potassium salts, etc), E-aminocaproic acid, and the like.

In some instances, the composition described herein further comprises a tonicity adjusting agent. Tonicity adjusting agent is an agent introduced into a preparation such as an ophthalmic composition to reduce local irritation by preventing osmotic shock at the site of application. In some instances, buffer solution and/or a pD adjusting agent that broadly maintains the ophthalmic solution at a particular ion concentration and pD are considered as tonicity adjusting agents. In some cases, tonicity adjusting agents include various salts, such as halide salts of a monovalent cation. In some cases, tonicity adjusting agents include mannitol, sorbitol, dextrose, sucrose, urea, and glycerin. In some instances, suitable tonicity adjustors comprise sodium chloride, sodium nitrate, sodium sulfate, sodium bisulfate, potassium chloride, calcium chloride, magnesium chloride, zinc chloride, potassium acetate, sodium acetate, sodium bicarbonate, sodium carbonate, sodium thiosulfate, magnesium sulfate, disodium hydrogen phosphate, sodium dihydrogen phosphate, potassium dihydrogen phosphate, dextrose, mannitol, sorbitol, dextrose, sucrose, urea, propylene glycol, glycerin, or a combination thereof.

In some instances, the concentration of the tonicity adjusting agent in a composition described herein is between about 0.5% and about 2.0%. In some instances, the concentration of the tonicity adjusting agent in a composition described herein is between about 0.7% and about 1.8%, about 0.8% and about 1.5%, or about 1% and about 1.3%. In some instances, the concentration of the tonicity adjusting agent is about 0.6%, 0.7%, 0.8%, 0.9%, 1.0%, 1.1%, 1.2%, 1.3%, 1.4%, 1.5%, 1.6%, 1.7%, 1.8%, or 1.9%. In some cases, the percentage is a weight percentage.

In some cases, the composition described herein further comprises a pD adjusting agent. In some embodiments, the pD adjusting agent used is an acid or a base. In some embodiments, the base is oxides, hydroxides, carbonates, bicarbonates and the likes. In some instances, the oxides are metal oxides such as calcium oxide, magnesium oxide and the likes; hydroxides are of alkali metals and alkaline earth metals such as sodium hydroxide, potassium hydroxide, calcium hydroxide and the likes or their deuterated equivalents, and carbonates are sodium carbonate, sodium bicarbonates, potassium bicarbonates and the likes. In some instances, the acid is mineral acid and organic acids such as hydrochloric acid, nitric acid, phosphoric acid, acetic acid, citric acid, fumaric acid, malic acid tartaric acid and the likes or their deuterated equivalents. In some instances, the pD adjusting agent includes, but is not limited to, acetate, bicarbonate, ammonium chloride, citrate, phosphate, pharmaceutically acceptable salts thereof and combinations or mixtures thereof. In some embodiments, the pD adjusting agent comprises DCl and NaOD.

In some instances, the composition has a pD of between about 4 and about 8, about 4.5 and about 7.8, about 5 and about 7.5, or about 5.5 and about 7. In some embodiments, the composition has a pD of less than about 7.5. In some embodiments, the composition has a pD of less than about 7.4. In some embodiments, the composition has a pD of less than about 7.3. In some embodiments, the composition has a pD of less than about 7.2. In some embodiments, the composition has a pD of less than about 7.1. In some embodiments, the composition has a pD of less than about 7. In some embodiments, the composition has a pD of less than about 6.9. In some embodiments, the composition has a pD of less than about 6.8. In some embodiments, the composition has a pD of less than about 6.7. In some embodiments, the composition has a pD of less than about 6.6. In some embodiments, the composition has a pD of less than about 6.5. In some embodiments, the composition has a pD of less than about 6.4. In some embodiments, the composition has a pD of less than about 6.3. In some embodiments, the composition has a pD of less than about 6.2. In some embodiments, the composition has a pD of less than about 6.1. In some embodiments, the composition has a pD of less than about 6. In some embodiments, the composition has a pD of less than about 5.9. In some embodiments, the composition has a pD of less than about 5.8. In some embodiments, the composition has a pD of less than about 5.7. In some embodiments, the composition has a pD of less than about 5.6. In some embodiments, the composition has a pD of less than about 5.5. In some embodiments, the composition has a pD of less than about 5.4. In some embodiments, the composition has a pD of less than about 5.3. In some embodiments, the composition has a pD of less than about 5.2. In some embodiments, the composition has a pD of less than about 5.1. In some embodiments, the composition has a pD of less than about 5. In some embodiments, the composition has a pD of less than about 4.9. In some embodiments, the composition has a pD of less than about 4.8. In some embodiments, the composition has a pD of less than about 4.7. In some embodiments, the composition has a pD of less than about 4.6. In some embodiments, the composition has a pD of less than about 4.5. In some embodiments, the composition has a pD of less than about 4.4. In some embodiments, the composition has a pD of less than about 4.3. In some embodiments, the composition has a pD of less than about 4.2. In some embodiments, the composition has a pD of less than about 4.1. In some embodiments, the composition has a pD of less than about 4. In some embodiments, the pD is the pD of the composition after extended period of time under storage condition.

In some instances, the composition has an initial pD of between about 4 and about 8, about 4.5 and about 7.8, about 5 and about 7.5, or about 5.5 and about 7. In some embodiments, the composition has an initial pD of about 7.5. In some embodiments, the composition has an initial pD of about 7.4. In some embodiments, the composition has an initial pD of about 7.3. In some embodiments, the composition has an initial pD of about 7.2. In some embodiments, the composition has an initial pD of about 7.1. In some embodiments, the composition has an initial pD of about 7. In some embodiments, the composition has an initial pD of about 6.9. In some embodiments, the composition has an initial pD of about 6.8. In some embodiments, the composition has an initial pD of about 6.7. In some embodiments, the composition has an initial pD of about 6.6. In some embodiments, the composition has an initial pD of about 6.5. In some embodiments, the composition has an initial pD of about 6.4. In some embodiments, the composition has an initial pD of about 6.3. In some embodiments, the composition has an initial pD of about 6.2. In some embodiments, the composition has an initial pD of about 6.1. In some embodiments, the composition has an initial pD of about 6. In some embodiments, the composition has an initial pD of about 5.9. In some embodiments, the composition has an initial pD of about 5.8. In some embodiments, the composition has an initial pD of about 5.7. In some embodiments, the composition has an initial pD of about 5.6. In some embodiments, the composition has an initial pD of about 5.5. In some embodiments, the composition has an initial pD of about 5.4. In some embodiments, the composition has an initial pD of about 5.3. In some embodiments, the composition has an initial pD of about 5.2. In some embodiments, the composition has an initial pD of about 5.1. In some embodiments, the composition has an initial pD of about 5. In some embodiments, the composition has an initial pD of about 4.9. In some embodiments, the composition has an initial pD of about 4.8. In some embodiments, the composition has an initial pD of about 4.7. In some embodiments, the composition has an initial pD of about 4.6. In some embodiments, the composition has an initial pD of about 4.5. In some embodiments, the composition has an initial pD of about 4.4. In some embodiments, the composition has an initial pD of about 4.3. In some embodiments, the composition has an initial pD of about 4.2. In some embodiments, the composition has an initial pD of about 4.1. In some embodiments, the composition has an initial pD of about 4.

In some embodiments, the pD of the composition described herein is associated with the stability of the composition. In some embodiments, a stable composition comprises a pD of between about 4 and about 8, about 4.5 and about 7.8, about 5 and about 7.5, or about 5.5 and about 7. In some embodiments, a stable composition comprises a pD of less than about 7.5. In some embodiments, a stable composition comprises a pD of less than about 7.4. In some embodiments, a stable composition comprises a pD of less than about 7.3. In some embodiments, a stable composition comprises a pD of less than about 7.2. In some embodiments, a stable composition comprises a pD of less than about 7.1. In some embodiments, a stable composition comprises a pD of less than about 7. In some embodiments, a stable composition comprises a pD of less than about 6.9. In some embodiments, a stable composition comprises a pD of less than about 6.8. In some embodiments, a stable composition comprises a pD of less than about 6.7. In some embodiments, a stable composition comprises a pD of less than about 6.6. In some embodiments, a stable composition comprises a pD of less than about 6.5. In some embodiments, a stable composition comprises a pD of less than about 6.4. In some embodiments, a stable composition comprises a pD of less than about 6.3. In some embodiments, a stable composition comprises a pD of less than about 6.2. In some embodiments, a stable composition comprises a pD of less than about 6.1. In some embodiments, a stable composition comprises a pD of less than about 6. In some embodiments, a stable composition comprises a pD of less than about 5.9. In some embodiments, a stable composition comprises a pD of less than about 5.8. In some embodiments, a stable composition comprises a pD of less than about 5.7. In some embodiments, a stable composition comprises a pD of less than about 5.6. In some embodiments, a stable composition comprises a pD of less than about 5.5. In some embodiments, a stable composition comprises a pD of less than about 5.4. In some embodiments, a stable composition comprises a pD of less than about 5.3. In some embodiments, a stable composition comprises a pD of less than about 5.2. In some embodiments, a stable composition comprises a pD of less than about 5.1. In some embodiments, a stable composition comprises a pD of less than about 5. In some embodiments, a stable composition comprises a pD of less than about 4.9. In some embodiments, a stable composition comprises a pD of less than about 4.8. In some embodiments, a stable composition comprises a pD of less than about 4.7. In some embodiments, a stable composition comprises a pD of less than about 4.6. In some embodiments, a stable composition comprises a pD of less than about 4.5. In some embodiments, a stable composition comprises a pD of less than about 4.4. In some embodiments, a stable composition comprises a pD of less than about 4.3. In some embodiments, a stable composition comprises a pD of less than about 4.2. In some embodiments, a stable composition comprises a pD of less than about 4.1. In some embodiments, a stable composition comprises a pD of less than about 4.

As described elsewhere herein, in some instances, the $D_2O$ aqueous system stabilizes a muscarinic antagonist (e.g., atropine). In some embodiments, this is due to a lower concentration of the reactive species (e.g., —OD) in the $D_2O$ aqueous system compared to the concentration of the reactive species (e.g., —OH) in an equivalent $H_2O$ aqueous system. In some instances, the concentration of the reactive species (e.g., —OD) in the $D_2O$ aqueous system is about one third less than the concentration of the reactive species (e.g., —OH) in the equivalent $H_2O$ aqueous system. In some cases, this is due to a lower or smaller dissociation constant of $D_2O$ than $H_2O$. For example, the $K_a(H_2O)$ is $1\times10^{-14}$, whereas the $K_a(D_2O)$ is $1\times10^{-15}$. As such, $D_2O$ is a weaker acid than $H_2O$. In some cases, base catalyzed hydrolysis leads to the presence of tropine degradant from atropine. In some cases, with a lower concentration of the reactive species that causes tropine degradant formation, atropine solution is more stable in a $D_2O$ aqueous system than compared to an equivalent $H_2O$ aqueous system. In some embodiments, the ophthalmic composition formulated with deuterated water allows for a more stable ophthalmic composition relative to the ophthalmic composition formulated with $H_2O$.

In some embodiments, the presence of deuterated water shifts the pKa of the buffer. In some embodiments, the presence of deuterated water allows for the ophthalmic composition to simulate the stability of a lower pH system. In some instances, the buffer capacity of the ophthalmic composition is lowered, thereby allowing a faster shift in pH. In some instances, the lowered buffering capacity of the ophthalmic composition when administered into the eye allows the ophthalmic composition to reach physiological pH at a faster rate than compared to an ophthalmic composition formulated in $H_2O$. In some instances, the ophthalmic composition formulated with deuterated water allows for a lower tear production, or less tear reflex in the eye, in comparison with an ophthalmic composition formulated with $H_2O$.

In some instances, the composition described herein further comprises a disinfecting agent. In some cases, disinfecting agents include polymeric biguanides, polymeric quarternary ammonium compounds, chlorites, bisbiguanides, chlorite compounds (e.g. potassium chlorite, sodium chlorite, calcium chlorite, magnesium chlorite, or mixtures thereof), and a combination thereof.

In some instances, the composition described herein further comprises a preservative. In some cases, a preservative is added at a concentration to a composition described herein to prevent the growth of or to destroy a microorganism introduced into the composition. In some instances, microorganisms refer to bacteria (e.g. *Proteus mirabilis, Serratia marcesens*), virus (e.g. Herpes simplex virus, herpes zoster virus), fungus (e.g. fungi from the genus *Fusarium*), yeast (e.g. *Candida albicans*), parasites (e.g. *Plasmodium* spp., *Gnathostoma* spp.), protozoan (e.g. *Giardia lamblia*), nematodes (e.g. *Onchocercus volvulus*), worm (e.g. *Dirofilaria immitis*), and/or amoeba (e.g. Acanthameoba).

In some instances, the concentration of the preservative is between about 0.0001% and about 1%, about 0.001% and about 0.8%, about 0.004% and about 0.5%, about 0.008% and about 0.1%, and about 0.01% and about 0.08%. In some cases, the concentration of the preservatives is about 0.001%, 0.002%, 0.003%, 0.004%, 0.005%, 0.006%, 0.008%, 0.009%, 0.009%, 0.01%, 0.015%, 0.02%, 0.025%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9% or 1.0%.

In some embodiments, the preservative is selected from benzalkonium chloride, cetrimonium, sodium perborate, stabilized oxychloro complex, SofZia (Alcon), polyquaternium-1, chlorobutanol, edetate disodium, and polyhexamethylene biguanide.

In some embodiments, the composition described herein is stored in a plastic container. In some embodiments, the material of the plastic container comprises high density polyethylene (HDPE), low density polyethylene (LDPE), polyethylene terephthalate (PET), polyvinyl chloride (PVC), polyprolyene (PP), polystyrene (PS), fluorine treated HDPE, post-consumer resin (PCR), K-resine (SBC), or bioplastic. In some embodiments, the material of the plastic container comprises LDPE.

In some embodiments, the composition described herein is stored in a plastic container. In some embodiments, the composition stored in a plastic container has a pD of between about 4 and about 8, about 4.5 and about 7.9, or about 4.9 and about 7.5. In some embodiments, the composition stored in a plastic container has a pD of less than about 7.4. In some embodiments, the composition stored in a plastic container has a pD of less than about 7.3. In some embodiments, the composition stored in a plastic container has a pD of less than about 7.2. In some embodiments, the composition stored in a plastic container has a pD of less than about 7.1. In some embodiments, the composition stored in a plastic container has a pD of less than about 7. In some embodiments, the composition stored in a plastic container has a pD of less than about 6.9. In some embodiments, the composition stored in a plastic container has a pD of less than about 6.8. In some embodiments, the composition stored in a plastic container has a pD of less than about 6.7. In some embodiments, the composition stored in a plastic container has a pD of less than about 6.6. In some embodiments, the composition stored in a plastic container has a pD of less than about 6.5. In some embodiments, the composition stored in a plastic container has a pD of less than about 6.4. In some embodiments, the composition stored in a plastic container has a pD of less than about 6.3. In some embodiments, the composition stored in a plastic container has a pD of less than about 6.2. In some embodiments, the composition stored in a plastic container has a pD of less than about 6.1. In some embodiments, the composition stored in a plastic container has a pD of less than about 6. In some embodiments, the composition stored in a plastic container has a pD of less than about 5.9. In some embodiments, the composition stored in a plastic container has a pD of less than about 5.8. In some embodiments, the composition stored in a plastic container has a pD of less than about 5.7. In some embodiments, the composition stored in a plastic container has a pD of less than about 5.6. In some embodiments, the composition stored in a plastic container has a pD of less than about 5.5. In some embodiments, the composition stored in a plastic container has a pD of less than about 5.4. In some embodiments, the composition stored in a plastic container has a pD of less than about 5.3. In some embodiments, the composition stored in a plastic container has a pD of less than about 5.2. In some embodiments, the composition stored in a plastic container has a pD of less than about 5.1. In some embodiments, the composition stored in a plastic container has a pD of less than about 5. In some embodiments, the composition stored in a plastic container has a pD of less than about 4.9. In some embodiments, the composition stored in a plastic container has a pD of less than about 4.8. In some embodiments, the composition stored in a plastic container has a pD of less than about 4.7. In some embodiments, the composition stored in a plastic container has a pD of less than about 4.6. In some embodiments, the composition stored in a plastic container has a pD of less than about 4.5. In some embodiments, the composition stored in a plastic container has a pD of less than about 4.4. In some embodiments, the composition stored in a plastic container has a pD of less than about 4.3. In some embodiments, the composition stored in a plastic container has a pD of less than about 4.2. In some embodiments, the composition stored in a plastic container has a pD of less than about 4.1. In some embodiments, the composition stored in a plastic container has a pD of less than about 4.

In some embodiments, the composition stored in a plastic container has a potency of at least 80% after extended period of time under storage condition. In some embodiments, the composition stored in a plastic container has a potency of at least 85% after extended period of time under storage condition. In some embodiments, the composition stored in a plastic container has a potency of at least 90% after extended period of time under storage condition. In some embodiments, the composition stored in a plastic container has a potency of at least 93% after extended period of time under storage condition. In some embodiments, the composition stored in a plastic container has a potency of at least 95% after extended period of time under storage condition. In some embodiments, the composition stored in a plastic container has a potency of at least 97% after extended period of time under storage condition. In some embodiments, the composition stored in a plastic container has a potency of at least 98% after extended period of time under storage condition. In some embodiments, the composition stored in a plastic container has a potency of at least 99% after extended period of time under storage condition. In some instances, the storage condition comprises a temperature of about 25° C., about 40° C., or about 60° C. In some instances, the extended period of time is at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months.

In some embodiments, the composition stored in a plastic container has a potency of at least 80% at a temperature of about 25° C., about 40° C., or about 60° C. In some embodiments, the composition stored in a plastic container has a potency of at least 85% at a temperature of about 25° C., about 40° C., or about 60° C. In some embodiments, the composition stored in a plastic container has a potency of at least 90% at a temperature of about 25° C., about 40° C., or about 60° C. In some embodiments, the composition stored in a plastic container has a potency of at least 93% at a temperature of about 25° C., about 40° C., or about 60° C. In some embodiments, the composition stored in a plastic container has a potency of at least 95% at a temperature of about 25° C., about 40° C., or about 60° C. In some embodiments, the composition stored in a plastic container has a potency of at least 97% at a temperature of about 25° C., about 40° C., or about 60° C. In some embodiments, the composition stored in a plastic container has a potency of at least 98% at a temperature of about 25° C., about 40° C., or about 60° C. In some embodiments, the composition stored in a plastic container has a potency of at least 99% at a temperature of about 25° C., about 40° C., or about 60° C.

In some embodiments, the composition stored in a plastic container has a potency of at least 80% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container has a potency of at least 85% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container has a potency of at least 90% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container has a potency of at least 93% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container has a potency of at least 95% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container has a potency of at least 97% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container has a potency of at least 98% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container has a potency of at least 99% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months.

In some embodiments, the composition stored in a plastic container comprises less than 20% of primary degradant based on the concentration of the ophthalmic agent after extended period of time under storage condition. In some embodiments, the composition stored in a plastic container comprises less than 15% of primary degradant based on the concentration of the ophthalmic agent after extended period of time under storage condition. In some embodiments, the composition stored in a plastic container comprises less than 10% of primary degradant based on the concentration of the ophthalmic agent after extended period of time under storage condition. In some embodiments, the composition stored in a plastic container comprises less than 5% of primary degradant based on the concentration of the ophthalmic agent after extended period of time under storage condition.

In some embodiments, the composition stored in a plastic container comprises from less than 2.5% of primary degradant to less than 0.1% of primary degradant based on the concentration of the ophthalmic agent after extended period of time under storage condition. In some embodiments, the composition stored in a plastic container comprises less than 2.5% of primary degradant based on the concentration of the ophthalmic agent after extended period of time under storage condition. In some embodiments, the composition stored in a plastic container comprises less than 2.0% of primary degradant based on the concentration of the ophthalmic agent after extended period of time under storage condition. In some embodiments, the composition stored in a plastic container comprises less than 1.5% of primary degradant based on the concentration of the ophthalmic agent after extended period of time under storage condition. In some embodiments, the composition stored in a plastic container comprises less than 1.0% of primary degradant based on the concentration of the ophthalmic agent after extended period of time under storage condition. In some embodiments, the composition stored in a plastic container comprises less than 0.5% of primary degradant based on the concentration of the ophthalmic agent after extended period of time under storage condition. In some embodiments, the composition stored in a plastic container comprises less than 0.4% of primary degradant based on the concentration of the ophthalmic agent after extended period of time under storage condition. In some embodiments, the composition stored in a plastic container comprises less than 0.3% of primary degradant based on the concentration of the ophthalmic agent after extended period of time under storage condition. In some embodiments, the composition stored in a plastic container comprises less than 0.2% of primary degradant based on the concentration of the ophthalmic agent after extended period of time under storage condition. In some embodiments, the composition stored in a plastic container comprises less than 0.1% of primary degradant based on the concentration of the ophthalmic agent after extended period of time under storage condition. In some instances, the storage condition comprises a temperature of about 25° C., about 40° C., or about 60° C. In some instances, the extended period of time is at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months.

In some embodiments, the composition stored in a plastic container comprises less than 20% of primary degradant based on the concentration of the ophthalmic agent at a temperature of about 25° C., about 40° C., or about 60° C. In some embodiments, the composition stored in a plastic container comprises less than 15% of primary degradant based on the concentration of the ophthalmic agent at a temperature of about 25° C., about 40° C., or about 60° C. In some embodiments, the composition stored in a plastic container comprises less than 10% of primary degradant based on the concentration of the ophthalmic agent at a temperature of about 25° C., about 40° C., or about 60° C. In some embodiments, the composition stored in a plastic container comprises less than 5% of primary degradant based on the concentration of the ophthalmic agent at a temperature of about 25° C., about 40° C., or about 60° C.

In some embodiments, the composition stored in a plastic container comprises from less than 2.5% of primary degradant to less than 0.1% of primary degradant based on the concentration of the ophthalmic agent at a temperature of about 25° C., about 40° C., or about 60° C. In some embodiments, the composition stored in a plastic container comprises less than 2.5% of primary degradant based on the concentration of the ophthalmic agent at a temperature of about 25° C., about 40° C., or about 60° C. In some embodiments, the composition stored in a plastic container comprises less than 2.0% of primary degradant based on the concentration of the ophthalmic agent at a temperature of about 25° C., about 40° C., or about 60° C. In some embodiments, the composition stored in a plastic container comprises less than 1.5% of primary degradant based on the concentration of the ophthalmic agent at a temperature of about 25° C., about 40° C., or about 60° C. In some embodiments, the composition stored in a plastic container comprises less than 1.0% of primary degradant based on the concentration of the ophthalmic agent at a temperature of about 25° C., about 40° C., or about 60° C. In some embodiments, the composition stored in a plastic container comprises less than 0.5% of primary degradant based on the concentration of the ophthalmic agent at a temperature of about 25° C., about 40° C., or about 60° C. In some embodiments, the composition stored in a plastic container comprises less than 0.4% of primary degradant based on the concentration of the ophthalmic agent at a temperature of about 25° C., about 40° C., or about 60° C. In some embodiments, the composition stored in a plastic container comprises less than 0.3% of primary degradant based on the concentration of the ophthalmic agent at a temperature of about 25° C., about 40° C., or about 60° C. In some embodiments, the composition stored in a plastic container comprises less than 0.2% of primary degradant based on the concentration of the ophthalmic agent at a temperature of about 25° C., about 40° C., or about 60° C. In some embodiments, the composition stored in a plastic container comprises less than 0.1% of primary degradant based on the concentration of the ophthalmic agent at a temperature of about 25° C., about 40° C., or about 60° C.

In some embodiments, the composition stored in a plastic container comprises less than 20% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 15% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 10% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 5% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months.

In some embodiments, the composition stored in a plastic container comprises from less than 2.5% of primary degradant to less than 0.1% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 2.5% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 2.0% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 1.5% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 1.0% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 0.5% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 0.4% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 0.3% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 0.2% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 0.1% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months.

In some embodiments, the composition described herein is stored in a glass container. In some embodiments, the glass container is a glass vial, such as for example, a type I, type II or type III glass vial. In some embodiments, the glass container is a type I glass vial. In some embodiments, the type I glass vial is a borasilicate glass vial.

In some embodiments, the composition stored in a glass container has a pD of higher than about 7. In some embodiments, the composition stored in a glass container has a pD of higher than about 7.5. In some embodiments, the composition stored in a glass container has a pD of higher than about 8. In some embodiments, the composition stored in a glass container has a pD of higher than about 8.5. In some embodiments, the composition stored in a glass container has a pD of higher than about 9.

In some embodiments, the composition stored in a glass container has a potency of less than 60% at a temperature of about 25° C., about 40° C., or about 60° C. In some embodiments, the composition stored in a glass container has a potency of less than 60% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months.

In some embodiments, the composition stored in a glass container is less stable than a composition stored in a plastic container.

In some embodiments, the composition is stored under in the dark. In some instances, the composition is stored in the presence of light. In some instances, the light is indoor light, room light, or sun light. In some instances, the composition is stable while stored in the presence of light.

In some embodiments, the composition described herein is formulated as an aqueous solution. In some embodiments, the aqueous solution is a stable aqueous solution. In some instances, the aqueous solution is stored in a plastic container as described above. In some instances, the aqueous solution is not stored in a glass container. In some instances, the aqueous solution is stored in the dark. In some instances, the aqueous solution is stored in the presence of light. In some instances, the aqueous solution is stable in the presence of light.

In a specific embodiment, the ophthalmically acceptable formulations alternatively comprise a cyclodextrin. Cyclodextrins are cyclic oligosaccharides containing 6, 7, or 8 glucopyranose units, referred to as α-cyclodextrin, β-cyclodextrin, or γ-cyclodextrin respectively. Cyclodextrins have a hydrophilic exterior, which enhances water-soluble, and a hydrophobic interior which forms a cavity. In an aqueous environment, hydrophobic portions of other molecules often enter the hydrophobic cavity of cyclodextrin to form inclusion compounds. Additionally, cyclodextrins are also capable of other types of nonbonding interactions with molecules that are not inside the hydrophobic cavity. Cyclodextrins have three free hydroxyl groups for each glucopyranose unit, or 18 hydroxyl groups on α-cyclodextrin, 21 hydroxyl groups on β-cyclodextrin, and 24 hydroxyl groups on γ-cyclodextrin. In some embodiments, one or more of these hydroxyl groups are reacted with any of a number of reagents to form a large variety of cyclodextrin derivatives, including hydroxypropyl ethers, sulfonates, and sulfoalkylethers. Shown below is the structure of β-cyclodextrin and the hydroxypropyl-β-cyclodextrin (HPβCD).

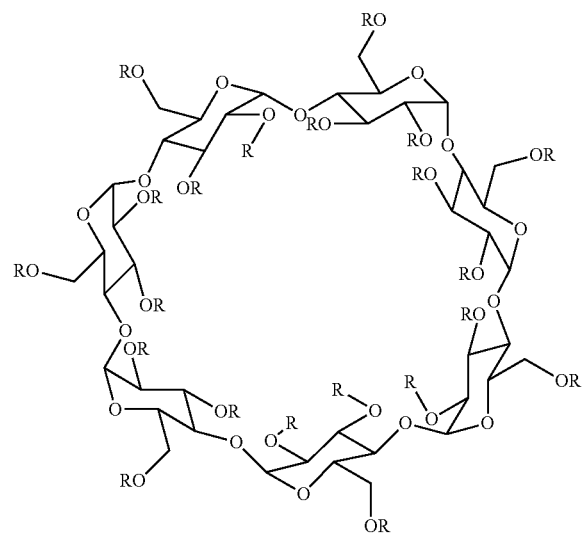

R = H
β-cyclodextrin

R = CH$_2$CH(OH)CH$_3$
hydroxypropyl β-cyclodextrin

In some embodiments, the use of cyclodextrins in the pharmaceutical compositions described herein improves the solubility of the drug. Inclusion compounds are involved in many cases of enhanced solubility; however other interactions between cyclodextrins and insoluble compounds also improves solubility. Hydroxypropyl-β-cyclodextrin (HPβCD) is commercially available as a pyrogen free product. It is a nonhygroscopic white powder that readily dissolves in water. HPβCD is thermally stable and does not degrade at neutral pH. Thus, cyclodextrins improve the solubility of a therapeutic agent in a composition or formulation. Accordingly, in some embodiments, cyclodextrins are included to increase the solubility of the ophthalmically acceptable ophthalmic agents within the formulations described herein. In other embodiments, cyclodextrins in addition serve as controlled release excipients within the formulations described herein.

By way of example only, cyclodextrin derivatives for use include α-cyclodextrin, β-cyclodextrin, γ-cyclodextrin, hydroxyethyl-β-cyclodextrin, hydroxypropyl-γ-cyclodextrin, sulfated β-cyclodextrin, sulfated α-cyclodextrin, sulfobutyl ether β-cyclodextrin.

The concentration of the cyclodextrin used in the compositions and methods disclosed herein varies according to the physiochemical properties, pharmacokinetic properties, side effect or adverse events, formulation considerations, or other factors associated with the therapeutically ophthalmic agent, or a salt or prodrug thereof, or with the properties of other excipients in the composition. Thus, in certain circumstances, the concentration or amount of cyclodextrin used in accordance with the compositions and methods disclosed herein will vary, depending on the need. When used, the amount of cyclodextrins needed to increase solubility of the ophthalmic agent and/or function as a controlled release excipient in any of the formulations described herein is selected using the principles, examples, and teachings described herein.

Other stabilizers that are useful in the ophthalmically acceptable formulations disclosed herein include, for example, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In some embodiments, amide analogues of stabilizers are also used. In further embodiments, the chosen stabilizer changes the hydrophobicity of the formulation, improves the mixing of various components in the formulation, controls the moisture level in the formula, or controls the mobility of the phase.

In other embodiments, stabilizers are present in sufficient amounts to inhibit the degradation of the ophthalmic agent. Examples of such stabilizing agents, include, but are not limited to: glycerol, methionine, monothioglycerol, EDTA, ascorbic acid, polysorbate 80, polysorbate 20, arginine, heparin, dextran sulfate, cyclodextrins, pentosan polysulfate and other heparinoids, divalent cations such as magnesium and zinc, or combinations thereof.

Additional useful stabilization agents for ophthalmically acceptable formulations include one or more anti-aggregation additives to enhance stability of ophthalmic formulations by reducing the rate of protein aggregation. The anti-aggregation additive selected depends upon the nature of the conditions to which the ophthalmic agents, for example a muscarinic antagonist (e.g. atropine or its pharmaceutically acceptable salts), are exposed. For example, certain formulations undergoing agitation and thermal stress require a different anti-aggregation additive than a formulation undergoing lyophilization and reconstitution. Useful anti-aggregation additives include, by way of example only, urea, guanidinium chloride, simple amino acids such as glycine or arginine, sugars, polyalcohols, polysorbates, polymers such as polyethylene glycol and dextrans, alkyl saccharides, such as alkyl glycoside, and surfactants.

Other useful formulations optionally include one or more ophthalmically acceptable antioxidants to enhance chemical stability where required. Suitable antioxidants include, by way of example only, ascorbic acid, methionine, sodium thiosulfate and sodium metabisulfite. In one embodiment, antioxidants are selected from metal chelating agents, thiol containing compounds and other general stabilizing agents.

Still other useful compositions include one or more ophthalmically acceptable surfactants to enhance physical stability or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

In some embodiments, the ophthalmically acceptable pharmaceutical formulations described herein are stable with respect to compound degradation (e.g. less than 30% degradation, less than 25% degradation, less than 20% degradation, less than 15% degradation, less than 10% degradation, less than 8% degradation, less than 5% degradation, less than 3% degradation, less than 2% degradation, or less than 5% degradation) over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 3 months, at least about 4 months, at least about 5 months, or at least about 6 months under storage conditions (e.g. room temperature). In other embodiments, the formulations described herein are stable with respect to compound degradation over a period of at least about 1 week. Also described herein are formulations that are stable with respect to compound degradation over a period of at least about 1 month.

In other embodiments, an additional surfactant (co-surfactant) and/or buffering agent is combined with one or more of the pharmaceutically acceptable vehicles previously described herein so that the surfactant and/or buffering agent maintains the product at an optimal pD for stability. Suitable co-surfactants include, but are not limited to: a) natural and synthetic lipophilic agents, e.g., phospholipids, cholesterol, and cholesterol fatty acid esters and derivatives thereof; b) nonionic surfactants, which include for example, polyoxyethylene fatty alcohol esters, sorbitan fatty acid esters (Spans), polyoxyethylene sorbitan fatty acid esters (e.g., polyoxyethylene (20) sorbitan monooleate (Tween 80), polyoxyethylene (20) sorbitan monostearate (Tween 60), polyoxyethylene (20) sorbitan monolaurate (Tween 20) and other Tweens, sorbitan esters, glycerol esters, e.g., Myrj and glycerol triacetate (triacetin), polyethylene glycols, cetyl alcohol, cetostearyl alcohol, stearyl alcohol, polysorbate 80, poloxamers, poloxamines, polyoxyethylene castor oil derivatives (e.g., Cremophor® RH40, Cremphor A25, Cremphor A20, Cremophor® EL) and other Cremophors, sulfosuccinates, alkyl sulphates (SLS); PEG glyceryl fatty acid esters such as PEG-8 glyceryl caprylate/caprate (Labrasol), PEG-4 glyceryl caprylate/caprate (Labrafac Hydro WL 1219), PEG-32 glyceryl laurate (Gelucire 444/14), PEG-6 glyceryl mono oleate (Labrafil M 1944 CS), PEG-6 glyceryl linoleate (Labrafil M 2125 CS); propylene glycol mono- and di-fatty acid esters, such as propylene glycol laurate, propylene glycol caprylate/caprate; Brij® 700, ascorbyl-6-palmitate, stearylamine, sodium lauryl sulfate, polyoxethyleneglycerol triiricinoleate, and any combinations or mixtures thereof; c) anionic surfactants include, but are not limited to, calcium carboxymethylcellulose, sodium carboxymethylcellulose, sodium sulfosuccinate, dioctyl, sodium alginate, alkyl polyoxyethylene sulfates, sodium lauryl sulfate, triethanolamine stearate, potassium laurate, bile salts, and any combinations or mixtures thereof; and d) cationic surfactants such as cetyltrimethylammonium bromide, and lauryldimethylbenzyl-ammonium chloride.

In a further embodiment, when one or more co-surfactants are utilized in the ophthalmically acceptable formulations of the present disclosure, they are combined, e.g., with a pharmaceutically acceptable vehicle and is present in the final formulation, e.g., in an amount ranging from about 0.1% to about 20%, from about 0.5% to about 10%.

In one embodiment, the surfactant has an HLB value of 0 to 20. In additional embodiments, the surfactant has an HLB value of 0 to 3, of 4 to 6, of 7 to 9, of 8 to 18, of 13 to 15, of 10 to 18.

In some embodiments, the pD of a composition described herein is adjusted (e.g., by use of a buffer and/or a pD adjusting agent) to an ophthalmically compatible pD range of from about 4 to about 8, about 4.5 to about 7.5, or about 5 to about 7. In some embodiments, the ophthalmic composition has a pD of from about 5.0 to about 7.0. In some embodiments, the ophthalmic composition has a pD of from about 5.5 to about 7.0. In some embodiments, the ophthalmic composition has a pD of from about 6.0 to about 7.0.

In some embodiments, useful formulations include one or more pD adjusting agents or buffering agents. Suitable pD adjusting agents or buffers include, but are not limited to acetate, bicarbonate, ammonium chloride, citrate, phosphate, deuterated forms of acetate, bicarbonate, ammonium chloride, citrate, phosphate, pharmaceutically acceptable salts thereof and combinations or mixtures thereof. In some embodiments, the pD adjusting agents or buffers include deuterated hydrochloric acid (DCl), deuterated sodium hydroxide (NaOD), deuterated acetic acid ($CD_3COOD$), or deuterated citric acid ($C_6D_8O_7$).

In one embodiment, when one or more buffers are utilized in the formulations of the present disclosure, they are combined, e.g., with a pharmaceutically acceptable vehicle and are present in the final formulation, e.g., in an amount ranging from about 0.1% to about 20%, from about 0.5% to about 10%. In certain embodiments of the present disclosure, the amount of buffer included in the gel formulations are an amount such that the pD of the gel formulation does not interfere with the body's natural buffering system.

In one embodiment, diluents are also used to stabilize compounds because they provide a more stable environment. In some instances, salts dissolved in buffered solutions (which also provides pD control or maintenance) are utilized as diluents in the art, including, but not limited to a phosphate buffered saline solution.

In some embodiments, the pD is calculated according to the formula disclosed in Glasoe et al., "Use of glass electrodes to measure acidities in deuterium oxide," J. Physical Chem. 64(1): 188-190 (1960). In some embodiment, the pD is calculated as pD=pH*+0.4, in which pH* is the measured or observed pH of the ophthalmic composition formulated in a solution comprising deuterated water (e.g., $D_2O$).

In some embodiments, the ophthalmic aqueous, gel, or ointment composition described herein has a pD of between about 4 and about 8, between about 4.5 and about 8, between about 4.9 and about 7.9, between about 5.4 and about 7.9, between about 5.9 and about 7.9, between about 6.4 and about 7.9, or between about 7.4 and about 7.9. In some embodiments, the ophthalmic aqueous, gel, or ointment composition described herein has a pD of between about 4.5-7.5, between about 5.0 and about 7.5, between about 5.5 and about 7.5, between about 6.0 and about 7.5, or between about 7.0 and about 7.5. In some embodiments, the ophthalmic aqueous, gel, or ointment composition described herein has a pD of between about 4.5-7.0, between about 5.0 and about 7.0, between about 5.5 and about 7.0, between about 6.0 and about 7.0, or between about 6.5 and about 7.0. In some embodiments, the ophthalmic aqueous, gel, or ointment composition described herein has a pD of between about 4.9-7.4, between about 5.4 and about 7.4, between about 5.9 and about 7.4, between about 6.4 and about 7.4, or between about 6.9 and about 7.4. In some embodiments, the ophthalmic aqueous, gel, or ointment composition described herein has a pD of between about 4.5-6.5, between about 5.0 and about 6.5, between about 5.5 and about 6.5, or between about 6.0 and about 6.5. In some embodiments, the ophthalmic aqueous, gel, or ointment composition described herein has a pD of between about 4.9-6.9, between about 5.4 and about 6.9, between about 5.9 and about 6.9, or between about 6.4 and about 6.9. In some embodiments, the ophthalmic aqueous, gel, or ointment composition described herein has a pD of between about 4.5-6.0, between about 5.0 and about 6.0, or between about 5.5 and about 6.0. In some embodiments, the ophthalmic aqueous, gel, or ointment composition described herein has a pD of between about 4.9-6.4, between about 5.4 and about 6.4, or between about 5.9 and about 6.4. In some embodiments, the ophthalmic aqueous, gel, or ointment composition described herein has a pD of between about 4.5-5.5, or between about 5.0 and about 5.5. In some embodiments, the ophthalmic aqueous, gel, or ointment composition described herein has a pD of between about 4.9-5.9, or between about 5.4 and about 5.9. In some embodiments, the ophthalmic aqueous, gel, or ointment composition described herein has a pD of between about 4.5-5.0. In some embodiments, the ophthalmic aqueous, gel, or ointment composition described herein has a pD of between about 4.9-5.4.

In some embodiments, the ophthalmic composition is an ophthalmic aqueous composition. In some instances, the ophthalmic aqueous composition has a pD of between about 4 and about 8, about 4.5 and about 7.8, about 5 and about 7.5, or about 5.5 and about 7. In some embodiments, the ophthalmic aqueous composition has a pD of about 7.5. In some embodiments, the ophthalmic aqueous composition has a pD of about 7.4. In some embodiments, the ophthalmic aqueous composition has a pD of about 7.3. In some embodiments, the ophthalmic aqueous composition has a pD of about 7.2. In some embodiments, the ophthalmic aqueous composition has a pD of about 7.1. In some embodiments, the ophthalmic aqueous composition has a pD of about 7. In some embodiments, the ophthalmic aqueous composition has a pD of about 6.9. In some embodiments, the ophthalmic aqueous composition has a pD of about 6.8. In some embodiments, the ophthalmic aqueous composition has a pD of about 6.7. In some embodiments, the ophthalmic aqueous composition has a pD of about 6.6. In some embodiments, the ophthalmic aqueous composition has a pD of about 6.5. In some embodiments, the ophthalmic aqueous composition has a pD of about 6.4. In some embodiments, the ophthalmic aqueous composition has a pD of about 6.3. In some embodiments, the ophthalmic aqueous composition has a pD of about 6.2. In some embodiments, the ophthalmic aqueous composition has a pD of about 6.1. In some embodiments, the ophthalmic aqueous composition has a pD of about 6. In some embodiments, the ophthalmic aqueous composition has a pD of about 5.9. In some embodiments, the ophthalmic aqueous composition has a pD of about 5.8. In some embodiments, the ophthalmic aqueous composition has a pD of about 5.7. In some embodiments, the ophthalmic aqueous composition has a pD of about 5.6. In some embodiments, the ophthalmic aqueous composition has a pD of about 5.5. In some embodiments, the ophthalmic aqueous composition has a pD of about 5.4. In some embodiments, the ophthalmic aqueous composition has a pD of about 5.3. In some embodiments, the ophthalmic aqueous composition has a pD of about 5.2. In some embodiments, the ophthalmic aqueous composition has a pD of about 5.1. In some embodiments, the ophthalmic aqueous composition has a pD of about 5. In some embodiments, the ophthalmic aqueous composition has a pD of about 4.9. In some embodiments, the ophthalmic aqueous composition has a pD of about 4.8. In some embodiments, the ophthalmic aqueous composition has a pD of about 4.7. In some embodiments, the ophthalmic aqueous composition has a pD of about 4.6. In some embodiments, the ophthalmic aqueous composition has a pD of about 4.5. In some embodiments, the ophthalmic aqueous composition has a pD of about 4.4. In some embodiments, the ophthalmic aqueous composition has a pD of about 4.3. In some embodiments, the ophthalmic aqueous composition has a pD of about 4.2. In some embodiments, the ophthalmic aqueous composition has a pD of about 4.1. In some embodiments, the ophthalmic aqueous composition has a pD of about 4. In some embodiments, the pD is an initial pD of the ophthalmic aqueous composition. In some embodiments, the pD is the pD of the ophthalmic aqueous composition after extended period of time under storage condition.

In some instances, the ophthalmic aqueous composition has an initial pD of between about 4 and about 8, about 4.5 and about 7.8, about 5 and about 7.5, or about 5.5 and about 7. In some embodiments, the ophthalmic aqueous composition has an initial pD of about 7.5. In some embodiments, the ophthalmic aqueous composition has an initial pD of about 7.4. In some embodiments, the ophthalmic aqueous composition has an initial pD of about 7.3. In some embodiments, the ophthalmic aqueous composition has an initial pD of about 7.2. In some embodiments, the ophthalmic aqueous composition has an initial pD of about 7.1. In some embodiments, the ophthalmic aqueous composition has an initial pD of about 7. In some embodiments, the ophthalmic aqueous composition has an initial pD of about 6.9. In some embodiments, the ophthalmic aqueous composition has an initial pD of about 6.8. In some embodiments, the ophthalmic aqueous composition has an initial pD of about 6.7. In some embodiments, the ophthalmic aqueous composition has an initial pD of about 6.6. In some embodiments, the ophthalmic aqueous composition has an initial pD of about 6.5. In some embodiments, the ophthalmic aqueous composition has an initial pD of about 6.4. In some embodiments, the ophthalmic aqueous composition has an initial pD of about 6.3. In some embodiments, the ophthalmic aqueous composition has an initial pD of about 6.2. In some embodiments, the ophthalmic aqueous composition has an initial pD of about 6.1. In some embodiments, the ophthalmic aqueous composition has an initial pD of about 6. In some embodiments, the ophthalmic aqueous composition has an initial pD of about 5.9. In some embodiments, the ophthalmic aqueous composition has an initial pD of about 5.8. In some embodiments, the ophthalmic aqueous composition has an initial pD of about 5.7. In some embodiments, the ophthalmic aqueous composition has an initial pD of about 5.6. In some embodiments, the ophthalmic aqueous composition has an initial pD of about 5.5. In some embodiments, the ophthalmic aqueous composition has an initial pD of about 5.4. In some embodiments, the ophthalmic aqueous composition has an initial pD of about 5.3. In some embodiments, the ophthalmic aqueous composition has an initial pD of about 5.2. In some embodiments, the ophthalmic aqueous composition has an initial pD of about 5.1. In some embodiments, the ophthalmic aqueous composition has an initial pD of about 5. In some embodiments, the ophthalmic aqueous composition has an initial pD of about 4.9. In some embodiments, the ophthalmic aqueous composition has an initial pD of about 4.8. In some embodiments, the ophthalmic aqueous composition has an initial pD of about 4.7. In some embodiments, the ophthalmic aqueous composition has an initial pD of about 4.6. In some embodiments, the ophthalmic aqueous composition has an initial pD of about 4.5. In some embodiments, the ophthalmic aqueous composition has an initial pD of about 4.4. In some embodiments, the ophthalmic aqueous composition has an initial pD of about 4.3. In some embodiments, the ophthalmic aqueous composition has an initial pD of about 4.2. In some embodiments, the ophthalmic aqueous composition has an initial pD of about 4.1. In some embodiments, the ophthalmic aqueous composition has an initial pD of about 4.

In some instances, the ophthalmic aqueous composition has a pD of between about 4 and about 8, about 4.5 and about 7.8, about 5 and about 7.5, or about 5.5 and about 7. In some embodiments, the ophthalmic aqueous composition has a pD of less than about 7.5. In some embodiments, the ophthalmic aqueous composition has a pD of less than about 7.4. In some embodiments, the ophthalmic aqueous composition has a pD of less than about 7.3. In some embodiments, the ophthalmic aqueous composition has a pD of less than about 7.2. In some embodiments, the ophthalmic aqueous composition has a pD of less than about 7.1. In some embodiments, the ophthalmic aqueous composition has a pD of less than about 7. In some embodiments, the ophthalmic aqueous composition has a pD of less than about 6.9. In some embodiments, the ophthalmic aqueous composition has a pD of less than about 6.8. In some embodiments, the ophthalmic aqueous composition has a pD of less than about 6.7. In some embodiments, the ophthalmic aqueous composition has a pD of less than about 6.6. In some embodiments, the ophthalmic aqueous composition has a pD of less than about 6.5. In some embodiments, the ophthalmic aqueous composition has a pD of less than about 6.4. In some embodiments, the ophthalmic aqueous composition has a pD of less than about 6.3. In some embodiments, the ophthalmic aqueous composition has a pD of less than about 6.2. In some embodiments, the ophthalmic aqueous composition has a pD of less than about 6.1. In some embodiments, the ophthalmic aqueous composition has a pD of less than about 6. In some embodiments, the ophthalmic aqueous composition has a pD of less than about 5.9. In some embodiments, the ophthalmic aqueous composition has a pD of less than about 5.8. In some embodiments, the ophthalmic aqueous composition has a pD of less than about 5.7. In some embodiments, the ophthalmic aqueous composition has a pD of less than about 5.6. In some embodiments, the ophthalmic aqueous composition has a pD of less than about 5.5. In some embodiments, the ophthalmic aqueous composition has a pD of less than about 5.4. In some embodiments, the ophthalmic aqueous composition has a pD of less than about 5.3. In some embodiments, the ophthalmic aqueous composition has a pD of less than about 5.2. In some embodiments, the ophthalmic aqueous composition has a pD of less than about 5.1. In some embodiments, the ophthalmic aqueous composition has a pD of less than about 5. In some embodiments, the ophthalmic aqueous composition has a pD of less than about 4.9. In some embodiments, the ophthalmic aqueous composition has a pD of less than about 4.8. In some embodiments, the ophthalmic aqueous composition has a pD of less than about 4.7. In some embodiments, the ophthalmic aqueous composition has a pD of less than about 4.6. In some embodiments, the ophthalmic aqueous composition has a pD of less than about 4.5. In some embodiments, the ophthalmic aqueous composition has a pD of less than about 4.4. In some embodiments, the ophthalmic aqueous composition has a pD of less than about 4.3. In some embodiments, the ophthalmic aqueous composition has a pD of less than about 4.2. In some embodiments, the ophthalmic aqueous composition has a pD of less than about 4.1. In some embodiments, the ophthalmic aqueous composition has a pD of less than about 4. In some embodiments, the pD is the pD of the ophthalmic aqueous composition after extended period of time under storage condition.

In some embodiments, the pD of the ophthalmic aqueous composition described herein is associated with the stability of the ophthalmic aqueous composition. In some embodiments, a stable composition comprises a pD of between about 4 and about 8, about 4.5 and about 7.8, about 5 and about 7.5, or about 5.5 and about 7. In some embodiments, a stable composition comprises a pD of less than about 7.5. In some embodiments, a stable composition comprises a pD of less than about 7.4. In some embodiments, a stable composition comprises a pD of less than about 7.3. In some embodiments, a stable composition comprises a pD of less than about 7.2. In some embodiments, a stable composition comprises a pD of less than about 7.1. In some embodiments, a stable composition comprises a pD of less than about 7. In some embodiments, a stable composition comprises a pD of less than about 6.9. In some embodiments, a stable composition comprises a pD of less than about 6.8. In some embodiments, a stable composition comprises a pD of less than about 6.7. In some embodiments, a stable composition comprises a pD of less than about 6.6. In some embodiments, a stable composition comprises a pD of less than about 6.5. In some embodiments, a stable composition comprises a pD of less than about 6.4. In some embodiments, a stable composition comprises a pD of less than about 6.3. In some embodiments, a stable composition comprises a pD of less than about 6.2. In some embodiments, a stable composition comprises a pD of less than about 6.1. In some embodiments, a stable composition comprises a pD of less than about 6. In some embodiments, a stable composition comprises a pD of less than about 5.9. In some embodiments, a stable composition comprises a pD of less than about 5.8. In some embodiments, a stable composition comprises a pD of less than about 5.7. In some embodiments, a stable composition comprises a pD of less than about 5.6. In some embodiments, a stable composition comprises a pD of less than about 5.5. In some embodiments, a stable composition comprises a pD of less than about 5.4. In some embodiments, a stable composition comprises a pD of less than about 5.3. In some embodiments, a stable composition comprises a pD of less than about 5.2. In some embodiments, a stable composition comprises a pD of less than about 5.1. In some embodiments, a stable composition comprises a pD of less than about 5. In some embodiments, a stable composition comprises a pD of less than about 4.9. In some embodiments, a stable composition comprises a pD of less than about 4.8. In some embodiments, a stable composition comprises a pD of less than about 4.7. In some embodiments, a stable composition comprises a pD of less than about 4.6. In some embodiments, a stable composition comprises a pD of less than about 4.5. In some embodiments, a stable composition comprises a pD of less than about 4.4. In some embodiments, a stable composition comprises a pD of less than about 4.3. In some embodiments, a stable composition comprises a pD of less than about 4.2. In some embodiments, a stable composition comprises a pD of less than about 4.1. In some embodiments, a stable composition comprises a pD of less than about 4.

In some embodiments, the $D_2O$ aqueous system stabilizes a muscarinic antagonist (e.g., atropine). In some embodiments, this is due to a lower concentration of the reactive species (e.g., —OD) in the $D_2O$ aqueous system compared to the concentration of the reactive species (e.g., —OH) in an equivalent $H_2O$ aqueous system. In some instances, the concentration of the reactive species (e.g., —OD) in the $D_2O$ aqueous system is about one third less than the concentration of the reactive species (e.g., —OH) in the equivalent $H_2O$ aqueous system. In some cases, this is due to a lower or smaller dissociation constant of $D_2O$ than $H_2O$. For example, the $K_a(H_2O)$ is $1\times10^{-14}$, whereas the $K_a(D_2O)$ is $1\times10^{15}$. As such, $D_2O$ is a weaker acid than $H_2O$. In some cases, base catalyzed hydrolysis leads to the presence of tropine degradant from atropine. In some cases, with a lower concentration of the reactive species that causes tropine degradant formation, atropine solution is more stable in a $D_2O$ aqueous system than compared to an equivalent $H_2O$ aqueous system. In some embodiments, the ophthalmic composition formulated with deuterated water allows for a more stable ophthalmic composition relative to the ophthalmic composition formulated with $H_2O$.

In some embodiments, the presence of deuterated water shifts the pKa of the buffer. In some embodiments, the presence of deuterated water allows for the ophthalmic composition to simulate the stability of a lower pH system. In some instances, the buffer capacity of the ophthalmic composition is lowered, thereby allowing a faster shift in pH. In some instances, the lowered buffering capacity of the ophthalmic composition when administered into the eye allows the ophthalmic composition to reach physiological pH at a faster rate than compared to an ophthalmic composition formulated in $H_2O$. In some instances, the ophthalmic composition formulated with deuterated water allows for a lower tear production, or less tear reflex in the eye, in comparison with an ophthalmic composition formulated with $H_2O$.

In some embodiment, the ophthalmic gel or ointment composition described herein has a pD of about 4, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, or about 7.9.

In some embodiment, the pD of the ophthalmic aqueous, gel, or ointment composition described herein is suitable for sterilization (e.g., by filtration or aseptic mixing or heat treatment and/or autoclaving (e.g., terminal sterilization)) of ophthalmic formulations described herein. As used in in the present disclosure, the term "aqueous composition" includes compositions that are based on $D_2O$.

In some embodiments, the pharmaceutical formulations described herein are stable with respect to pD over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 18 months, at least about 24 months, at least about 3 years, at least about 4 years, at least about 5 years, at least about 6 years, at least about 7 years, at least about 8 years, at least about 9 years, at least about 10 years, or more. In other embodiments, the formulations described herein are stable with respect to pD over a period of at least about 1 week. In other embodiments, the formulations described herein are stable with respect to pD over a period of at least about 2 weeks. In other embodiments, the formulations described herein are stable with respect to pD over a period of at least about 3 weeks. In other embodiments, the formulations described herein are stable with respect to pD over a period of at least about 1 month. Also described herein are formulations that are stable with respect to pD over a period of at least about 2 months, at least about 3 months, at least about 4 months, at least about 5 months, at least about 6 months, at least about 12 months, at least about 18 months, at least about 2 years, or more.

Aqueous Solution Dose-to-Dose Uniformity

Typical ophthalmic aqueous solutions are packaged in eye drop bottles and administered as drops. For example, a single administration (i.e. a single dose) of an ophthalmic aqueous solution includes a single drop, two drops, three drops or more into the eyes of the patient. In some embodiments, one dose of the ophthalmic aqueous solution described herein is one drop of the aqueous solution composition from the eye drop bottle.

In some cases, described herein include ophthalmic aqueous compositions which provide a dose-to-dose uniform concentrations. In some instances, the dose-to-dose uniform concentration does not present significant variations of drug content from one dose to another. In some instances, the dose-to-dose uniform concentration does provide consistent drug content from one dose to another.

In some embodiments, the composition has a dose-to-dose ophthalmic agent concentration variation of less than 50%. In some embodiments, the composition has a dose-to-dose ophthalmic agent concentration variation of less than 40%. In some embodiments, the composition has a dose-to-dose ophthalmic agent concentration variation of less than 30%. In some embodiments, the composition has a dose-to-dose ophthalmic agent concentration variation of less than 20%. In some embodiments, the composition has a dose-to-dose ophthalmic agent concentration variation of less than 10%. In some embodiments, the composition has a dose-to-dose ophthalmic agent concentration variation of less than 5%.

In some embodiments, the dose-to-dose ophthalmic agent concentration variation is based on 10 consecutive doses. In some embodiments, the dose-to-dose ophthalmic agent concentration variation is based on 8 consecutive doses. In some embodiments, the dose-to-dose ophthalmic agent concentration variation is based on 5 consecutive doses. In some embodiments, the dose-to-dose ophthalmic agent concentration variation is based on 3 consecutive doses. In some embodiments, the dose-to-dose ophthalmic agent concentration variation is based on 2 consecutive doses.

A nonsettling formulation should not require shaking to disperse drug uniformly. A "no-shake" formulation is potentially advantageous over formulations that require shaking for the simple reason that patients' shaking behavior is a major source of variability in the amount of drug dosed. It has been reported that patients often times do not or forget to shake their ophthalmic compositions that requires shaking before administering a dose, despite the instructions to shake that were clearly marked on the label. On the other hand, even for those patients who do shake the product, it is normally not possible to determine whether the shaking is adequate in intensity and/or duration to render the product uniform. In some embodiments, the ophthalmic gel compositions and ophthalmic ointment compositions described herein are "no-shake" formulations that maintained the dose-to-dose uniformity described herein.

To evaluate the dose-to-dose uniformity, drop bottles or tubes containing the ophthalmic aqueous compositions, the ophthalmic gel compositions, or ophthalmic ointment compositions are stored upright for a minimum of 12 hours prior to the start of the test. To simulate the recommended dosing of these products, predetermined number of drops or strips are dispensed from each commercial bottles or tubes at predetermined time intervals for an extended period of time or until no product was left in the bottle or tube. All drops and strips are dispensed into tared glass vials, capped, and stored at room temperature until analysis. Concentrations of a muscarinic antagonist such as atropine in the expressed drops were determined using a reverse-phase HPLC method.

Aqueous Solution Viscosity

In some embodiments, the composition has a Brookfield RVDV viscosity of from about 10 to about 50,000 cps at about 20° C. and sheer rate of $1$ $s^{-1}$. In some embodiments, the composition has a Brookfield RVDV viscosity of from about 100 to about 40,000 cps at about 20° C. and sheer rate of $1$ $s^{-1}$. In some embodiments, the composition has a Brookfield RVDV viscosity of from about 500 to about 30,000 cps at about 20° C. and sheer rate of $1$ $s^{-1}$. In some embodiments, the composition has a Brookfield RVDV viscosity of from about 1000 to about 20,000 cps at about 20° C. and sheer rate of $1$ $s^{-1}$. In some embodiments, the composition has a Brookfield RVDV viscosity of from about 2000 to about 10,000 cps at about 20° C. and sheer rate of $1$ $s^{-1}$. In some embodiments, the composition has a Brookfield RVDV viscosity of from about 4000 to about 8000 cps at about 20° C. and sheer rate of $1$ $s^{-1}$.

In some embodiments, the ophthalmic aqueous formulation contains a viscosity enhancing agent sufficient to provide a viscosity of between about 500 and 50,000 centipoise, between about 750 and 50,000 centipoise; between about 1000 and 50,000 centipoise; between about 1000 and 40,000 centipoise; between about 2000 and 30,000 centipoise; between about 3000 and 20,000 centipoise; between about 4000 and 10,000 centipoise, or between about 5000 and 8000 centipoise.

In some embodiments, the compositions described herein are low viscosity compositions at body temperature. In some embodiments, low viscosity compositions contain from about 1% to about 10% of a viscosity enhancing agent (e.g., gelling components such as polyoxyethylene-polyoxypropylene copolymers). In some embodiments, low viscosity compositions contain from about 2% to about 10% of a viscosity enhancing agent (e.g., gelling components such as polyoxyethylene-polyoxypropylene copolymers). In some embodiments, low viscosity compositions contain from about 5% to about 10% of a viscosity enhancing agent (e.g., gelling components such as polyoxyethylene-polyoxypropylene copolymers). In some embodiments, low viscosity compositions are substantially free of a viscosity enhancing agent (e.g., gelling components such as polyoxyethylene-polyoxypropylene copolymers). In some embodiments, a low viscosity ophthalmic agent composition described herein provides an apparent viscosity of from about 100 cP to about 10,000 cP. In some embodiments, a low viscosity ophthalmic agent composition described herein provides an apparent viscosity of from about 500 cP to about 10,000 cP. In some embodiments, a low viscosity ophthalmic agent composition described herein provides an apparent viscosity of from about 1000 cP to about 10,000 cP.

Osmolarity

In some embodiments, a composition disclosed herein is formulated in order to not disrupt the ionic balance of the eye. In some embodiments, a composition disclosed herein has an ionic balance that is the same as or substantially the same as the eye. In some embodiments, a composition disclosed herein does not does not disrupt the ionic balance of the eye.

As used herein, "practical osmolarity/osmolality" or "deliverable osmolarity/osmolality" means the osmolarity/osmolality of a composition as determined by measuring the osmolarity/osmolality of the ophthalmic agent and all excipients except the gelling and/or the thickening agent (e.g., polyoxyethylene-polyoxypropylene copolymers, carboxymethylcellulose or the like). The practical osmolarity of a composition disclosed herein is measured by a suitable method, e.g., a freezing point depression method as described in Viegas et. al., Int. J. Pharm., 1998, 160, 157-162. In some instances, the practical osmolarity of a composition disclosed herein is measured by vapor pressure osmometry (e.g., vapor pressure depression method) that allows for determination of the osmolarity of a composition at higher temperatures. In some instances, vapor pressure depression method allows for determination of the osmolarity of a composition comprising a gelling agent (e.g., a thermoreversible polymer) at a higher temperature wherein the gelling agent is in the form of a gel.

In some embodiments, the osmolarity at a target site of action (e.g., the eye) is about the same as the delivered osmolarity of a composition described herein. In some embodiments, a composition described herein has a deliverable osmolarity of about 150 mOsm/L to about 500 mOsm/L, about 250 mOsm/L to about 500 mOsm/L, about 250 mOsm/L to about 350 mOsm/L, about 280 mOsm/L to about 370 mOsm/L or about 250 mOsm/L to about 320 mOsm/L.

The practical osmolality of an ophthalmic composition disclosed herein is from about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 320 mOsm/kg, or from about 250 mOsm/kg to about 350 mOsm/kg or from about 280 mOsm/kg to about 320 mOsm/kg. In some embodiments, a composition described herein has a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 250 mOsm/L to about 320 mOsm/L, or about 280 mOsm/L to about 320 mOsm/L.

In some embodiments, suitable tonicity adjusting agents include, but are not limited to any pharmaceutically acceptable sugar, salt or any combinations or mixtures thereof, such as, but not limited to dextrose, glycerin, mannitol, sorbitol, sodium chloride, and other electrolytes. In some instances, the tonicity adjusting agent is selected from sodium chloride, sodium nitrate, sodium sulfate, sodium bisulfate, potassium chloride, calcium chloride, magnesium chloride, zinc chloride, potassium acetate, sodium acetate, sodium bicarbonate, sodium carbonate, sodium thiosulfate, magnesium sulfate, disodium hydrogen phosphate, sodium dihydrogen phosphate, potassium dihydrogen phosphate, dextrose, mannitol, sorbitol, dextrose, sucrose, urea, propylene glycol, glycerin, or a combination thereof.

In some embodiment, the ophthalmic compositions described herein include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Sterility

In some embodiments, the compositions are sterilized. Included within the embodiments disclosed herein are means and processes for sterilization of a pharmaceutical composition disclosed herein for use in humans. The goal is to provide a safe pharmaceutical product, relatively free of infection causing micro-organisms. The U. S. Food and Drug Administration has provided regulatory guidance in the publication "Guidance for Industry: Sterile Drug Products Produced by Aseptic Processing" available at: http://www.fda.gov/cder/guidance/5882fnl.htm, which is incorporated herein by reference in its entirety.

As used herein, sterilization means a process used to destroy or remove microorganisms that are present in a product or packaging. Any suitable method available for sterilization of objects and compositions is used. Available methods for the inactivation of microorganisms include, but are not limited to, the application of extreme heat, lethal chemicals, or gamma radiation. In some embodiments, a process for the preparation of an ophthalmic formulation comprises subjecting the formulation to a sterilization method selected from heat sterilization, chemical sterilization, radiation sterilization or filtration sterilization. The method used depends largely upon the nature of the device or composition to be sterilized. Detailed descriptions of many methods of sterilization are given in Chapter 40 of Remington: The Science and Practice of Pharmacy published by Lippincott, Williams & Wilkins, and is incorporated by reference with respect to this subject matter.

Filtration

Filtration sterilization is a method used to remove but not destroy microorganisms from solutions. Membrane filters are used to filter heat-sensitive solutions. Such filters are thin, strong, homogenous polymers of mixed cellulosic esters (MCE), polyvinylidene fluoride (PVF; also known as PVDF), or polytetrafluoroethylene (PTFE) and have pore sizes ranging from 0.1 to 0.22 µm. Solutions of various characteristics are optionally filtered using different filter membranes. For example, PVF and PTFE membranes are well suited to filtering organic solvents while aqueous solutions are filtered through PVF or MCE membranes. Filter apparatus are available for use on many scales ranging from the single point-of-use disposable filter attached to a syringe up to commercial scale filters for use in manufacturing plants. The membrane filters are sterilized by autoclave or chemical sterilization. Validation of membrane filtration systems is performed following standardized protocols (Microbiological Evaluation of Filters for Sterilizing Liquids, Vol 4, No. 3. Washington, D.C.: Health Industry Manufacturers Association, 1981) and involve challenging the membrane filter with a known quantity (ca. $10^7/cm^2$) of unusually small microorganisms, such as *Brevundimonas diminuta* (ATCC 19146).

Pharmaceutical compositions are optionally sterilized by passing through membrane filters. Formulations comprising nanoparticles (U.S. Pat. No. 6,139,870) or multilamellar vesicles (Richard et al., International Journal of Pharmaceutics (2006), 312(1-2):144-50) are amenable to sterilization by filtration through 0.22 µm filters without destroying their organized structure.

In some embodiments, the methods disclosed herein comprise sterilizing the formulation (or components thereof) by means of filtration sterilization. In ophthalmic gel compositions that includes thermosetting polymers, filtration is carried out below (e.g. about 5° C.) the gel temperature (Tgel) of a formulation described herein and with viscosity that allows for filtration in a reasonable time using a peristaltic pump (e.g. below a theoretical value of 100 cP).

Accordingly, provided herein are methods for sterilization of ophthalmic formulations that prevent degradation of polymeric components (e.g., thermosetting and/or other viscosity enhancing agents) and/or the ophthalmic agent during the process of sterilization. In some embodiments, degradation of the ophthalmic agent (e.g., a muscarinic antagonist such as atropine or atropine sulfate) is reduced or eliminated through the use of specific pD ranges for buffer components and specific proportions of viscosity enhancing agents in the formulations. In some embodiments, the choice of an appropriate viscosity enhancing agents or thermosetting polymer allows for sterilization of formulations described herein by filtration. In some embodiments, the use of an appropriate thermosetting polymer or other viscosity enhancing agents in combination with a specific pD range for the formulation allows for high temperature sterilization of formulations described with substantially no degradation of the therapeutic agent or the polymeric excipients. An advantage of the methods of sterilization provided herein is that, in certain instances, the formulations are subjected to terminal sterilization via autoclaving without any loss of the ophthalmic agent and/or excipients and/or viscosity enhancing agents during the sterilization step and are rendered substantially free of microbes and/or pyrogens.

Radiation Sterilization

One advantage of radiation sterilization is the ability to sterilize many types of products without heat degradation or other damage. The radiation commonly employed is beta radiation or alternatively, gamma radiation from a $^{60}$Co source. The penetrating ability of gamma radiation allows its use in the sterilization of many product types, including solutions, compositions and heterogeneous mixtures. The germicidal effects of irradiation arise from the interaction of gamma radiation with biological macromolecules. This interaction generates charged species and free-radicals. Subsequent chemical reactions, such as rearrangements and cross-linking processes, result in the loss of normal function for these biological macromolecules. The formulations described herein are also optionally sterilized using beta irradiation.

Sterilization by Heat

Many methods are available for sterilization by the application of high heat. One method is through the use of a saturated steam autoclave. In this method, saturated steam at a temperature of at least 121° C. is allowed to contact the object to be sterilized. The transfer of heat is either directly to the microorganism, in the case of an object to be sterilized, or indirectly to the microorganism by heating the bulk of an aqueous solution to be sterilized. This method is widely practiced as it allows flexibility, safety and economy in the sterilization process.

Microorganisms

In some embodiments, the compositions are substantially free of microorganisms. Acceptable bioburden or sterility levels are based on applicable standards that define therapeutically acceptable compositions, including but not limited to United States Pharmacopeia Chapters <1111> et seq. For example, acceptable sterility (e.g., bioburden) levels include about 10 colony forming units (cfu) per gram of formulation, about 50 cfu per gram of formulation, about 100 cfu per gram of formulation, about 500 cfu per gram of formulation or about 1000 cfu per gram of formulation. In some embodiments, acceptable bioburden levels or sterility for formulations include less than 10 cfu/mL, less than 50 cfu/mL, less than 500 cfu/mL or less than 1000 cfu/mL microbial agents. In addition, acceptable bioburden levels or sterility include the exclusion of specified objectionable microbiological agents. By way of example, specified objectionable microbiological agents include but are not limited to *Escherichia coli* (*E. coli*), *Salmonella* sp., *Pseudomonas aeruginosa* (*P. aeruginosa*) and/or other specific microbial agents.

An important component of the sterility assurance quality control, quality assurance and validation process is the method of sterility testing. Sterility testing, by way of example only, is performed by two methods. The first is direct inoculation wherein a sample of the composition to be tested is added to growth medium and incubated for a period of time up to 21 days. Turbidity of the growth medium indicates contamination. Drawbacks to this method include the small sampling size of bulk materials which reduces sensitivity, and detection of microorganism growth based on a visual observation. An alternative method is membrane filtration sterility testing. In this method, a volume of product is passed through a small membrane filter paper. The filter paper is then placed into media to promote the growth of microorganisms. This method has the advantage of greater sensitivity as the entire bulk product is sampled. The commercially available Millipore Steritest sterility testing system is optionally used for determinations by membrane filtration sterility testing. For the filtration testing of creams or ointments Steritest filter system No. TLHVSL210 are used. For the filtration testing of emulsions or viscous products Steritest filter system No. TLAREM210 or TDAREM210 are used. For the filtration testing of pre-filled syringes Steritest filter system No. TTHASY210 are used. For the filtration testing of material dispensed as an aerosol or foam Steritest filter system No. TTHVA210 are used. For the filtration testing of soluble powders in ampoules or vials Steritest filter system No. TTHADA210 or TTHADV210 are used.

Testing for *E. coli* and *Salmonella* includes the use of lactose broths incubated at 30-35° C. for 24-72 hours, incubation in MacConkey and/or EMB agars for 18-24 hours, and/or the use of Rappaport medium. Testing for the detection of *P. aeruginosa* includes the use of NAC agar. United States Pharmacopeia Chapter <62> further enumerates testing procedures for specified objectionable microorganisms.

In certain embodiments, the ophthalmic formulation described herein has less than about 60 colony forming units (CFU), less than about 50 colony forming units, less than about 40 colony forming units, or less than about 30 colony forming units of microbial agents per gram of formulation. In certain embodiments, the ophthalmic formulations described herein are formulated to be isotonic with the eye.

Endotoxins

An additional aspect of the sterilization process is the removal of by-products from the killing of microorganisms (hereinafter, "Product"). The process of depyrogenation removes pyrogens from the sample. Pyrogens are endotoxins or exotoxins which induce an immune response. An example of an endotoxin is the lipopolysaccharide (LPS) molecule found in the cell wall of gram-negative bacteria. While sterilization procedures such as autoclaving or treatment with ethylene oxide kill the bacteria, the LPS residue induces a proinflammatory immune response, such as septic shock. Because the molecular size of endotoxins varies widely, the presence of endotoxins is expressed in "endotoxin units" (EU). One EU is equivalent to 100 picograms of *E. coli* LPS. In some cases, humans develop a response to as little as 5 EU/kg of body weight. The bioburden (e.g., microbial limit) and/or sterility (e.g., endotoxin level) is expressed in any units as recognized in the art. In certain embodiments, ophthalmic compositions described herein contain lower endotoxin levels (e.g. <4 EU/kg of body weight of a subject) when compared to conventionally acceptable endotoxin levels (e.g., 5 EU/kg of body weight of a subject). In some embodiments, the ophthalmic formulation has less than about 5 EU/kg of body weight of a subject. In other embodiments, the ophthalmic formulation has less than about 4 EU/kg of body weight of a subject. In additional embodiments, the ophthalmic formulation has less than about 3 EU/kg of body weight of a subject. In additional embodiments, the ophthalmic formulation has less than about 2 EU/kg of body weight of a subject.

In some embodiments, the ophthalmic formulation has less than about 5 EU/kg of formulation. In other embodiments, the ophthalmic formulation has less than about 4 EU/kg of formulation. In additional embodiments, the ophthalmic formulation has less than about 3 EU/kg of formulation. In some embodiments, the ophthalmic formulation has less than about 5 EU/kg Product. In other embodiments, the ophthalmic formulation has less than about 1 EU/kg Product. In additional embodiments, the ophthalmic formulation has less than about 0.2 EU/kg Product. In some embodiments, the ophthalmic formulation has less than about 5 EU/g of unit or Product. In other embodiments, the ophthalmic formulation has less than about 4 EU/g of unit or Product. In additional embodiments, the ophthalmic formulation has less than about 3 EU/g of unit or Product. In some embodiments, the ophthalmic formulation has less than about 5 EU/mg of unit or Product. In other embodiments, the ophthalmic formulation has less than about 4 EU/mg of unit or Product. In additional embodiments, the ophthalmic formulation has less than about 3 EU/mg of unit or Product. In certain embodiments, ophthalmic formulations described herein contain from about 1 to about 5 EU/mL of formulation. In certain embodiments, ophthalmic formulations described herein contain from about 2 to about 5 EU/mL of formulation, from about 3 to about 5 EU/mL of formulation, or from about 4 to about 5 EU/mL of formulation.

In certain embodiments, ophthalmic compositions described herein contain lower endotoxin levels (e.g. <0.5 EU/mL of formulation) when compared to conventionally acceptable endotoxin levels (e.g., 0.5 EU/mL of formulation). In some embodiments, the ophthalmic formulation has less than about 0.5 EU/mL of formulation. In other embodiments, the ophthalmic formulation has less than about 0.4

EU/mL of formulation. In additional embodiments, the ophthalmic formulation has less than about 0.2 EU/mL of formulation.

Pyrogen detection, by way of example only, is performed by several methods. Suitable tests for sterility include tests described in United States Pharmacopoeia (USP)<71> Sterility Tests (23rd edition, 1995). The rabbit pyrogen test and the Limulus amebocyte lysate test are both specified in the United States Pharmacopeia Chapters <85> and <151> (USP23/NF 18, Biological Tests, The United States Pharmacopeial Convention, Rockville, Md., 1995). Alternative pyrogen assays have been developed based upon the monocyte activation-cytokine assay. Uniform cell lines suitable for quality control applications have been developed and have demonstrated the ability to detect pyrogenicity in samples that have passed the rabbit pyrogen test and the Limulus amebocyte lysate test (Taktak et al, J. Pharm. Pharmacol. (1990), 43:578-82). In an additional embodiment, the ophthalmic formulation is subject to depyrogenation. In a further embodiment, the process for the manufacture of the ophthalmic formulation comprises testing the formulation for pyrogenicity. In certain embodiments, the formulations described herein are substantially free of pyrogens.

Ophthalmic Muscarinic Antagonist-Mucus Penetrating Particle (MPP) Composition

Mucus-penetrating particles (MPPs) are particles that rapidly traverse mucus (e.g. human mucus). In some cases, MPPs comprise of a nanoparticle with a particle size of between about 200 nm and 500 nm. In some instances, the nanoparticle is further coated with a mucus penetrating agent. In some instances, a composition described herein is formulated with MPPs for mucus penetration. In some instances, an ophthalmic agent composition described herein is formulated with MPPs for mucus penetration. In some instances, the ophthalmic agent is a muscarinic antagonist. In some instances, a muscarinic antagonist composition described herein is formulated with MPPs for mucus penetration. In some instances, a muscarinic antagonist comprises atropine, atropine sulfate, noratropine, atropine-N-oxide, tropine, tropic acid, atropine methonitrate, diphenhydramine, dimenhydrinate, dicyclomine, flavoxate, oxybutynin, tiotropium, hyoscine, scopolomine (L-hyoscine), hydroxyzine, ipratropium, tropicamide, cyclopentolate, pirenzapine, homatropine, solifenacin, darifenacin, benzatropine, mebeverine, procyclidine, aclidinium bromide, trihexyphenidyl/benzhexol, or tolterodine. In some instances, a muscarinic antagonist is atropine or its pharmaceutically acceptable salt thereof. In some instances, a muscarinic antagonist is atropine sulfate. In some instances, an atropine composition described herein is formulated with MPPs for mucus penetration. In some instances, an atropine sulfate composition described herein is formulated with MPPs for mucus penetration. In a non-limiting example, the MMPs for use in the disclosed composition is obtained from Kala Pharmaceuticals, Inc. (100 Beaver Street #201, Waltham, Mass. 02453).

In some embodiments, the nanoparticle comprises of any suitable material, such as an organic material, an inorganic material, a polymer, or combinations thereof. In some instances, the nanoparticle comprises of inorganic material, such as for example, a metal (e.g., Ag, Au, Pt, Fe, Cr, Co, Ni, Cu, Zn, and other transition metals), a semiconductor (e.g., silicon, silicon compounds and alloys, cadmium selenide, cadmium sulfide, indium arsenide, and indium phosphide), or an insulator (e.g., ceramics such as silicon oxide). In some instances, the nanoparticle comprises organic materials such as a synthetic polymer and/or a natural polymer. Examples of synthetic polymers include non-degradable polymers such as polymethacrylate and degradable polymers such as polylactic acid, polyglycolic acid and copolymers thereof. Examples of natural polymers include hyaluronic acid, chitosan, and collagen.

In some embodiments, the nanoparticle is coated with a mucus penetrating agent. In some instances, the mucus penetrating agent comprises any suitable material, such as a hydrophobic material, a hydrophilic material, and/or an amphiphilic material. In some instances, the mucus penetrating agent is a polymer. In some instances, the polymer a synthetic polymer (i.e., a polymer not produced in nature). In other embodiments, the polymer is a natural polymer (e.g., a protein, polysaccharide, rubber). In certain embodiments, the polymer is a surface active polymer. In certain embodiments, the polymer is a non-ionic polymer. In certain embodiments, the polymer is a non-ionic block copolymer. In some embodiments, the polymer is a diblock copolymer, a triblock copolymer, e.g., e.g., where one block is a hydrophobic polymer and another block is a hydrophilic polymer. In some embodiments, the polymer is charged or uncharged.

Additional examples of suitable polymers include, but are not limited to, polyamines, polyethers, polyamides, polyesters, polycarbamates, polyureas, polycarbonates, polystyrenes, polyimides, polysulfones, polyurethanes, polyacetylenes, polyethylenes, polyethyeneimines, polyisocyanates, polyacrylates, polymethacrylates, polyacrylonitriles, and polyarylates. Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), poly(ethylene glycol), poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) (jointly referred to herein as "polyacrylic acids"), and copolymers and mixtures thereof, polydioxanone and its copolymers, polyhydroxyalkanoates, polypropylene fumarate), polyoxymethylene, poloxamers, poly(ortho)esters, poly(butyric acid), poly(valeric acid), poly(lactide-co-caprolactone), and trimethylene carbonate, polyvinylpyrrolidone.

In some cases, an ophthalmic agent (e.g. a muscarinic antagonist such as atropine or atropine sulfate) is present in the MPP formulation at a concentration of between about 0.001 wt % and about 0.05 wt %, between about 0.005% to about 0.050%, between about 0.010% to about 0.050%, between about 0.015% to about 0.050%, between about 0.020% to about 0.050%, between about 0.025% to about 0.050%, between about 0.030% to about 0.050%, between about 0.035% to about 0.050%, between about 0.040% to about 0.050%, or between about 0.045% to about 0.050% of the ophthalmic agent, or pharmaceutically acceptable prodrug or salt thereof, by weight of the composition. In some instances, additional agents such as buffers, pD adjusting agents, and/or preservatives are formulated in the MPP formulation.

In some instances, ophthalmic agent-MPP composition is formulated using any suitable method. In some embodiments, a milling process is used to reduce the size of a solid material to form particles in the micrometer to nanometer size range. In some cases, dry and wet milling processes such as jet milling, cryo-milling, ball milling, media milling, and homogenization are known and are used in methods described herein. Generally, in a wet milling process, a suspension of the material to be used as the nanoparticle is mixed with milling media with or without excipients to reduce particle size. Dry milling is a process wherein the material to be used as the nanoparticle is mixed with milling media with or without excipients to reduce particle size. In a cryo-milling process, a suspension of the material to be used as the nanoparticle is mixed with milling media with or without excipients under cooled temperatures.

In some embodiments, any suitable grinding medium is used for milling. In some embodiments, a ceramic and/or polymeric material and/or a metal is used. Examples of suitable materials include zirconium oxide, silicon carbide, silicon oxide, silicon nitride, zirconium silicate, yttrium oxide, glass, alumina, alpha-alumina, aluminum oxide, polystyrene, poly(methyl methacrylate), titanium, steel. In some cases, a grinding medium has any suitable size. For example, the grinding medium has an average diameter of at least about 0.1 mm, at least about 0.2 mm, at least about 0.5 mm, at least about 0.8 mm, at least about 1 mm, at least about 2 mm, or at least about 5 mm. In some cases, the grinding medium has an average diameter of less than or equal to about 5 mm, less than or equal to about 2 mm, less than or equal to about 1 mm, less than or equal to about 0.8, less than or equal to about 0.5 mm, or less than or equal to about 0.2 mm. Combinations of the above-referenced ranges are also possible (e.g., an average diameter of at least about 0.5 millimeters and less than or equal to about 1 mm). Other ranges are also possible.

In some embodiments, any suitable solvent are used for milling. In some cases, the choice of solvent is depend on factors such as the solid material (e.g., a muscarinic antagonist such as atropine) being milled, the particular type of stabilizer/mucus penetrating agent being used (e.g., one that renders the particle mucus penetrating), the grinding material be used, among other factors. In some cases, suitable solvents are ones that do not substantially dissolve the solid material or the grinding material, but dissolve the stabilizer/mucus penetrating agent to a suitable degree. Non-limiting examples of solvents include, but are not limited to, water, buffered solutions, other aqueous solutions, alcohols (e.g., ethanol, methanol, butanol), and mixtures thereof that optionally include other components such as pharmaceutical excipients, polymers, pharmaceutical agents, salts, preservative agents, viscosity modifiers, tonicity modifier, taste masking agents, antioxidants, pD modifier, and other pharmaceutical excipients. In other embodiments, an organic solvent is used. In some cases, a pharmaceutical agent (e.g. a muscarinic antagonist such as atropine) has any suitable solubility in these or other solvents, such as a solubility in one or more of the ranges described above for aqueous solubility or for solubility in a coating solution.

In some instances, a MPP is a MPP as described in WO2013/166385. In some instances, a MPP is a MPP as described in Lai et al., "Rapid transport of large polymeric nanoparticles in fresh undiluted human mucus," PNAS 104(5):1482-1487 (2007). In some instances, an ophthalmic agent-MPP composition is formulated using a method as described in WO2013/166385. In some instances, an ophthalmic agent-MPP composition is formulated using a method as described in Lai et al., "Rapid transport of large polymeric nanoparticles in fresh undiluted human mucus," PNAS 104(5):1482-1487 (2007). In some instances, the ophthalmic agent is a muscarinic antagonist such as atropine or atropine sulfate.

Ophthalmic Gel Muscarinic Antagonist Composition

Gels have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums, (e.g., tragacanth). In some embodiments, single-phase gels are generally aqueous, but will also be made using alcohols and oils. Two-phase gels consist of a network of small discrete particles.

In some embodiments, gels are also classified as being hydrophobic or hydrophilic. In certain embodiments, the base of a non-limiting example of a hydrophobic gel includes a liquid paraffin with polyethylene or fatty oils gelled with colloidal silica, or aluminum or zinc soaps. In contrast, the base of a non-limiting example of a hydrophilic gel includes water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the compositions disclosed herein is pseudo plastic, plastic, thixotropic, or dilatant.

In some embodiments, the ophthalmic composition is an ophthalmic gel, and wherein the ophthalmically acceptable carrier comprises water and at least one viscosity-enhancing agent. In some embodiments, the viscosity-enhancing agent is selected from cellulose-based polymers, polyoxyethylene-polyoxypropylene triblock copolymers, dextran-based polymers, polyvinyl alcohol, dextrin, polyvinylpyrrolidone, polyalkylene glycols, chitosan, collagen, gelatin, hyaluronic acid, or combinations thereof.

In some embodiment, the ophthalmic gel composition described herein is a semi-solid or id in a gelled state before it is topically administered (e.g. at room temperature). For example, suitable viscosity-enhancing agents for such gels include by way of example only, gelling agents and suspending agents. In one embodiment, the enhanced viscosity formulation does not include a buffer. In other embodiments, the enhanced viscosity formulation includes a pharmaceutically acceptable buffer. Sodium chloride or other tonicity agents are optionally used to adjust tonicity, if necessary.

By way of example only, the ophthalmically acceptable viscosity agent includes hydroxypropyl methylcellulose, hydroxyethyl cellulose, polyvinylpyrrolidone, carboxymethyl cellulose, polyvinyl alcohol, sodium chondroitin sulfate, sodium hyaluronate. Other viscosity enhancing agents compatible with the targeted ocular site include, but are not limited to, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethylcellulose (HPMC), sodium carboxymethyl-cellulose (CMC), silicon dioxide, polyvinylpyrrolidone (PVP: povidone), Splenda® (dextrose, maltodextrin and sucralose) or combinations thereof. In specific embodiments, the viscosity-enhancing excipient is a combination of MCC and CMC. In another embodiment, the viscosity-enhancing agent is a combination of carboxymethylated chitosan, or chitin, and alginate. The combination of chitin and alginate with the ophthalmic agents disclosed herein acts as a controlled release formulation, restricting the diffusion of the ophthalmic agents from the formulation. Moreover, the combination of carboxymethylated chitosan and alginate is optionally used to assist in increasing the permeability of the ophthalmic agents in the eye.

In some embodiments is an enhanced viscosity formulation, comprising from about 0.1 mM and about 100 mM of an ophthalmic agent, a pharmaceutically acceptable viscosity agent, and water for injection, the concentration of the viscosity agent in the water being sufficient to provide an enhanced viscosity formulation with a final viscosity from about 100 to about 100,000 cP. In certain embodiments, the viscosity of the gel is in the range from about 100 to about 50,000 cP, about 100 cP to about 1,000 cP, about 500 cP to about 1500 cP, about 1000 cP to about 3000 cP, about 2000 cP to about 8,000 cP, about 4,000 cP to about 50,000 cP, about 10,000 cP to about 500,000 cP, about 15,000 cP to about 1,000,000 cP. In other embodiments, when an even more viscous medium is desired, the biocompatible gel comprises at least about 35%, at least about 45%, at least about 55%, at least about 65%, at least about 70%, at least about 75%, or even at least about 80% or so by weight of the ophthalmic agent. In highly concentrated samples, the biocompatible enhanced viscosity formulation comprises at least about 25%, at least about 35%, at least about 45%, at least about 55%, at least about 65%, at least about 75%, at least about 85%, at least about 90% or at least about 95% or more by weight of the ophthalmic agent.

In one embodiment, the pharmaceutically acceptable enhanced viscosity ophthalmically acceptable formulation comprises at least one ophthalmic agent and at least one gelling agent. Suitable gelling agents for use in preparation of the gel formulation include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum and any combinations or mixtures thereof. In some other embodiments, hydroxypropylmethylcellulose (Methocel®) is utilized as the gelling agent. In certain embodiments, the viscosity enhancing agents described herein are also utilized as the gelling agent for the gel formulations presented herein.

In some embodiments, the ophthalmic gel composition described herein is an in situ gel formulation. In some instances, the in situ gel formation is based on increased pre-corneal residence time of the ophthalmic composition which improves ocular bioavailability, corneal mucoadhesion, lysosomal interaction and ionic gelation, improved corneal absorption, thermal gelation, or a combination thereof. In some instances, the in situ gel formulation is activated by pH, temperature, ion, UV, or solvent exchange.

In some instances, the ophthalmic gel composition comprises a muscarinic antagonist and one or more gelling agents. In some instances, the gelling agent includes, but is not limited to, poloxamer (e.g. Poloxamer 407), tetronics, ethyl (hydroxyethyl) cellulose, cellulose acetate phthalate (CAP), carbopol (e.g. Carbopol 1342P NF, Carbopol 980 NF), alginates (e.g. low acetyl gellan gum (Gelrite®)), gellan, hyaluronic acid, pluronics (e.g. Pluronic F-127), chitosan, polyvinyl alcohol (PVA), polyvinylpyrrolidone (PVP), dextran, hydroxy propyl methyl cellulose (HPMC), hydroxyethylcellulose (HEC), methylcellulose (MC), thiolated xyloglucan, polymethacrilic acid (PMMA), polyethylene glycol (PEG), pseudolatexes, xyloglucans, or combinations thereof.

In some instances, the in situ gel formation further comprises a permeation enhancer. In some instances, the permeation enhancer includes surfactants (e.g. non-ionic surfactants), benzalkonium chloride, EDTA, surface-active heteroglycosides, calcium chelators, hydroxyl propyl beta cyclodextrin (HP beta CD), bile salts, and the like.

In some embodiments, other gel formulations are useful depending upon the particular ophthalmic agent, other pharmaceutical agent or excipients/additives used, and as such are considered to fall within the scope of the present disclosure. For example, other commercially-available glycerin-based gels, glycerin-derived compounds, conjugated, or crosslinked gels, matrices, hydrogels, and polymers, as well as gelatins and their derivatives, alginates, and alginate-based gels, and even various native and synthetic hydrogel and hydrogel-derived compounds are all expected to be useful in the ophthalmic agent formulations described herein. In some embodiments, ophthalmically acceptable gels include, but are not limited to, alginate hydrogels SAF®-Gel (ConvaTec, Princeton, N.J.), Duoderm® Hydroactive Gel (ConvaTec), Nu-gel® (Johnson & Johnson Medical, Arlington, Tex.); Carrasyn® (V) Acemannan Hydrogel (Carrington Laboratories, Inc., Irving, Tex.); glycerin gels Elta® Hydrogel (Swiss-American Products, Inc., Dallas, Tex.) and K-Y® Sterile (Johnson & Johnson). In further embodiments, biodegradable biocompatible gels also represent compounds present in ophthalmically acceptable formulations disclosed and described herein.

In some embodiments, the viscosity-enhancing agent is a cellulose-based polymer selected from cellulose gum, alkylcellulose, hydroxy-alkyl cellulose, hydroxyl-alkyl alkylcellulose, carboxy-alkyl cellulose, or combinations thereof. In some embodiments, the viscosity-enhancing agent is hydroxyl-alkyl alkylcellulose. In some embodiment, the viscosity-enhancing agent is hydroxypropyl methylcellulose.

In certain embodiments, the enhanced viscosity formulation is characterized by a phase transition between room temperature and body temperature (including an individual with a serious fever, e.g., up to about 42° C.). In some embodiments, the phase transition occurs at 1° C. below body temperature, at 2° C. below body temperature, at 3° C. below body temperature, at 4° C. below body temperature, at 6° C. below body temperature, at 8° C. below body temperature, or at 10° C. below body temperature. In some embodiments, the phase transition occurs at about 15° C. below body temperature, at about 20° C. below body temperature or at about 25° C. below body temperature. In specific embodiments, the gelation temperature (Tgel) of a formulation described herein is about 20° C., about 25° C., or about 30° C. In certain embodiments, the gelation temperature (Tgel) of a formulation described herein is about 35° C., or about 40° C. Included within the definition of body temperature is the body temperature of a healthy individual, or an unhealthy individual, including an individual with a fever (up to ~42° C.). In some embodiments, the pharmaceutical compositions described herein are liquids at about room temperature and are administered at or about room temperature.

Copolymers polyoxypropylene and polyoxyethylene (e.g. polyoxyethylene-polyoxypropylene triblock copolymers) form thermosetting gels when incorporated into aqueous solutions. These polymers have the ability to change from the liquid state to the gel state at temperatures close to body temperature, therefore allowing useful formulations that are applied to the targeted ocular site. The liquid state-to-gel state phase transition is dependent on the polymer concentration and the ingredients in the solution.

In some embodiments, the amount of thermosetting polymer in any formulation described herein is about 10%, about 15%, about 20%, about 25%, about 30%, about 35% or about 40% of the total weight of the formulation. In some embodiments, the amount of thermosetting polymer in any formulation described herein is about 10%, about 11%, about 12%, about 13%, about 14%, about 15%, about 16%, about 17%, about 18%, about 19%, about 20%, about 21%, about 22%, about 23%, about 24% or about 25% of the total weight of the formulation. In some embodiments, the amount of thermosetting polymer (e.g., Poloxamer 407) in any formulation described herein is about 7.5% of the total weight of the formulation. In some embodiments, the amount of thermosetting polymer (e.g., Poloxamer 407) in any formulation described herein is about 10% of the total weight of the formulation. In some embodiments, the amount of thermosetting polymer (e.g., Poloxamer 407) in any formulation described herein is about 11% of the total weight of the formulation. In some embodiments, the amount of thermosetting polymer (e.g., Poloxamer 407) in any formulation described herein is about 12% of the total weight of the formulation. In some embodiments, the amount of thermosetting polymer (e.g., Poloxamer 407) in any formulation described herein is about 13% of the total weight of the formulation. In some embodiments, the amount of thermosetting polymer (e.g., Poloxamer 407) in any formulation described herein is about 14% of the total weight of the formulation. In some embodiments, the amount of thermosetting polymer (e.g., Poloxamer 407) in any formulation described herein is about 15% of the total weight of the formulation. In some embodiments, the amount of thermosetting polymer (e.g., Poloxamer 407) in any formulation described herein is about 16% of the total weight of the formulation. In some embodiments, the amount of thermosetting polymer (e.g., Poloxamer 407) in any formulation described herein is about 17% of the total weight of the formulation. In some embodiments, the amount of thermosetting polymer (e.g., Poloxamer 407) in any formulation described herein is about 18% of the total weight of the formulation. In some embodiments, the amount of thermosetting polymer (e.g., Poloxamer 407) in any formulation described herein is about 19% of the total weight of the formulation. In some embodiments, the amount of thermosetting polymer (e.g., Poloxamer 407) in any formulation described herein is about 20% of the total weight of the formulation. In some embodiments, the amount of thermosetting polymer (e.g., Poloxamer 407) in any formulation described herein is about 21% of the total weight of the formulation. In some embodiments, the amount of thermosetting polymer (e.g., Poloxamer 407) in any formulation described herein is about 23% of the total weight of the formulation. In some embodiments, the amount of thermosetting polymer (e.g., Poloxamer 407) in any formulation described herein is about 25% of the total weight of the formulation. In some embodiments, the amount of thickening agent (e.g., a gelling agent) in any formulation described herein is about 1%, about 5%, about 10%, or about 15% of the total weight of the formulation. In some embodiments, the amount of thickening agent (e.g., a gelling agent) in any formulation described herein is about 0.5%, about 1%, about 1.5%, about 2%, about 2.5%, about 3%, about 3.5%, about 4%, about 4.5%, or about 5% of the total weight of the formulation.

In an alternative embodiment, the thermogel is a PEG-PLGA-PEG triblock copolymer (Jeong et al, Nature (1997), 388:860-2; Jeong et al, J. Control. Release (2000), 63:155-63; Jeong et al, Adv. Drug Delivery Rev. (2002), 54:37-51). The polymer exhibits sol-gel behavior over a concentration of about 5% w/w to about 40% w/w. Depending on the properties desired, the lactide/glycolide molar ratio in the PLGA copolymer ranges from about 1:1 to about 20:1. The resulting copolymers are soluble in water and form a free-flowing liquid at room temperature, but form a hydrogel at body temperature. A commercially available PEG-PLGA-PEG triblock copolymer is RESOMER RGP t50106 manufactured by Boehringer Ingelheim. This material is composed of a PLGA copolymer of 50:50 poly(DL-lactide-co-glycolide) and is 10% w/w of PEG and has a molecular weight of about 6000.

Additional biodegradable thermoplastic polyesters include AtriGel® (provided by Atrix Laboratories, Inc.) and/or those disclosed, e.g., in U.S. Pat. Nos. 5,324,519; 4,938,763; 5,702,716; 5,744,153; and 5,990,194; wherein the suitable biodegradable thermoplastic polyester is disclosed as a thermoplastic polymer. Examples of suitable biodegradable thermoplastic polyesters include polylactides, polyglycolides, polycaprolactones, copolymers thereof, terpolymers thereof, and any combinations thereof. In some such embodiments, the suitable biodegradable thermoplastic polyester is a polylactide, a polyglycolide, a copolymer thereof, a terpolymer thereof, or a combination thereof. In one embodiment, the biodegradable thermoplastic polyester is 50/50 poly(DL-lactide-co-glycolide) having a carboxy terminal group; is present in about 30 wt. % to about 40 wt. % of the composition; and has an average molecular weight of about 23,000 to about 45,000. Alternatively, in another embodiment, the biodegradable thermoplastic polyester is 75/25 poly (DL-lactide-co-glycolide) without a carboxy terminal group; is present in about 40 wt. % to about 50 wt.

% of the composition; and has an average molecular weight of about 15,000 to about 24,000. In further or alternative embodiments, the terminal groups of the poly(DL-lactide-co-glycolide) are either hydroxyl, carboxyl, or ester depending upon the method of polymerization. Polycondensation of lactic or glycolic acid provides a polymer with terminal hydroxyl and carboxyl groups. Ring-opening polymerization of the cyclic lactide or glycolide monomers with water, lactic acid, or glycolic acid provides polymers with the same terminal groups. However, ring-opening of the cyclic monomers with a monofunctional alcohol such as methanol, ethanol, or 1-dodecanol provides a polymer with one hydroxyl group and one ester terminal groups. Ring-opening polymerization of the cyclic monomers with a diol such as 1,6-hexanediol or polyethylene glycol provides a polymer with only hydroxyl terminal groups.

Since the polymer systems of thermosetting gels dissolve more completely at reduced temperatures, methods of solubilization include adding the required amount of polymer to the amount of water to be used at reduced temperatures. Generally after wetting the polymer by shaking, the mixture is capped and placed in a cold chamber or in a thermostatic container at about 0-10° C. in order to dissolve the polymer. The mixture is stirred or shaken to bring about a more rapid dissolution of the thermosetting gel polymer. The ophthalmic agent and various additives such as buffers, salts, and preservatives are subsequently added and dissolved. In some instances the pharmaceutically agent is suspended if it is insoluble in water. The pD is modulated by the addition of appropriate buffering agents.

Ophthalmic Ointment Muscarinic Antagonist Composition

An ointment is a homogeneous, viscous, semi-solid preparation, most commonly a greasy, thick oil (e.g. oil 80%-water 20%) with a high viscosity, intended for external application to the skin or mucous membranes. Ointments have a water number that defines the maximum amount of water that it contains. They are used as emollients or for the application of active ingredients to the skin for protective, therapeutic, or prophylactic purposes and where a degree of occlusion is desired. Ointments are used topically on a variety of body surfaces. These include the skin and the mucous membranes of the eye (an eye ointment), vulva, anus, and nose The vehicle of an ointment is known as the ointment base. The choice of a base depends upon the clinical indication for the ointment. The different types of ointment bases are: hydrocarbon bases, e.g. hard paraffin, soft paraffin, microcrystalline wax and ceresine; absorption bases, e.g. wool fat, beeswax; water soluble bases, e.g. macrogols 200, 300, 400; emulsifying bases, e.g. emulsifying wax, cetrimide; vegetable oils, e.g. olive oil, coconut oil, sesame oil, almond oil and peanut oil.

Ointments are formulated using hydrophobic, hydrophilic, or water-emulsifying bases to provide preparations that are immiscible, miscible, or emulsifiable with skin secretions. In some embodiments, they are also derived from hydrocarbon (fatty), absorption, water-removable, or water-soluble bases. The active agents are dispersed in the base, and later they get divided after the drug penetration into the target sites (e.g. membranes, skins, etc.).

The present disclosure recognizes that it is sometimes difficult to incorporate into the ointment a drug of low concentration with sufficient dose-to-dose uniformity for effectively treating a disorder or disease. In some embodiments, poly(ethylene-glycols), polyethoxylated castor oils (Cremophor® EL), alcohols having 12 to 20 carbon atoms or a mixture of two or more of said components are effective excipients for dispersing and/or dissolving effective amounts of ophthalmic drugs, in particular of ascomycins and staurosporine derivatives, in an ointment base, in particular in an ointment base substantially comprising oleaginous and hydrocarbon components, and that the resulting ointments are excellently tolerated by the skin and by ocular tissue.

The present disclosure further recognizes that ophthalmic drugs, such as a muscarinic antagonist (e.g. atropine or its pharmaceutically acceptable salts), incorporated in the ointment compositions describes herein target the choroid and/or retina in a patient when the compositions are topically administered to the ocular surface, in particular to the sclera of said patient. In some embodiments, an ophthalmic ointment composition includes an ophthalmic drug, an ointment base and an agent for dispersing and/or dissolving said drug in the ointment base, selected from a poly(ethylene-glycol), a polyethoxylated castor oil, an alcohol having 12 to 20 carbon atoms and a mixture of two or more of said components.

In some embodiments, the ointment bases include ophthalmically acceptable oil and fat bases, such as natural wax e.g. white and yellow bees wax, carnauba wax, wool wax (wool fat), purified lanolin, anhydrous lanolin; petroleum wax e.g. hard paraffin, microcrystalline wax; hydrocarbons e.g. liquid paraffin, white and yellow soft paraffin, white petrolatum, yellow petrolatum; or combinations thereof.

The above mentioned oil and fat bases are described in more detail, for instance, in the British Pharmacopoeia, Edition 2001, or the European Pharmacopoeia, 3rd Edition.

In some embodiments, the ointment base is present in amounts of about 50 to about 95, preferably of 70 to 90% by weight based on the total weight of the composition.

A preferred ointment base comprises a combination of one or more of one or more natural waxes like those indicated above, preferably wool wax (wool fat), and one or more hydrocarbons like those indicated above, preferably a soft paraffin or a petrolatum, more preferably in combination with liquid paraffin.

A special embodiment of the aforementioned ointment base comprises e.g. 5 to 17 parts by weight of wool fat, and 50 to 65 parts by weight of white petrolatum as well as 20 to 30 parts by weight of liquid paraffin.

In some embodiments, the agent for dispersing and/or dissolving the ophthalmic drug in the ointment base is selected from a poly(ethylene-glycol), a polyethoxylated castor oil, an alcohol having 12 to 20 carbon atoms and a mixture of two or more of said components. The agent is preferably used in amounts of 1 to 20 percent, more preferably 1 to 10 percent by weight of the entire semisolid ophthalmic composition.

Alcohols having 12 to 20 carbon atoms include particularly stearyl alcohol ($C_{18}H_{37}OH$), cetyl alcohol ($C_{16}H_{33}OH$) and mixtures thereof. Preferred are so-called cetostearyl alcohols, mixtures of solid alcohols substantially consisting of stearyl and cetyl alcohol and preferably comprising not less than 40 percent by weight of stearyl alcohol and a sum of stearyl alcohol and cetyl alcohol amounting to at least 90 percent by weight, and compositions comprising not less than 80 percent by weight of cetylstearyl alcohol and an emulsifier, in particular sodium cetostearyl sulfate and/or sodium lauryl sulfate, preferably in amounts not less than 7 percent by weight of emulsifier.

Polyethoxylated castor oils are reaction products of natural or hydrogenated castor oils and ethylene glycol. In some instances, such products are obtained in known manner, e.g.

by reaction of a natural or hydrogenated castor oil or fractions thereof with ethylene oxide, e.g. in a molar ratio of from about 1:30 to about 1:60, with optional removal of free polyethylene glycol components from the product, e.g. in accordance with the methods disclosed in German Auslegeschriften 1,182,388 and 1,518,819. Especially suitable and preferred is a product commercially available under the trade name Cremophor® EL having a molecular weight (by steam osmometry)=ca. 1630, a saponification no.=ca. 65-70, an acid no.=ca. 2, an iodine no.=ca. 28-32 and an nD 25=ca.1.471. Also suitable for use in this category is, for instance, Nikkol® HCO-60, a reaction product of hydrogenated castor oil and ethylene oxide exhibiting the following characteristics: acid no.=ca. 0.3; saponification no.=ca. 47.4; hydroxy value=ca. 42.5. pH (5%)=ca. 4.6; Color APHA=ca. 40; m.p.=ca. 36.0° C.; Freezing point=ca. 32.4° C.; $H_2O$ content (%, KF)=ca. 0.03.

Poly(ethylene-glycols) are used in some embodiments as the agent for dispersing and/or dissolving the ophthalmic drug in the ointment base according to the present disclosure. Suitable poly(ethylene-glycol)s are typically mixtures of polymeric compounds of the general formula H—(OCH2-CH2)nOH, wherein the index n typically range from 4 to 230 and the mean molecular weight from about 200 to about 10000. Preferably n is a number from about 6 to about 22 and the mean molecular weight between about 300 and about 1000, more preferably n ranges from about 6 to about 13 and the mean molecular weight from about 300 to about 600, most preferably n has a value of about 8.5 to about 9 and the relative molecular weight is about 400. Suitable poly(ethylene-glycols) are readily available commercially, for example poly(ethylene-glycols) having a mean molecular weight of about 200, 300, 400, 600, 1000, 1500, 2000, 3000, 4000, 6000, 8000 and 10000.

The poly(ethylene-glycols), in particular the preferred types described in the foregoing paragraph, are preferably used in amounts of 1 to 10, more preferably 1 to 5 percent by weight of the entire semisolid ophthalmic composition.

An especially preferred embodiment of the compositions according to the instant disclosure comprises an agent for dispersing and/or dissolving of the drug in the ointment base which is selected from a poly(ethylene-glycol), a polyethoxylated castor oil and preferably a mixture of said components.

Gel/Ointment Viscosity

In some embodiments, the composition has a Brookfield RVDV viscosity of from about 10,000 to about 300,000 cps at about 20° C. and sheer rate of $1\ s^{-1}$. In some embodiments, the composition has a Brookfield RVDV viscosity of from about 15,000 to about 200,000 cps at about 20° C. and sheer rate of $1\ s^{-1}$. In some embodiments, the composition has a Brookfield RVDV viscosity of from about 50,000 to about 150,000 cps at about 20° C. and sheer rate of $1\ s^{-1}$. In some embodiments, the composition has a Brookfield RVDV viscosity of from about 70,000 to about 130,000 cps at about 20° C. and sheer rate of $1\ s^{-1}$. In some embodiments, the composition has a Brookfield RVDV viscosity of from about 90,000 to about 110,000 cps at about 20° C. and sheer rate of $1\ s^{-1}$.

In some embodiments, the ophthalmic gel formulation contains a viscosity enhancing agent sufficient to provide a viscosity of between about 500 and 1,000,000 centipoise, between about 750 and 1,000,000 centipoise; between about 1000 and 1,000,000 centipoise; between about 1000 and 400,000 centipoise; between about 2000 and 100,000 centipoise; between about 3000 and 50,000 centipoise; between about 4000 and 25,000 centipoise; between about 5000 and 20,000 centipoise; or between about 6000 and 15,000 centipoise. In some embodiments, the ophthalmic gel formulation contains a viscosity enhancing agent sufficient to provide a viscosity of between about 50,0000 and 1,000,000 centipoise.

In some embodiments, the compositions described herein are low viscosity compositions at body temperature. In some embodiments, low viscosity compositions contain from about 1% to about 10% of a viscosity enhancing agent (e.g., gelling components such as polyoxyethylene-polyoxypropylene copolymers). In some embodiments, low viscosity compositions contain from about 2% to about 10% of a viscosity enhancing agent (e.g., gelling components such as polyoxyethylene-polyoxypropylene copolymers). In some embodiments, low viscosity compositions contain from about 5% to about 10% of a viscosity enhancing agent (e.g., gelling components such as polyoxyethylene-polyoxypropylene copolymers). In some embodiments, low viscosity compositions are substantially free of a viscosity enhancing agent (e.g., gelling components such as polyoxyethylene-polyoxypropylene copolymers). In some embodiments, a low viscosity ophthalmic agent composition described herein provides an apparent viscosity of from about 100 cP to about 10,000 cP. In some embodiments, a low viscosity ophthalmic agent composition described herein provides an apparent viscosity of from about 500 cP to about 10,000 cP. In some embodiments, a low viscosity ophthalmic agent composition described herein provides an apparent viscosity of from about 1000 cP to about 10,000 cP.

In some embodiments, the compositions described herein are viscous compositions at body temperature. In some embodiments, viscous compositions contain from about 10% to about 25% of a viscosity enhancing agent (e.g., gelling components such as polyoxyethylene-polyoxypropylene copolymers). In some embodiments, the viscous compositions contain from about 14% to about 22% of a viscosity enhancing agent (e.g., gelling components such as polyoxyethylene-polyoxypropylene copolymers). In some embodiments, the viscous compositions contain from about 15% to about 21% of a viscosity enhancing agent (e.g., gelling components such as polyoxyethylene-polyoxypropylene copolymers). In some embodiments, a viscous ophthalmic composition described herein provides an apparent viscosity of from about 100,000 cP to about 1,000,000 cP. In some embodiments, a viscous ophthalmic composition described herein provides an apparent viscosity of from about 150,000 cP to about 500,000 cP. In some embodiments, a viscous ophthalmic composition described herein provides an apparent viscosity of from about 250,000 cP to about 500,000 cP. In some of such embodiments, a viscous ophthalmic composition is a liquid at room temperature and gels at about between room temperature and body temperature (including an individual with a serious fever, e.g., up to about 42° C.). In some embodiments, a viscous ophthalmic composition is administered as monotherapy for treatment of an ophthalmic disease or condition described herein.

In some embodiments, the viscosity of the gel formulations presented herein is measured by any means described. For example, in some embodiments, an LVDV-II+CP Cone Plate Viscometer and a Cone Spindle CPE-40 is used to calculate the viscosity of the gel formulation described herein. In other embodiments, a Brookfield (spindle and cup) viscometer is used to calculate the viscosity of the gel formulation described herein. In some embodiments, the viscosity ranges referred to herein are measured at room temperature. In other embodiments, the viscosity ranges referred to herein are measured at body temperature (e.g., at the average body temperature of a healthy human).

Gel/Ointment Dose-to-Dose Uniformity

Typical ophthalmic gels are packaged in eye drop bottles and administered as drops. For example, a single administration (i.e. a single dose) of an ophthalmic gel includes a single drop, two drops, three drops or more into the eyes of the patient. Furthermore, typical ophthalmic ointments are packaged in tubes or other squeezable containers with a dispensing nozzle through which strips of the ointment are delivered. For example, a single administration (i.e. a single dose) of an ophthalmic ointment includes a single strip, or multiple strips into the eyes of the patient. In some embodiments, one dose of the ophthalmic gel described herein is one drop of the gel composition from the eye drop bottle. In some embodiments, one dose of the ophthalmic ointment is one strip of the ointment composition dispensed through the nozzle of a dispersing tube.

In some cases, described herein include ophthalmic gel compositions which provide a dose-to-dose uniform concentrations. In some instances, the dose-to-dose uniform concentration does not present significant variations of drug content from one dose to another. In some instances, the dose-to-dose uniform concentration does provide consistent drug content from one dose to another.

In some cases, described herein include ophthalmic ointment compositions which provide a dose-to-dose uniform concentrations. In some instances, the dose-to-dose uniform concentration does not present significant variations of drug content from one dose to another. In some instances, the dose-to-dose uniform concentration does provide consistent drug content from one dose to another.

In some embodiments, the composition has a dose-to-dose ophthalmic agent concentration variation of less than 50%. In some embodiments, the composition has a dose-to-dose ophthalmic agent concentration variation of less than 40%. In some embodiments, the composition has a dose-to-dose ophthalmic agent concentration variation of less than 30%. In some embodiments, the composition has a dose-to-dose ophthalmic agent concentration variation of less than 20%. In some embodiments, the composition has a dose-to-dose ophthalmic agent concentration variation of less than 10%. In some embodiments, the composition has a dose-to-dose ophthalmic agent concentration variation of less than 5%.

In some embodiments, the dose-to-dose ophthalmic agent concentration variation is based on 10 consecutive doses. In some embodiments, the dose-to-dose ophthalmic agent concentration variation is based on 8 consecutive doses. In some embodiments, the dose-to-dose ophthalmic agent concentration variation is based on 5 consecutive doses. In some embodiments, the dose-to-dose ophthalmic agent concentration variation is based on 3 consecutive doses. In some embodiments, the dose-to-dose ophthalmic agent concentration variation is based on 2 consecutive doses.

A nonsettling formulation should not require shaking to disperse drug uniformly. A "no-shake" formulation is potentially advantageous over formulations that require shaking for the simple reason that patients' shaking behavior is a major source of variability in the amount of drug dosed. It has been reported that patients often times do not or forget to shake their ophthalmic compositions that requires shaking before administering a dose, despite the instructions to shake that were clearly marked on the label. On the other hand, even for those patients who do shake the product, it is normally not possible to determine whether the shaking is adequate in intensity and/or duration to render the product uniform. In some embodiments, the ophthalmic gel compositions and ophthalmic ointment compositions described herein are "no-shake" formulations that maintained the dose-to-dose uniformity described herein.

To evaluate the dose-to-dose uniformity, drop bottles or tubes containing the ophthalmic aqueous compositions, the ophthalmic gel compositions, or ophthalmic ointment compositions are stored upright for a minimum of 12 hours prior to the start of the test. To simulate the recommended dosing of these products, predetermined number of drops or strips are dispensed from each commercial bottles or tubes at predetermined time intervals for an extended period of time or until no product was left in the bottle or tube. All drops and strips are dispensed into tared glass vials, capped, and stored at room temperature until analysis. Concentrations of a muscarinic antagonist such as atropine in the expressed drops were determined using a reverse-phase HPLC method.

Methods of Treatment

Disclosed herein are methods of arresting myopia development by administering to an eye of an individual in need thereof an effective amount of an ophthalmic composition as described above. Also disclosed herein are methods of preventing myopia development by administering to an eye of an individual in need thereof an effective amount of an ophthalmic composition as described above.

In some embodiments, the ophthalmic aqueous formulations described herein are packaged in eye drop bottles and administered as drops. For example, a single administration (i.e. a single dose) of an ophthalmic aqueous formulation includes a single drop, two drops, three drops or more into the eyes of the patient. In some embodiments, the ophthalmic gel formulations described herein are packaged in eye drop bottles and administered as drops. For example, a single administration (i.e. a single dose) of an ophthalmic gel includes a single drop, two drops, three drops or more into the eyes of the patient. In some embodiments, the ophthalmic ointment formulations described herein are packaged in tubes or other squeezable containers with a dispensing nozzle through which strips of the ointment are delivered. For example, a single administration (i.e. a single dose) of an ophthalmic ointment includes a single strip, or multiple strips into the eyes of the patient. In some embodiments, one dose of the ophthalmic aqueous formulation described herein is one drop of the aqueous composition from the eye drop bottle. In some embodiments, one dose of the ophthalmic gel described herein is one drop of the gel composition from the eye drop bottle. In some embodiments, one dose of the ophthalmic ointment is one strip of the ointment composition dispensed through the nozzle of a dispersing tube.

In some embodiments of the disclosed method, the ophthalmic composition is stored below room temperature prior to first use. In some embodiments of the disclosed method, the ophthalmic composition is stored at between about 2° C. to about 10° C. prior to first use. In some embodiments of the disclosed method, the ophthalmic composition is stored at about 2° C., about 3° C., about 4° C., about 5° C., about 6° C., about 7° C., about 8° C., about 9° C., or about 10° C. prior to first use. In some embodiments of the disclosed method, the ophthalmic composition is stored at between about 4° C. to about 8° C. prior to first use.

In some embodiments of the disclosed method, the ophthalmic composition is stored at room temperature after first use. In some embodiments of the disclosed method, the ophthalmic composition is stored at between about 16° C. to about 26° C. after to first use. In some embodiments of the disclosed method, the ophthalmic composition is stored at about 16° C., about 17° C., about 18° C., about 19° C., about 20° C., about 21° C., about 22° C., about 23° C., about 24° C., about 25° C., or about 26° C. after to first use.

In some embodiments, the ophthalmic aqueous formulations are administered as follows: the lower lid of the eye to be administered was pulled down and a predetermined amount of the aqueous formulation (e.g. 1-3 drops) is applied to the inside of the eyelid. The ophthalmic tip of the dispensing mechanism does not touch any surface to avoid contamination and/or injury.

In some embodiments, the ophthalmic gel formulations are administered as follows: the lower lid of the eye to be administered was pulled down and a predetermined amount of gel (e.g. 1-3 drops) is applied to the inside of the eyelid. The ophthalmic tip of the dispensing mechanism does not touch any surface to avoid contamination and/or injury.

In some embodiments, the ophthalmic ointment formulations are administered as follows: the lower lid of the eye to be administered was pulled down and a small amount of ointment (approximately 0.25 inches) was applied to the inside of the eyelid. The ophthalmic tip of the dispensing mechanism does not touch any surface to avoid contamination and/or injury.

In some embodiments, the ophthalmic composition is administered at predetermined time intervals over an extended period of time. In some embodiments, the ophthalmic composition is administered once every day. In some embodiments, the ophthalmic composition is administered every other day. In some embodiments, the ophthalmic composition is administered over 1 week, 2 weeks, 1 month, 2 months, 3 months, 6 moths, 1 year, 2 years, 3 years, 4 years, 5 years, 6 years, 7 years, 8 years, 9 years, 10 years, 11 years, or 12-15 years.

In some embodiments, the ophthalmic composition is administered in doses having a dose-to-dose ophthalmic agent concentration variation of less than 50%, less than 40%, less than 30%, less than 20%, less than 10%, or less than 5%.

The number of times a composition is administered to an individual in need thereof depends on the discretion of a medical professional, the disorder, the severity of the disorder, and the individual's response to the formulation. In some embodiments, a composition disclosed herein is administered once to an individual in need thereof with a mild acute condition. In some embodiments, a composition disclosed herein is administered more than once to an individual in need thereof with a moderate or severe acute condition. In the case wherein the patient's condition does not improve, upon the doctor's discretion the administration of an ophthalmic agent is administered chronically, that is, for an extended period of time, including throughout the duration of the patient's life in order to ameliorate or otherwise control or limit the symptoms of the patient's disease or condition.

In the case wherein the patient's condition does not improve, upon the doctor's discretion the administration of the ophthalmic agent is administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the ophthalmic agent is given continuously; alternatively, the dose of drug being administered is temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's ophthalmic conditions has occurred, a maintenance ophthalmic agent dose is administered if necessary. Subsequently, the dosage or the frequency of administration, or both, is optionally reduced, as a function of the symptoms, to a level at which the improved disease, disorder or condition is retained. In certain embodiments, patients require intermittent treatment on a long-term basis upon any recurrence of symptoms.

The amount of ophthalmic agent that will correspond to such an amount will vary depending upon factors such as the particular compound, disease condition and its severity, according to the particular circumstances surrounding the case, including, e.g., the specific ophthalmic agent being administered, the route of administration, the condition being treated, the target area being treated, and the subject or host being treated. The desired dose is presented in a single dose or as divided doses administered simultaneously (or over a short period of time) or at appropriate intervals.

In some embodiments, the initial administration is a particular ophthalmic agent and the subsequent administration a different formulation or ophthalmic agent.

Kits/Articles of Manufacture

The disclosure also provides kits for preventing or arresting myopia development. Such kits generally will comprise one or more of the ophthalmic compositions disclosed herein, and instructions for using the kit. The disclosure also contemplates the use of one or more of the ophthalmic compositions, in the manufacture of medicaments for treating, abating, reducing, or ameliorating the symptoms of a disease, dysfunction, or disorder in a mammal, such as a human that has, is suspected of having, or at risk for developing myopia.

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein contain packaging materials. Packaging materials for use in packaging pharmaceutical products are also presented herein. See, e.g., U.S. Pat. Nos. 5,323,907, 5,052,558 and 5,033,252. Examples of pharmaceutical packaging materials include, but are not limited to, drop bottles, tubes, pumps, bags, vials, containers, syringes, bottles, and any packaging material suitable for a selected formulation and intended mode of administration and treatment. A wide array of ophthalmic compositions provided herein are contemplated as are a variety of treatments for any disease, disorder, or condition that benefits by controlled release administration of an ophthalmic agent to the eye.

In some embodiments, a kit includes one or more additional containers, each with one or more of various materials (such as rinses, wipes, and/or devices) desirable from a commercial and user standpoint for use of a formulation described herein. Such materials also include labels listing contents and/or instructions for use and package inserts with instructions for use. A set of instructions is optionally included. In a further embodiment, a label is on or associated with the container. In yet a further embodiment, a label is on a container when letters, numbers or other characters forming the label are attached, molded or etched into the container itself; a label is associated with a container when it is present within a receptacle or carrier that also holds the container, e.g., as a package insert. In other embodiments a label is used to indicate that the contents are to be used for a specific therapeutic application. In yet another embodiment, a label also indicates directions for use of the contents, such as in the methods described herein.

In certain embodiments, the ophthalmic compositions are presented in a dispenser device which contains one or more unit dosage forms containing a compound provided herein. In a further embodiment, the dispenser device is accompanied by instructions for administration. In yet a further embodiment, the dispenser is also accompanied with a notice associated with the container in form prescribed by a governmental agency regulating the manufacture, use, or sale of pharmaceuticals, which notice is reflective of approval by the agency of the form of the drug for human or veterinary administration. In another embodiment, such notice, for example, is the labeling approved by the U.S. Food and Drug Administration for prescription drugs, or the approved product insert. In yet another embodiment, compositions containing a compound provided herein formulated in a compatible pharmaceutical carrier are also prepared, placed in an appropriate container, and labeled for treatment of an indicated condition.

EXAMPLES

Example 1—Ophthalmic Formulations

Exemplary compositions for preparation of ophthalmic formulations are described in Tables 1-8.

TABLE 1

Aqueous Solution Formulation (Atropine)

| Ingredient | Quantity (mg/g) | Concentration (wt %) |
|---|---|---|
| Atropine | 0.01-0.5 | 0.001-0.05 (wt %) |
| Buffer agent and/or pD adjusting agent (e.g., borates and/or DCl) | — | q.s. for pD = 4.2-7.9 |
| Preservative (e.g. benzalkonium chloride, cetrimonium sodium perborate, etc.) | — | q.s. to prevent the growth of or to destroy microorganism introduced into the solution |
| Tonicity and/or Osmolarity adjustor (e.g. NaCl, mannitol, etc) | — | q.s. to 0.5-2.0 wt % |
| Deuterated Water | — | q.s. to 100 wt % |

TABLE 2

Aqueous Solution Formulation (Atropine Sulfate)

| Ingredient | Quantity (mg/g) | Concentration (wt %) |
|---|---|---|
| Atropine sulfate | 0.01-0.5 | 0.001-0.05 (wt %) |
| Buffer agent and/or pD adjusting agent (e.g., borates and/or DCl) | — | q.s. for pD = 4.2-7.9 |
| Preservative (e.g. benzalkonium chloride, cetrimonium sodium perborate, etc.) | — | q.s. to prevent the growth of or to destroy microorganism introduced into the solution |
| Tonicity and/or Osmolarity adjustor (e.g. NaCl, mannitol, etc) | — | q.s. to 0.5-2.0 wt % |
| Deuterated Water | — | q.s. to 100 wt % |

TABLE 3

Aqueous Solution Formulation (Atropine Sulfate)

| Ingredient | Quantity (mg/g) | Concentration (wt %) |
|---|---|---|
| Atropine sulfate | 0.05-0.15 | 0.005-0.015 (wt %) |
| Buffer agent and/or pD adjusting agent (e.g., borates and/or DCl) | — | q.s. for pD = 4.2-7.9 |
| Preservative (e.g. benzalkonium chloride, cetrimonium sodium perborate, etc.) | — | q.s. to prevent the growth of or to destroy microorganism introduced into the solution |
| Tonicity and/or Osmolarity adjustor (e.g. NaCl, mannitol, etc) | — | q.s. to 0.5-2.0 wt % |
| Deuterated Water | — | q.s. to 100 wt % |

TABLE 4

Mucus Penetrating Particle Formulation (Atropine)

| Ingredient | Quantity (mg/g) | Concentration (wt %) |
|---|---|---|
| Atropine | 0.01-0.5 | 0.001-0.05 (wt %) |
| Buffer agent and/or pD adjusting agent (e.g., borates and/or DCl) | — | q.s. for pD = 4.2-7.9 |
| Preservative (e.g. benzalkonium chloride, cetrimonium sodium perborate, etc.) | — | q.s. to prevent the growth of or to destroy microorganism introduced into the solution |
| Mucus penetrating particles | — | q.s. to formulate atropine at 0.001-0.05 wt % |
| Deuterated Water | — | q.s. to 100 wt % |

TABLE 5

Mucus Penetrating Particle Formulation (Atropine Sulfate)

| Ingredient | Quantity (mg %) | Concentration (wt %) |
|---|---|---|
| Atropine sulfate | 0.01-0.5 | 0.001-0.05 (wt %) |
| Buffer agent and/or pD adjusting agent (e.g., borates and/or DCl) | — | q.s. for pD = 4.2-7.9 |
| Preservative (e.g. benzalkonium chloride, cetrimonium sodium perborate, etc.) | — | q.s. to prevent the growth of or to destroy microorganism introduced into the solution |

TABLE 5-continued

Mucus Penetrating Particle Formulation (Atropine Sulfate)

| Ingredient | Quantity (mg %) | Concentration (wt %) |
|---|---|---|
| Mucus penetrating particles | — | q.s. to formulate atropine at 0.001-0.05 wt % |
| Deuterated Water | — | q.s. to 100 wt % |

TABLE 6

Cellulose Gel Formulation (Atropine Sulfate)

| Ingredient | Quantity (mg/g) | Concentration (wt %) |
|---|---|---|
| Atropine Sulfate | 0.01-0.5 | 0.001-0.05 (wt %) |
| Viscosity enhancing agent (e.g. hydroxypropyl methylcellulose) | 10-50 | 1-5 (wt %) |
| Buffer agent and/or pD adjusting agent (e.g., sodium acetate and/or DCl) | — | q.s. for pD = 4.2-7.9 |
| Stabilizer (e.g. EDTA, cyclodextrin, etc.) | — | q.s. for low degradation of atropine sulfate (e.g. less than 10%, 5% or 1% degradation) |
| Osmolarity modifier (e.g. NaCl) | — | q.s. 150-500 mOsm/L |
| Deuterated Water | — | q.s. to 100 wt % |

TABLE 7

Thermosetting Gel Formulation (Atropine Sulfate)

| Ingredient | Quantity (mg/g) | Concentration (wt %) |
|---|---|---|
| Atropine sulfate | 0.01-0.5 | 0.001-0.05 (wt %) |
| Viscosity enhancing agent (e.g. poloxamer 407) | 100-250 | 10-25 (wt %) |
| Buffer agent and/or pD adjusting agent (e.g., sodium acetate and/or DCl) | — | q.s. for pH = 4.2-7.9 |
| Stabilizer (e.g. EDTA, cyclodextrin, etc.) | — | q.s. for low degradation of atropine sulfate (e.g. less than 10%, 5% or 1% degradation) |
| Osmolarity modifier (e.g. NaCl) | — | q.s. 150-500 mOsm/L |
| Deuterated Water | — | q.s. to 100 wt % |

TABLE 8

Ointment Formulation (Atropine Sulfate)

| Ingredient | Quantity (g) for 1000 mL solution | Concentration in 1000 mL aqueous solution |
|---|---|---|
| Atropine sulfate | 0.01-0.5 | 0.001-0.05 (wt %) |
| Dispersing agent (e.g. polyethyleneglycol, and/or polyethoxylated castor oil and/or C12-C20 alcohol | 10-200 | 1-20 (wt %) |
| Buffering agent pD adjusting agent (e.g. DCl) | — | q.s. for pD = 4.2-7.9 |
| Stabilizer (e.g. EDTA, cyclodextrin, etc.) | — | q.s. for low degradation of atropine sulfate (e.g. less than 10%, 5% or 1% degradation) |
| Osmolarity modifier (e.g. NaCl) | — | q.s. 150-500 mOsm/L |
| Ointment base (e.g. wool wax and/or petrolatum and/or liquid paraffin) | — | q.s. to 100 wt % |

Example 2—Preparation of an Aqueous Solution Formulation Containing 0.01% Atropine in $D_2O$ Stock 1% Solution In a 100 mL solution, 1 gram of atropine, and 0.77 g of NaCl (and other ingredients/components preferably in their dry state) are added along with a quantity sufficient to equal 100 mL sterile deuterated water for injection. The solution is mixed in an appropriately sized beaker with a stir bar on a hot plate until all of the solid powders have dissolved and the solution has become clear with no visible particles. Next, the stir bar is removed, and the solution is poured into a filter bottle and vacuum filtered through a 0.22 micron pothyethersulfone membrane filter into a sterile bottle. The filter top is removed from the sterile stock bottle and the stock bottle is capped for storage with a sterile bottle cap.

Diluted 0.01% Solution 0.3 mL of the 1% solution was combined with a quantity sufficient to achieve 30 mL total of sterile 0.9% Sodium Chloride For Injection USP. The solution was thoroughly mixed. The pH of the solution was recorded. A 0.22 micron filter was placed on the tip of the syringe and the solution was aliquotted into separate sterile containers.

Example 3—Preparation of an Aqueous Solution Formulation Containing 0.01% Atropine Sulfate Stock 1% Solution In a 100 mL solution, 1 gram of atropine sulfate, and 0.77 g of NaCl (and other ingredients/components preferably in their dry state) were added along with a quantity sufficient to equal 100 mL sterile water for injection. The solution was mixed in an appropriately sized beaker with a stir bar on a hot plate until all of the solid powders had dissolved and the solution became clear with no visible particles. Next, the stir bar was removed, and the solution was poured into a filter bottle and vacuum filtered through a 0.22 micron pothyethersulfone membrane filter into a sterile bottle. The filter top was removed from the sterile stock bottle and the stock bottle was capped for storage with a sterile bottle cap.

Diluted 0.01% Solution 0.3 mL of the 1% solution was combined with a quantity sufficient to achieve 30 mL total of sterile 0.9% Sodium Chloride For Injection USP. The solution was thoroughly mixed. The pH of the solution was recorded. A 0.22 micron filter was placed on the tip of the syringe and the solution was aliquotted into separate sterile containers.

Example 4—Stability Analysis

Five 0.01% atropine sulfate solutions were prepared from the 1% atropine sulfate stock solution (preparation as described in Example 2). The pH of the five solutions was 5.87, 5.97, 5.90, 6.24, and 6.16 for solutions 1-5, respectively. Each solution was thoroughly mixed. A 0.22 micron filter was placed on the tip of the syringe and the solution was aliquotted into separate sterile containers according to Table 9.

TABLE 9

Container Filling Outline

| Type of Container | Volume of 0.01% Atropine Sulfate Drug Product in Container | Total Containers Filled |
|---|---|---|
| Sterile Eyedroppers | 5-mL | 12 |
| Sterile Glass Vials | 5-mL | 12 |

The samples were then stored at different conditions for stability analysis. The samples were analyzed at different time points up to 2 months. The storage conditions include: 40° C. with 75% relative humidity (RH) (samples were transferred from 2-8° C. condition after 3 days), 25° C. with 60% RH, and 60° C. The time points were 1 week, 2 weeks, 1 month, and 2 months. At each of the time point, one plastic eyedropper (LDPE plastic) and one glass vial from each of the stored condition were removed and allowed to equilibrate to ambient conditions. Once equilibrated, both the plastic eyedropper and the glass vials were inverted 3 times. The solution in the eyedroppers was transferred to an HPLC vial in a drop wise fashion through the dropper. The solution in the glass vial was aliquotted into an HPLC vial using a glass Pasteur pipette. The samples were then tested for purity and potency using the UPLC method listed in Table 10.

TABLE 10

UPLC Method Parameters

| Parameter | Condition |
|---|---|
| Column | EMD, Hiber HR PurospherSTAR C-18, 100 × 2.1 mm, 2 μm |
| Mobile Phase/Diluent | 87:13, 50 mM Potassium Phosphate:Acetonitrile, pH 3.5 |
| Flow | Isocratic |
| Flow Rate | 0.5 mL/min |
| Detection Wavelength | 210 nm |
| Column Temperature | 30 ± 3° C. |
| Autosampler Temperature | 5 ± 3° C. |
| Run Time | 6.0 minutes |
| Injection Volume | 10 μL* |
| Needle Wash Solution | 90/10 Water:Acetonitrile |

*Modified from original method to maintain sensitivity at 100 μg/mL nominal.

Table 11 lists the stability data for the 0.01% atropine sulfate solutions.

TABLE 11

Stability Data for 0.01% Atropine Sulfate Solutions

| Analyst | Container Type | Storage Condition | t = 0 Purity | t = 0 Potency | t = 0 pH | t = 1 week Purity | t = 1 week Potency | t = 2 week[1] Purity | t = 2 week[1] Potency | t = 1 month[2] Purity | t = 1 month[2] Potency | t = 1 month[2] pH | t = 2 month[3] Purity | t = 2 month[3] Potency | t = 2 month[3] pH |
|---|---|---|---|---|---|---|---|---|---|---|---|---|---|---|---|
| 1 | Eyedropper, LDPE (Plastic) | 25° C./60% RH | 99.5 | 99.8 | 5.9 | ND | ND | 99.1 | 99.9 | ND | ND | ND | 95.4 | 97.4 | 6.3 |
|  |  | 40° C./75% RH |  |  |  | ND | ND | 96.2 | 97.3 | 95.1 | 95.6 | 5.2 | ND | ND | ND |
|  |  | 60° C. |  |  |  | 80.8 | 83.3 | 86.2 | 88.6 | 88.3 | 91.5 | 4.2 | ND | ND | ND |
|  | Glass Vial | 25° C./60% RH | 99.8 | 100.4 | ND | ND | ND | 92.2 | 93.1 | 80.7 | 80.5 | 7.8 | 73.0 | 74.5 | 7.3 |
|  |  | 40° C./75% RH |  |  |  | ND | ND | 73.6 | 74.1 | 50.1 | 50.2 | 7.4 | ND | ND | ND |
|  |  | 60° C. |  |  |  | 43.1 | 43.9 | 28.3 | 28.4 | ND | ND | ND | ND | ND | ND |
| 2 | Eyedropper, LDPE (Plastic) | 25° C./60% RH | 99.7 | 99.9 | 6.0 | ND | ND | 99.1 | 99.6 | ND | ND | ND | 97.0 | 99.1 | 6.1 |
|  |  | 40° C./75% RH |  |  |  | ND | ND | 96.6 | 97.2 | 95.5 | 95.8 | 5.6 | ND | ND | ND |
|  |  | 60° C. |  |  |  | 89.4 | 92.2 | 92.2 | 94.0 | 90.6 | 94.4 | 4.1 | ND | ND | ND |
|  | Glass Vial | 25° C./60% RH | 99.8 | 100.2 | ND | ND | ND | 92.6 | 92.9 | 82.5 | 82.2 | 7.6 | 80.2 | 81.6 | 7.3 |
|  |  | 40° C./75% RH |  |  |  | ND | ND | 74.7 | 75.1 | 59.1 | 59.0 | 7.2 | ND | ND | ND |
|  |  | 60° C. |  |  |  | 54.2 | 55.2 | 37.3 | 37.4 | ND | ND | ND | ND | ND | ND |
| 3 | Eyedropper, LDPE (Plastic) | 25° C./60% RH | 99.3 | 96.3 | 5.9 | ND | ND | 98.7 | 96.1 | ND | ND | ND | 95.8 | 94.8 | 6.3 |
|  |  | 40° C./75% RH |  |  |  | ND | ND | 96.7 | 93.1 | 94.8 | 91.8 | 5.5 | ND | ND | ND |
|  |  | 60° C. |  |  |  | 88.8 | 89.0 | 88.0 | 86.8 | 88.6 | 87.7 | 4.1 | ND | ND | ND |
|  | Glass Vial | 25° C./60% RH | 99.4 | 98.4 | ND | ND | ND | 94.1 | 91.2 | 85.0 | 81.9 | 7.5 | 79.3 | 78.3 | 7.3 |
|  |  | 40° C./75% RH |  |  |  | ND | ND | 72.2 | 74.6 | 61.3 | 63.0 | 7.2 | ND | ND | ND |
|  |  | 60° C. |  |  |  | 48.6 | 51.1 | 34.1 | 34.9 | ND | ND | ND | ND | ND | ND |
| 4 | Eyedropper, LDPE (Plastic) | 25° C./60% RH | 99.8 | 99.6 | 6.2 | ND | ND | 99.1 | 98.8 | ND | ND | ND | 96.4 | 97.6 | 6.3 |
|  |  | 40° C./75% RH |  |  |  | ND | ND | 96.3 | 97.0 | 94.5 | 94.2 | 5.6 | ND | ND | ND |
|  |  | 60° C. |  |  |  | 90.5 | 93.0 | 89.3 | 90.6 | 84.2 | 85.8 | 4.2 | ND | ND | ND |
|  | Glass Vial | 25° C./60% RH | 99.8 | 98.8 | ND | ND | ND | 90.7 | 90.0 | 76.9 | 75.1 | 7.6 | 72.5 | 71.6 | 7.4 |
|  |  | 40° C./75% RH |  |  |  | ND | ND | 71.0 | 68.7 | 57.0 | 56.7 | 7.2 | ND | ND | ND |
|  |  | 60° C. |  |  |  | 52.4 | 52.1 | 29.7 | 28.6 | ND | ND | ND | ND | ND | ND |
| 5 | Eyedropper, LDPE (Plastic) | 25° C./60% RH | 99.6 | 100.5 | 6.2 | ND | ND | 99.3 | 100.4 | ND | ND | ND | 97.8 | 100.5 | 6.2 |
|  |  | 40° C./75% RH |  |  |  | ND | ND | 95.9 | 96.7 | 96.8 | 97.6 | 5.5 | ND | ND | ND |
|  |  | 60° C. |  |  |  | 91.2 | 94.6 | 91.4 | 93.6 | 90.3 | 92.8 | 4.2 | ND | ND | ND |
|  | Glass Vial | 25° C./60% RH | 99.8 | 100.7 | ND | ND | ND | 90.5 | 91.3 | 79.3 | 79.7 | 7.8 | 72.8 | 74.6 | 7.3 |
|  |  | 40° C./75% RH |  |  |  | ND | ND | 71.3 | 71.9 | 56.0 | 56.4 | 7.3 | ND | ND | ND |
|  |  | 60° C. |  |  |  | 46.3 | 47.4 | 29.5 | 29.6 | ND | ND | ND | ND | ND | ND |

[1]The 25° C. and the 60° C. samples were pulled at 15 days, the 40° C. samples were pulled at 11 days.
[2]The 25° C. and the 60° C. samples were pulled at 28 days, the 40° C. samples were pulled at 24 days.
[3]The 25° C. and the 60° C. samples were pulled at 46 days.

A change in the pH of the 0.01% Atropine Sulfate solutions was observed over the course of the stability study. The plastic (LDPE) eyedroppers maintained pH around 6.2 when stored at 25° C. for 2 months. However at the same time point, the pH of the 0.01% atropine has increased to 7.2 when stored in glass vials. Additionally, when stored at elevated temperatures (e.g. 40° C. and 60° C.), the pH in the plastic (LDPE) eyedroppers dropped to approximately 4-5, while the pH maintained around 7.2 when stored in the glass vials.

There was also a significant difference in the rate of degradation for Atropine Sulfate (0.01%) when stored in plastic (LDPE) eyedroppers versus Type I glass vials. However, in both containers there was an increase of an early eluting related substance at relative retention time (RRT) =0.87-0.89. In some cases, this early eluting related substance is referred to as primary degradant. In some instances, the primary degradant is referred to as RRT 0.87-0.89. This related substance is likely to be the first parameter to fail specification regardless of the container. The amount of this related substance was tracked at each time point and is listed in Table 12.

TABLE 12

Area (%) of the Main Degradation Species for 0.01% Atropine Sulfate (RRT 0.87-0.89)

| Analyst | Temperature °C. | t = 0 | t = 1 week | t = 2 week | t = 1 month | t = 2 months |
|---|---|---|---|---|---|---|
| 1 | 25 | 0.08 | NA | 0.92 | NA | 3.98 |
|   | 40 | NA | NA | 3.74 | 4.78 | NA |
|   | 60 | NA | 17.78 | 13.49 | 11.51 | NA |
| 2 | 25 | 0.07 | NA | 0.88 | NA | 2.46 |
|   | 40 | NA | NA | 3.26 | 4.37 | NA |
|   | 60 | NA | 9.38 | 7.67 | 9.13 | NA |
| 3 | 25 | 0.07 | NA | 1.05 | NA | 2.88 |
|   | 40 | NA | NA | 2.98 | 4.85 | NA |
|   | 60 | NA | 9.59 | 11.57 | 10.55 | NA |
| 4 | 25 | 0.08 | NA | 0.92 | NA | 3.09 |
|   | 40 | NA | NA | 3.43 | 5.32 | NA |
|   | 60 | NA | 8.30 | 10.46 | 15.49 | NA |
| 5 | 25 | 0.08 | NA | 0.64 | NA | 1.66 |
|   | 40 | NA | NA | 3.96 | 3.07 | NA |
|   | 60 | NA | 7.61 | 8.35 | 9.7 | NA |
| Average 25° C. | | 0.08 | NA | 0.88 | NA | 2.81 |
| Average 40° C. | | NA | NA | 3.47 | 4.48 | NA |
| Average 60° C. | | NA | 10.53 | 10.31 | 11.28 | NA |

Figures 2A, 2B, 2C:
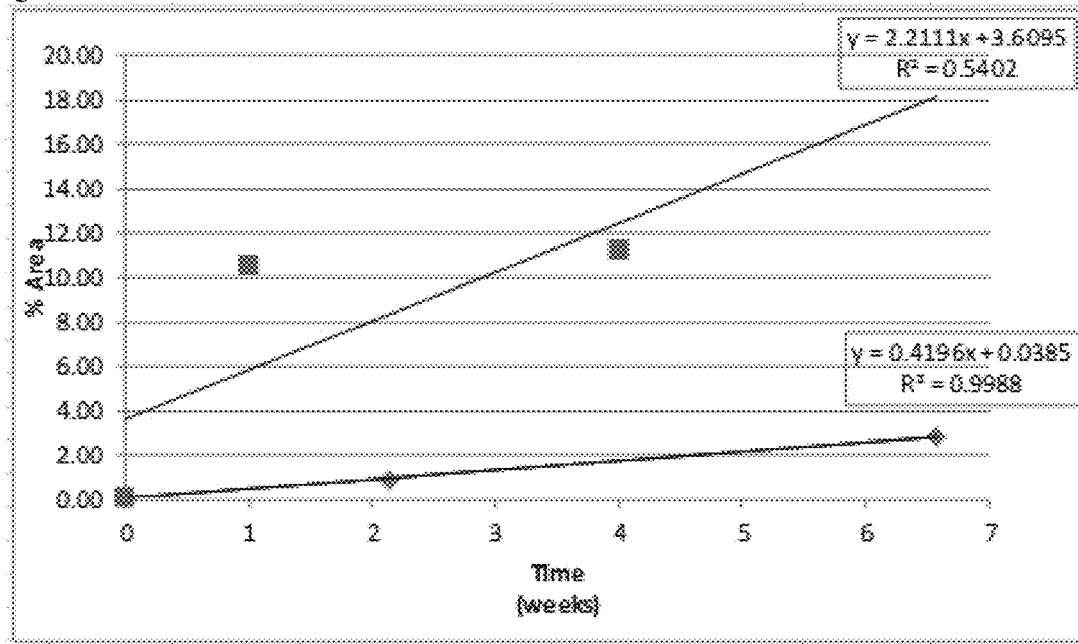
FIG. 2A-FIG. 2C show the shelf life prediction of 0.01% atropine sulfate solution with a primary degradant RRT 0.87-0.89, and a n.m.t. of 0.5% area, based on data obtained from samples stored at 25° C. and 60° C. The pH range of the atropine sulfate solution is from 5.9-6.2.

Arrhenius based shelf life predictions were calculated using the related substance data from Table 12. These predictions are based on an assumption that the degradation is first order (linear). These predictions are illustrated in FIGS. 1 and 2. FIG. 1 shows the shelf life prediction of 0.01% atropine sulfate solution with a primary degradant RRT 0.87-0.89, and a n.m.t. of 0.5% area, based on data obtained from samples stored at 25° C. and 40° C. The pH range of the atropine sulfate solution is from 5.9-6.2. FIG. 2 shows the shelf life prediction of 0.01% atropine sulfate solution with a primary degradant RRT 0.87-0.89, and a n.m.t. of 0.5% area, based on data obtained from samples stored at 25° C. and 60° C. The pH range of the atropine sulfate solution is from 5.9-6.2.

Example 5—1% Atropine Sulfate (Bausch+Lomb) Sample Analysis

The 1% atropine sulfate sample was obtained from Bausch+Lomb (Lot 198421). For comparison the pH of the 1% Atropine Sulfate drug product was determined in the neat solution as well as a sample that was diluted to the current nominal concentration (0.01% Atropine Sulfate) using the vehicle. Additionally a sample was diluted to the nominal concentration with method diluent. Both samples diluted to the nominal concentration were analyzed using the RP-UPLC method (Table 10). The results are listed in Table 13.

TABLE 13 pH and Purity of the Bausch + Lomb Atropine Sulfate Sample

| Sample | pH | Purity (% area) |
|---|---|---|
| 1% Atropine Sulfate | 4.89 | ND |
| 0.01% Atropine Sulfate, diluted with Vehicle | 6.16 | 99.6% |
| 0.01% Atropine Sulfate, diluted with Diluent | ND | 99.6% |
| Vehicle | 7.94 | ND |

ND = not determined

Example 6—Dose Uniformity (10-Dose)

To evaluate the dose-to-dose uniformity, drop bottles containing the ophthalmic aqueous composition are stored upright for a predetermined period of time (e.g. 12 hours) prior to the start of the test. To simulate the recommended dosing of the product, 10 drops of the aqueous composition are dispensed from each bottle at predetermined time intervals (e.g. consecutively, every 1 minute, every 10 minutes, every hour or every 24 hours). All drops are dispensed into tared glass vials, capped, and stored at room temperature until analysis. Concentrations of atropine in the expressed drops are determined using a reverse-phase HPLC method.

Example 7—Dose Uniformity (5-Dose)

To evaluate the dose-to-dose uniformity, drop bottles containing the ophthalmic aqueous composition are stored upright for a predetermined period of time (e.g. 12 hours) prior to the start of the test. To simulate the recommended dosing of the product, 5 drops of the aqueous composition are dispensed from each bottle at predetermined time intervals (e.g. consecutively, every 1 minute, every 10 minutes, every hour or every 24 hours). All drops are dispensed into tared glass vials, capped, and stored at room temperature until analysis. Concentrations of atropine in the expressed drops are determined using a reverse-phase HPLC method.

Example 8—Dose Uniformity (2-Dose)

To evaluate the dose-to-dose uniformity, drop bottles containing the ophthalmic aqueous composition are stored upright for a predetermined period of time (e.g. 12 hours) prior to the start of the test. To simulate the recommended dosing of the product, 2 drops of the aqueous composition are dispensed from each bottle at predetermined time intervals (e.g. consecutively, every 1 minute, every 10 minutes, every hour or every 24 hours). All drops are dispensed into tared glass vials, capped, and stored at room temperature until analysis. Concentrations of atropine in the expressed drops are determined using a reverse-phase HPLC method.

Example 9—Formulation Stability Comparison

Atropine sulfate monohydrate (MP Bio; Lot Number 7825K) and tropic acid (Sigma Aldrich; Lot Number STBD6457V) were used for this experiment. Eight formulations illustrated in Table 14A were analyzed at t=0, 2 weeks, and 4 weeks. A RP-HPLC method was used to carry out the analysis.

TABLE 14A

Atropine sulfate formulations

| Formulation | Atropine Sulfate Monohydrate | Benzalkonium Chloride (BAK) | Sodium Chloride | Acetic Acid | Citric Acid | pH/pD | Aqueous |
|---|---|---|---|---|---|---|---|
| 1 | 0.010 | 0.01 | 0.90 | 0.01 | — | 4.2 | SWFI |
| 2 | 0.025 | 0.01 | 0.90 | 0.01 | — | 4.2 | SWFI |
| 3 | 0.010 | 0.01 | 0.90 | 0.01 | — | 4.8 | SWFI |
| 4 | 0.025 | 0.01 | 0.90 | 0.01 | — | 4.8 | SWFI |
| 5 | 0.010 | 0.01 | 0.90 | — | 0.04 | 5.8 | SWFI |
| 6 | 0.025 | 0.01 | 0.90 | — | 0.04 | 5.8 | SWFI |
| 7 | 0.010 | 0.01 | 0.90 | 0.01 | — | 5.2 (pD) | $D_2O$ |
| 8 | 0.010 | 0.01 | 0.90 | — | 0.04 | 6.2 (pD) | $D_2O$ |

The values are % w/v. The formulations were prepared at 100 mL scale in volumetric glassware. The pD of Formulation 7 and Formulation 8 are 5.2 and 6.2, respectively. In some instances, the pD is calculated as pD=0.4+pH*, in which pH* is the measured or observed pH of the solution formulated in a solution containing deuterated water.

Table 14B illustrates analysis time points for the formulations listed in Table 14A.

TABLE 14B

Schedule for atropine sulfate formulation testing

| Storage Condition (Horizontal) | Time Point | | |
|---|---|---|---|
| | Initial (t = 0) | 2 Week | 4 Week |
| 25° C./60% RH | X | X | X |
| 40° C./75% RH | | X | X |
| 60° C. | | X | X |

Table 15 illustrates the atropine sulfate purity data associated with each of the eight formulations. Purity is indicated as percentage of area under the curve.

TABLE 15

Atropine sulfate purity as Area-%

| Solvent | Condition | t = 0 | t = 2 weeks | t = 4 weeks[1] |
|---|---|---|---|---|
| Formulation 1 pH 4.2 | 25/60 | 97.39 | 97.76 | 98.20 |
| | 40/75 | | 97.25 | 97.04 |
| | 60° C. | | 94.98 | 93.87 |
| Formulation 2 pH 4.2 | 25/60 | 98.85 | 99.03 | 99.08 |
| | 40/75 | | 98.50 | 98.32 |
| | 60° C. | | 97.47 | 96.65 |
| Formulation 3 pH 4.8 | 25/60 | 98.16 | 98.16 | 98.45 |
| | 40/75 | | 97.98 | 97.35 |
| | 60° C. | | 95.94 | 94.65 |
| Formulation 4 pH 4.8 | 25/60 | 98.81 | 98.75 | 98.46 |
| | 40/75 | | 98.26 | 98.01 |
| | 60° C. | | 96.22 | 94.04 |
| Formulation 5 pH 5.8 | 25/60 | 98.16 | 97.92 | 97.54 |
| | 40/75 | | 95.88 | 93.51 |
| | 60° C. | | 80.94 | 66.83 |
| Formulation 6 pH 5.8 | 25/60 | 99.08 | 98.91 | 98.46 |
| | 40/75 | | 97.65 | 96.20 |
| | 60° C. | | 89.15 | 80.68 |
| Formulation 7 pD 5.2 | 25/60 | 98.93 | 99.07 | 98.39 |
| | 40/75 | | 98.51 | 97.55 |
| | 60° C. | | 96.70 | 94.01 |
| Formulation 8 pD 6.2 | 25/60 | 98.93 | 98.95 | 98.51 |
| | 40/75 | | 98.53 | 97.44 |
| | 60° C. | | 95.97 | 92.72 |

[1]Some chromatographic interference were observed to occur late in the run (~27-32 minutes) for many of the t = 4 week stability samples and in some instances is proposed to be system related.

After four weeks of storage at 60° C., in some instances the atropine sulfate concentration have an impact on the stability for the formulations containing acetic acid at pH 4.2. For example, atropine sulfate concentration at 0.025% w/v (Formulation 2) showed a 2.8% increase in % purity at pH 4.2 compared to the atropine sulfate concentration at 0.010% w/v (Formulation 1). This trend was not observed for the acetic acid formulations at pH 4.8 (Formulations 3 and 4); rather a 0.6% decrease in % purity was observed for the higher doses.

The dose dependent stability trend that was observed at pH=4.2 was also seen in the formulations containing citric acid at pH 5.8 (Formulations 5 and 6). After four weeks of storage at 60° C. there is approximately 14% less degradation in the higher does than observed in the lower dose.

At both the high and the low doses, more degradation is observed in the formulations that start at a higher pH. This degradation is predominantly the growth of tropic acid. In some instances, buffer species plays a role in the observed degradation between the different pH values.

The percentage of tropic acid observed for each of the formulations at t=4 weeks and at 60° C. are as follow:
  Formulation 1—Tropic acid observed is 0.54%.
  Formulation 2—Tropic acid observed is 0.93%.
  Formulation 3—Tropic acid observed is 1.58%.
  Formulation 4—Tropic acid observed is 3.03%.
  Formulation 5—Tropic acid observed is 29.13%.
  Formulation 6—Tropic acid observed is 16.84%.
  Formulation 7—Tropic acid observed is 1.07%.
  Formulation 8—Tropic acid observed is 4.03%.

Figure 4:
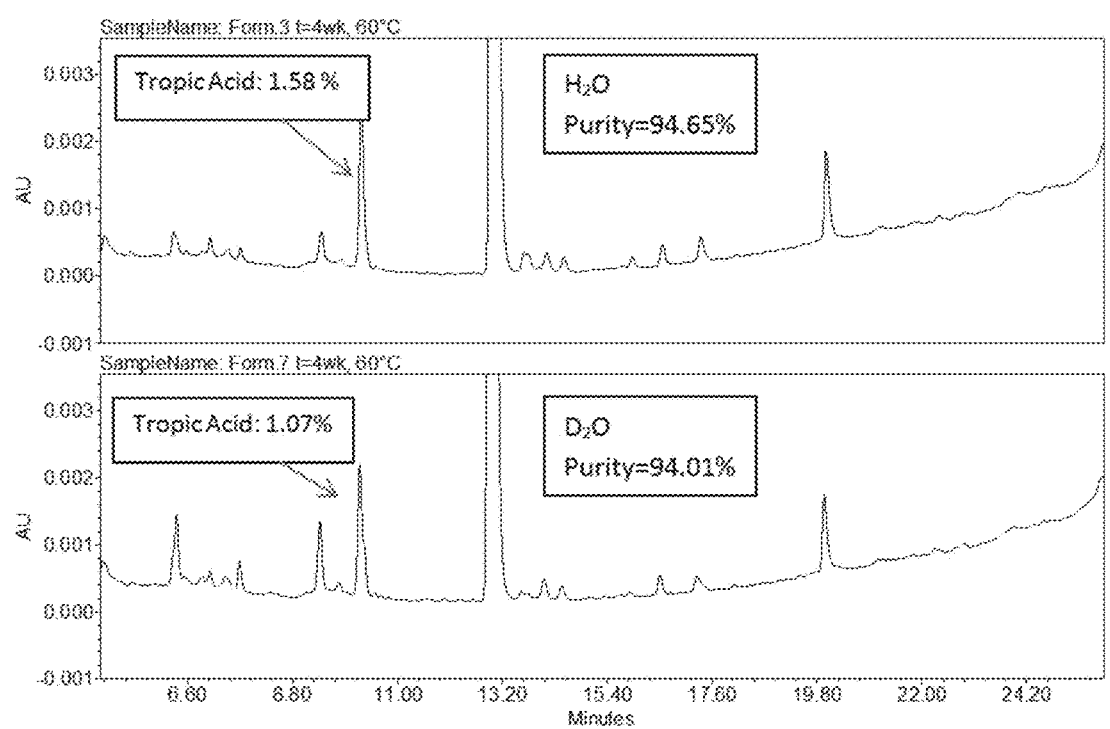
FIG. 4 illustrates atropine sulfate (0.010%) formulation stability in acetic acid. The atropine sulfate formulation is formulated with acetic acid and either with $H_2O$ (top panel, Formulation 3) or $D_2O$ (bottom panel, Formulation 7). Formulation 3 has a pH of 4.8 and Formulation 7 has a pD of 5.2. Both formulations are stored at 60° C. for 4 weeks prior to analysis.
Figure 5:
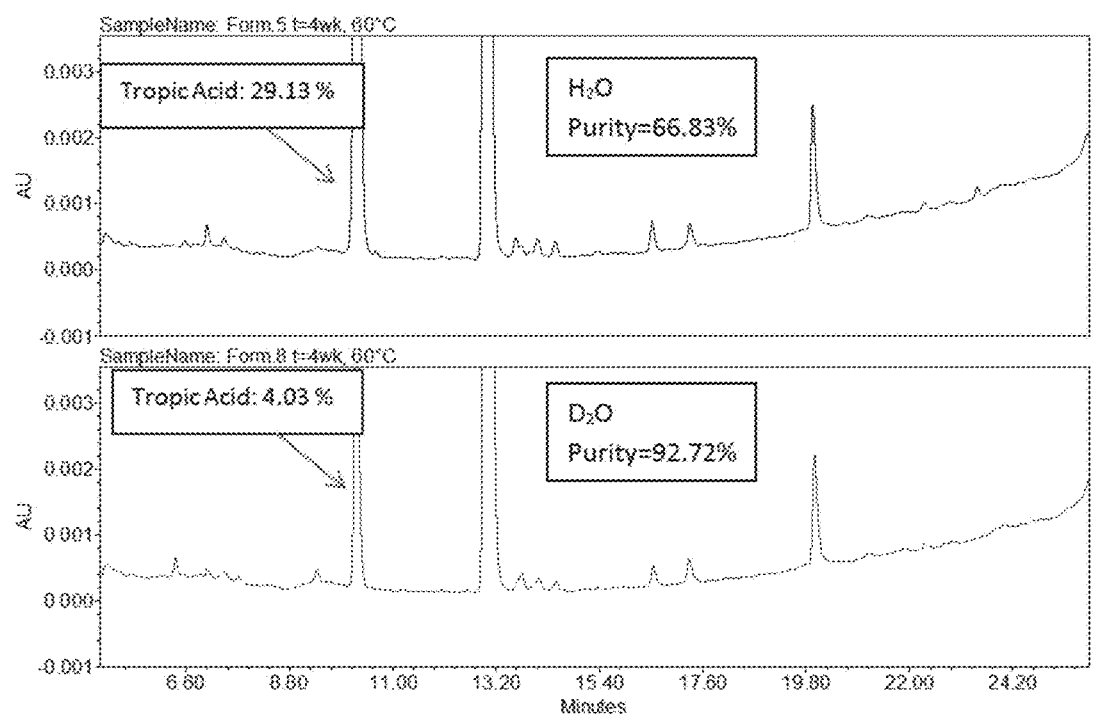
FIG. 5 illustrates atropine sulfate (0.01%) formulation stability in citric acid. The atropine sulfate formulation is formulated with citric acid and either with $H_2O$ (top panel, Formulation 5) or $D_2O$ (bottom panel, Formulation 8). Formulation 5 has a pH of 5.8 and Formulation 8 has a pD of 6.2. Both formulations are stored at 60° C. for 4 weeks prior to analysis.

In some embodiments, switching the water source to deuterated water ($D_2O$) has an impact on stabilizing the growth of the tropic acid peak for the formulation containing acetic acid at pD 5.2 (Formulation 7), see FIG. 4. In addition, in the formulation containing citric acid at pD 6.2 (Formulation 8), the deuterated water also stabilizes atropine sulfate, see FIG. 5.

Table 16 illustrates tropic acid as area under the curve for each of the eight formulations. Tropic acid is a degradant of atropine sulfate. In some instances, LOQ was previously found to be 0.05% for the RP-HPLC method.

TABLE 16

Tropic acid as area-%

| Solvent | Condition | t = 0 | t = 2 weeks | t = 4 weeks |
|---|---|---|---|---|
| Formulation 1 | 25/60 | <LOQ | 0.08 | <LOQ |
| pH 4.2 | 40/75 | | 0.10 | 0.10 |
| | 60° C. | | 0.37 | 0.51 |
| Formulation 2 | 25/60 | <LOQ | 0.05 | <LOQ |
| pH 4.2 | 40/75 | | 0.11 | 0.12 |
| | 60° C. | | 0.46 | 0.93 |
| Formulation 3 | 25/60 | <LOQ | 0.12 | 0.05 |
| pH 4.8 | 40/75 | | 0.19 | 0.27 |
| | 60° C. | | 0.90 | 1.58 |
| Formulation 4 | 25/60 | <LOQ | 0.10 | 0.13 |
| pH 4.8 | 40/75 | | 0.31 | 0.53 |
| | 60° C. | | 1.84 | 3.03 |
| Formulation 5 | 25/60 | <LOQ | 0.40 | 0.71 |
| pH 5.8 | 40/75 | | 2.22 | 4.35 |
| | 60° C. | | 16.62 | 29.13 |
| Formulation 6 | 25/60 | <LOQ | 0.24 | 0.42 |
| pH 5.8 | 40/75 | | 1.30 | 2.44 |
| | 60° C. | | 9.32 | 16.84 |
| Formulation 7 | 25/60 | <LOQ | 0.07 | 0.08 |
| pD 5.2 | 40/75 | | 0.14 | 0.24 |
| | 60° C. | | 0.71 | 1.07 |
| Formulation 8 | 25/60 | <LOQ | 0.11 | 0.14 |
| pD 6.2 | 40/75 | | 0.33 | 0.65 |
| | 60° C. | | 2.32 | 4.03 |

Table 17 illustrates percentage of potency of atropine in the eight formulations.

TABLE 17

% Potency

| Solvent | Condition | t = 0 | t = 2 weeks | t = 4 weeks |
|---|---|---|---|---|
| Formulation 1 | 25/60 | 109.4 | 110.3 | 112.8 |
| pH 4.2 | 40/75 | | 111.0 | 112.4 |
| | 60° C. | | 112.8 | 114.8 |
| Formulation 2 | 25/60 | 102.9 | 107.1 | 109.7 |
| pH 4.2 | 40/75 | | 108.4 | 109.6 |
| | 60° C. | | 109.4 | 111.0 |
| Formulation 3 | 25/60 | 106.3 | 108.0 | 109.6 |
| pH 4.8 | 40/75 | | 108.1 | 110.0 |
| | 60° C. | | 108.0 | 109.9 |
| Formulation 4 | 25/60 | 102.5 | 107.9 | 109.2 |
| pH 4.8 | 40/75 | | 107.4 | 108.9 |
| | 60° C. | | 107.9 | 108.8 |
| Formulation 5 | 25/60 | 105.0 | 105.9 | 107.1 |
| pH 5.8 | 40/75 | | 103.8 | 103.5 |
| | 60° C. | | 90.2 | 77.7 |
| Formulation 6 | 25/60 | 107.2 | 107.1 | 109.1 |
| pH 5.8 | 40/75 | | 106.8 | 107.1 |
| | 60° C. | | 99.0 | 93.7 |
| Formulation 7 | 25/60 | 107.3 | 111.3 | 112.9 |
| pD 5.2 | 40/75 | | 111.6 | 113.5 |
| | 60° C. | | 111.8 | 113.5 |
| Formulation 8 | 25/60 | 99.0 | 103.0 | 105.0 |
| pD 6.2 | 40/75 | | 104.9 | 104.7 |
| | 60° C. | | 101.6 | 103.0 |

Figure 3:
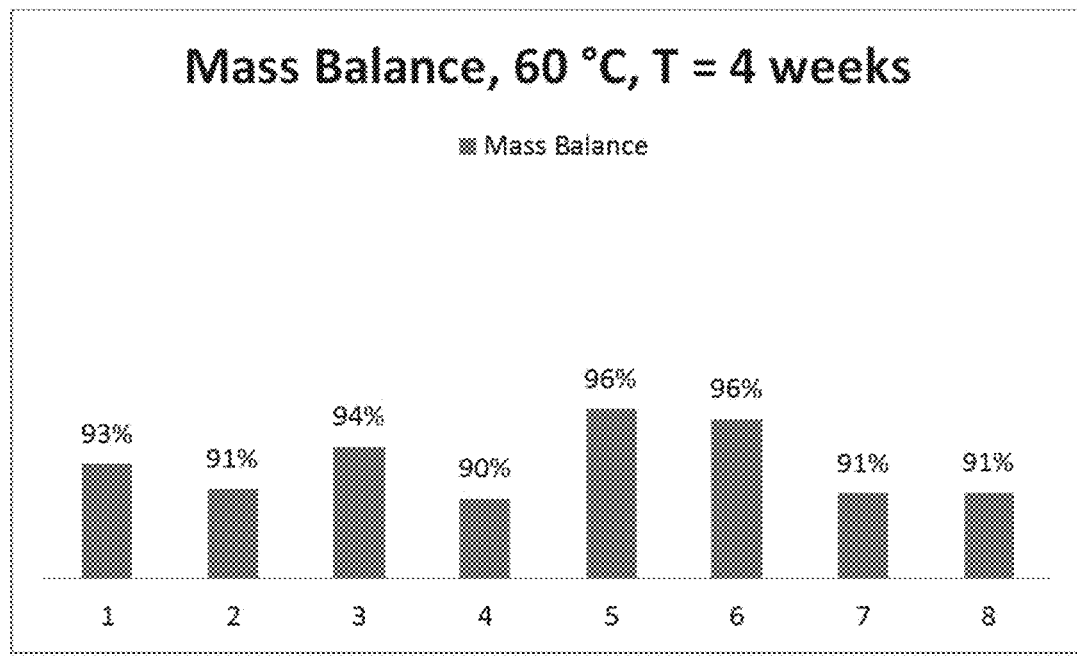
FIG. 3 illustrates mass balance at 4 weeks and at 60° C. condition for atropine sulfate formulations disclosed in Example 9.

After 4 weeks of storage, the observed potency values were elevated from the t=0 and 2 week time points, with the exception of Formulations 5 and 6 at 60° C. where the potencies dropped due to degradation. In some instances, these potency values are within the error of the HPLC method, but appear to be trending upward. Mass balance was calculated for the 60° C. data and results were consistent across the formulations and levels of degradation, although skewed lower due to the higher than anticipated potency values at 4 weeks, see FIG. 3.

Table 18 illustrates pH or pD stability of the eight formulations.

TABLE 18 pH/pD Stability

| Solvent | Condition | t = 0 | t = 2 weeks | t = 4 weeks |
|---|---|---|---|---|
| Formulation 1 | 25/60 | 4.21 | 3.93 | 4.02 |
| (pH) | 40/75 | | 3.86 | 3.96 |
| | 60° C. | | 3.71 | 3.86 |
| Formulation 2 | 25/60 | 4.26 | 4.11 | 4.25 |
| (pH) | 40/75 | | 4.04 | 4.17 |
| | 60° C. | | 3.93 | 4.10 |
| Formulation 3 | 25/60 | 4.85 | 4.44 | 4.61 |
| (pH) | 40/75 | | 4.41 | 4.54 |
| | 60° C. | | 4.32 | 4.40 |
| Formulation 4 | 25/60 | 4.98 | 4.93 | 5.05 |
| (pH) | 40/75 | | 4.89 | 4.98 |
| | 60° C. | | 4.77 | 4.77 |
| Formulation 5 | 25/60 | 5.87 | 5.93 | 6.03 |
| (pH) | 40/75 | | 5.96 | 5.96 |
| | 60° C. | | 5.82 | 5.78 |
| Formulation 6 | 25/60 | 5.80 | 5.69 | 5.77 |
| (pH) | 40/75 | | 5.65 | 5.67 |
| | 60° C. | | 5.54 | 5.50 |
| Formulation 7 | 25/60 | *5.31* | *5.10* | *5.24* |
| (pD) | 40/75 | | *5.08* | *5.15* |
| | 60° C. | | *5.00* | *4.93* |
| Formulation 8 | 25/60 | *6.25* | *5.72* | *5.88* |
| (pD) | 40/75 | | *5.74* | *5.78* |
| | 60° C. | | *5.58* | *5.50* |

The italicized values are pD values for a deuterated sample. In some embodiments, the pD of the deuterated samples are pD=$pH_{reading}$+0.4 (Glasoe, et al. "Use of glass electrodes to measure acidities in deuterium oxide" J. Physical Chem. 64(1): 188-190 (1960)).

At the two lower temperatures, the pH values at t=4 week are slightly elevated from the t=2 week time point. These data were generated using a new glass pH probe. In some instances, the observed differences are due to the probe differences or additional variables such as for example, the age of the standard buffers or temperature gradients within the laboratory environment. The downward pH trend for each formulation with increasing temperatures at t=4 week is consistent with previous data and is consistent with the increase in the amount of tropic acid present in the stability sample.

Example 10—Determination of Shelf Life and Activation Energy

Activation energy was calculated for the eight formulations disclosed in Example 9 and comparison with a reference standard was made with Formulations 4-7.

Figure 6:
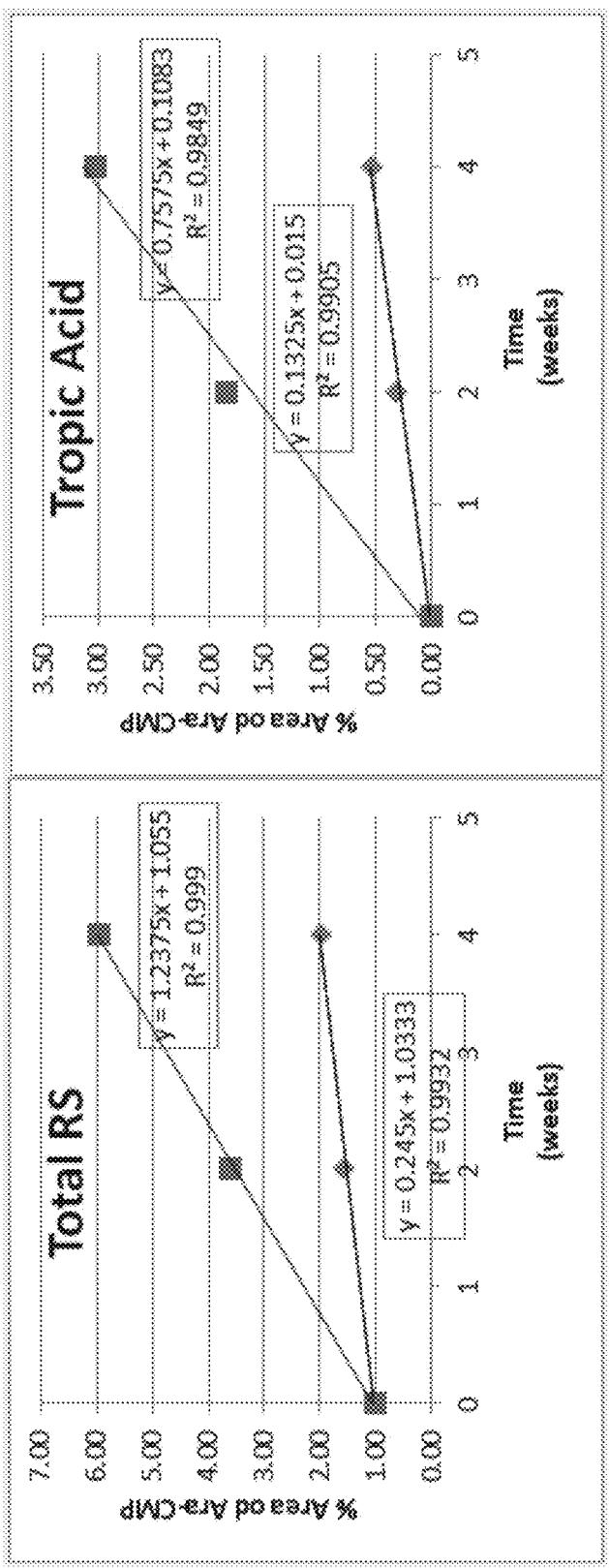
FIG. 6 illustrates comparison of total RS and tropic acid for atropine sulfate (0.025%) formulation (Formulation 4) at pH 4.8 in $H_2O$.
Figure 7:
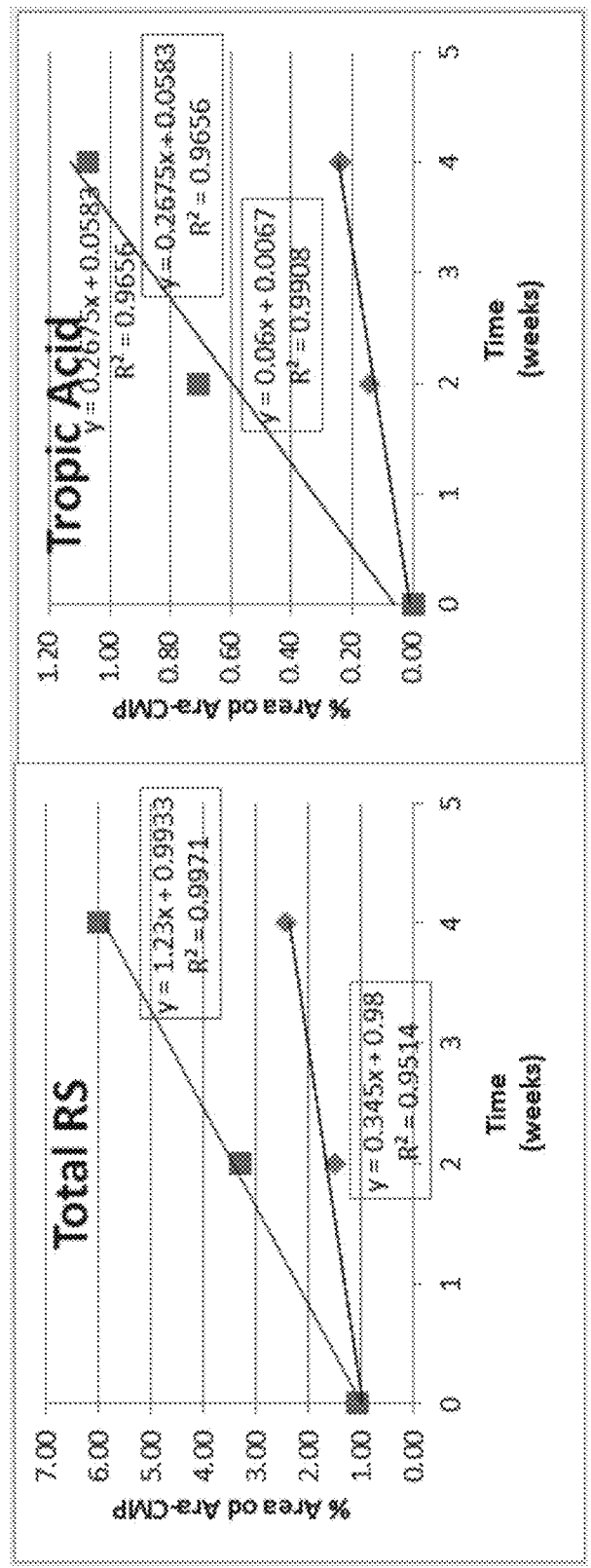
FIG. 7 illustrates comparison of total RS and tropic acid for atropine sulfate (0.01%) formulation (Formulation 7) at pD 5.2 in $D_2O$.
Figure 8:
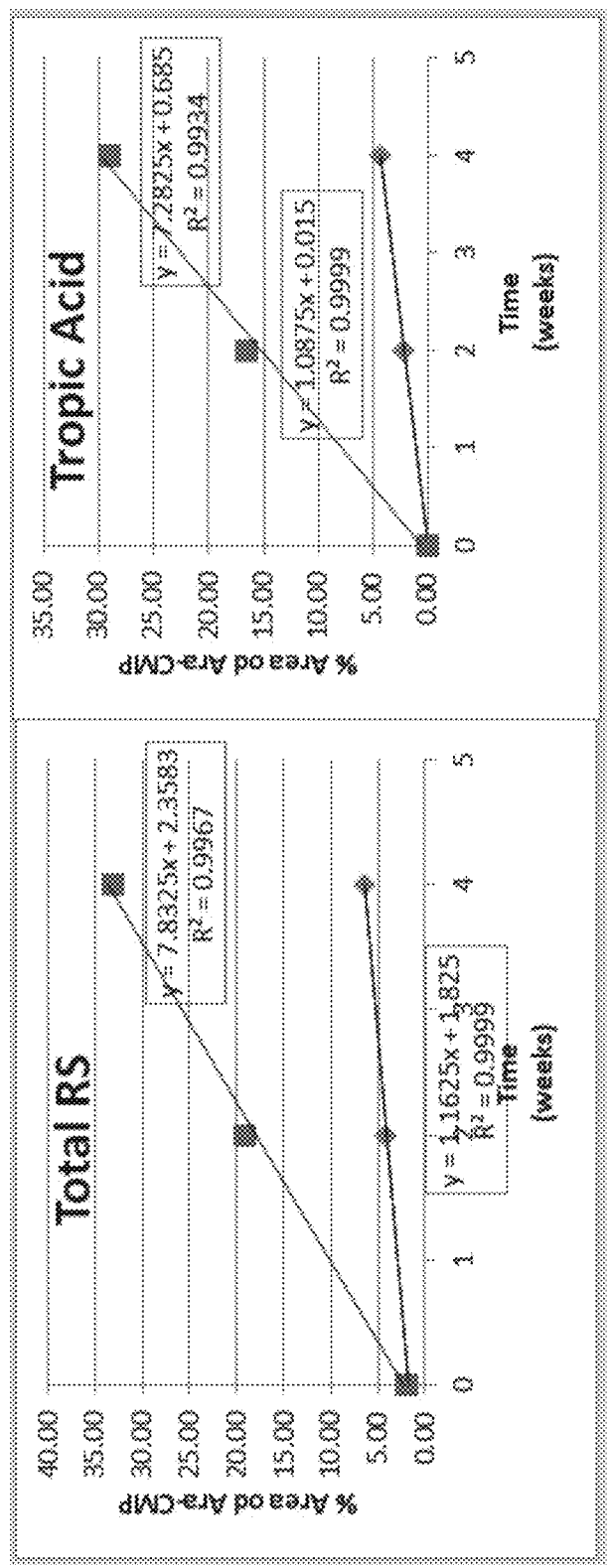
FIG. 8 illustrates comparison of total RS and tropic acid for atropine sulfate (0.01%) formulation (Formulation 5) at pH 5.8 in $H_2O$.
Figure 9:
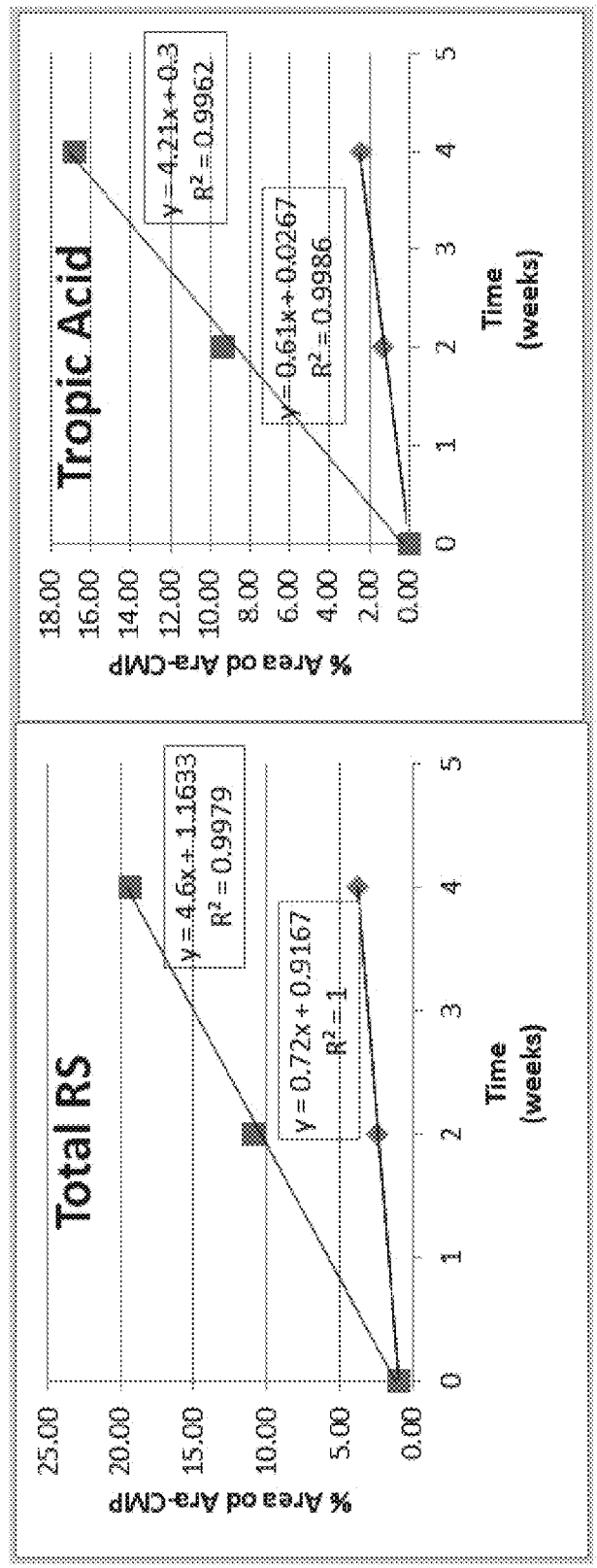
FIG. 9 illustrates comparison of total RS and tropic acid for atropine sulfate (0.025%) formulation (Formulation 6) at pH 5.8 in $H_2O$.

Table 19 illustrates the activation energy (Ea) calculation. The Ea minimum is 17.8 Kcal/mol, the Ea maximum is 21.3 Kcal/mol, and the Ea mean is 19.5 Kcal/mol. Mean is +/−3*stdev. FIGS. 6 and 7 illustrate the poor correlation between RS and tropic acid with Formulation 4 and Formulation 7, respectively. FIGS. 8 and 9 illustrate improved correlation between RS and tropic acid with Formulation 5 and Formulation 6, respectively. At a lower pH (e.g. pH 4.8 or lower), there was a poor correlation observed (Formulation 4 and Formulation 7). This was due to a slowed hydrolysis and increased alternative degradation pathways. At a higher pH (e.g., pH 5.8 or higher), an improved or better correlation was observed (Formulation 5 and Formulation 6). This was due to the hydrolysis of atropine as the primary degradant. It is noted that the activation energy is for the specific acid catalyzed degradation to tropic acid-the predominant degradation product and degradation mechanism operating at pH 5.8 or higher.

TABLE 19

Activation energy for total related substance (RS) and tropic acid.

|   | Total RS | Tropic Acid |   |
|---|---|---|---|
| 1 | Poor Corr | Poor Corr |   |
| 2 | 12.2 | Poor Corr |   |
| 3 | Poor Corr | 18.3 |   |
| 4 | 16.8 | 18.1 |   |
| 5 | 19.8 | 19.7 |   |
| 6 | 19.2 | 20.0 |   |
| 7 | 13.2 | 15.5 |   |
| 8 | Poor Corr | 18.9 |   |
| Mean | 16.2 | 18.4 | Kcal/mole |
| Stdev | 3.4 | 1.6 |   |
| RSD | 21% | 9% |   |

Table 20 illustrates the rate of RS or tropic acid formation per week at 40° C.

TABLE 20

| Formulation |   | Rate 40° C. (total RS %/wk) | Rate 40° C. (Tropic acid %/wk) |
|---|---|---|---|
| Formulation 5 | 0.01% Atr Citrate pH 5.8 | 1.16 | 1.09 |
| Formulation 6 | 0.025% Atr Citrate pH 5.8 | 0.72 | 0.61 |
| Formulation 8 | 0.01% Atr Citrate pD 6.2 $D_2O$ |   | 0.163 |

Table 21 illustrates the activation energy and predicted shelf life at 30° C. calculated based on Table 20. It is assumed for the calculation that tropic acid and total RS is 5% (self-life).

TABLE 21A

| | Rate @30° C. (Total RS %/wk) | | | Estimated Shelf life | | |
| | Ea | | | @30° C. (mo) | | |
| Formulation | Ea min | Ea mean | max | Ea min | Ea mean | Ea max |
| 5 | 0.45 | 0.41 | 0.38 | 2.78 | 3.04 | 3.33 |
| 6 | 0.28 | 0.26 | 0.23 | 4.47 | 4.90 | 5.37 |
| 8 | — | — | — | — | — | — |

TABLE 21B

| | Rate @30° C. (Tropic acid %/wk) | | | Estimated Shelf life | | |
| | Ea | | | @30° C. (mo) | | |
| Formulation | Ea min | Ea mean | max | Ea min | Ea mean | Ea max |
| 5 | 0.42 | 0.39 | 0.35 | 2.95 | 3.24 | 3.54 |
| 6 | 0.24 | 0.22 | 0.20 | 5.28 | 5.78 | 6.33 |
| 8 | 0.06 | 0.06 | 0.05 | 19.75 | 21.64 | 23.70 |

At pD 6.2, the deuterated formulation (Formulation 8) has a predicted shelf life of close to 2 years at 30° C.

Table 22 illustrate the predicted shelf life at temperatures of 40° C., 30° C., 25° C., and 2-8° C. for Formulations 4-8 for total RS and tropic acid, respectively.

TABLE 22

Stability Prediction

| Formulation | Temperature (° C.) | RS weeks | RS months | Temperature (° C.) | Tropic Acid weeks | Tropic Acid months |
|---|---|---|---|---|---|---|
| 4 | 40 | 16.5 | 4.1 | 40 | 7.7 | 1.9 |
|   | 30 | 40.2 | 10.1 | 30 | 20.0 | 5.0 |
|   | 25 | 64.2 | 16.0 | 25 | 33.0 | 8.3 |
|   | 2-8 | 493.4 | 123.4 | 2-8 | 296.8 | 74.2 |
| 5 | 40 | 2.8 | 0.7 | 40 | 0.9 | 0.2 |
|   | 30 | 7.9 | 2.0 | 30 | 2.7 | 0.7 |
|   | 25 | 13.7 | 3.4 | 25 | 4.6 | 1.2 |
|   | 2-8 | 151.1 | 37.8 | 2-8 | 50.5 | 12.6 |
| 6 | 40 | 5.8 | 1.4 | 40 | 1.7 | 0.4 |
|   | 30 | 15.9 | 4.0 | 30 | 4.8 | 1.2 |
|   | 25 | 27.3 | 6.8 | 25 | 8.4 | 2.1 |
|   | 2-8 | 281.6 | 70.4 | 2-8 | 95.9 | 24.0 |
| 7 | 40 | 11.5 | 2.9 | 40 | 16.9 | 4.2 |
|   | 30 | 23.2 | 5.8 | 30 | 38.4 | 9.6 |
|   | 25 | 33.4 | 8.4 | 25 | 59.1 | 14.8 |
|   | 2-8 | 165.7 | 41.4 | 2-8 | 388.2 | 97.1 |
| 8 | 40 | — | — | 40 | 6.2 | 1.6 |
|   | 30 | — | — | 30 | 17.0 | 4.3 |
|   | 25 | — | — | 25 | 28.9 | 7.2 |
|   | 2-8 | — | — | 2-8 | 287.1 | 71.8 |

Example 11—Additional Formulation Stability Comparison

Atropine sulfate monohydrate (MP Bio; Lot Number 7825K) and tropic acid (Sigma Aldrich; Lot Number STBD6457V) were used for this experiment. Thirteen formulations illustrated in Table 23A were analyzed. Formulations 1-8 had been analyzed at t=0, 2 weeks, 4 weeks, and 8 weeks. Formulations 9-13 had been analyzed at t=0, 2 weeks, and 4 weeks. The pH values reported herein are the measured pH values obtained using the Thermo Scientific, Orion Dual Star pH/ISE benchtop pH meter and the Orion Double Junction Micro pH probe S/N S01-18520 calibrated with $H_2O$ based standards.

TABLE 23A

Atropine sulfate Formulations

| Formulation | Atropine Sulfate Monohydrate | Benzalkonium Chloride (BAK) | Sodium Chloride | Acetic Acid | Citric Acid | pH/pD | Aqueous |
|---|---|---|---|---|---|---|---|
| 1 | 0.010 | 0.01 | 0.90 | 0.01 | — | 4.2 | SWFI |
| 2 | 0.025 | 0.01 | 0.90 | 0.01 | — | 4.2 | SWFI |
| 3 | 0.010 | 0.01 | 0.90 | 0.01 | — | 4.8 | SWFI |
| 4 | 0.025 | 0.01 | 0.90 | 0.01 | — | 4.8 | SWFI |
| 5 | 0.010 | 0.01 | 0.90 | — | 0.04 | 5.8 | SWFI |
| 6 | 0.025 | 0.01 | 0.90 | — | 0.04 | 5.8 | SWFI |
| 7 | 0.010 | 0.01 | 0.90 | 0.01 | — | 5.2 (pD) | $D_2O$ |
| 8 | 0.010 | 0.01 | 0.90 | — | 0.04 | 6.2 (pD) | $D_2O$ |
| 9 | 0.010 | — | 0.90 | — | 0.04 | 6.8 (pD) | $D_2O$ |
| 10 | 0.010 | — | 0.90 | — | 0.04 | 6.4 | $H_2O$ (control) |
| 11 | 0.010 | — | 0.90 | — | 0.08 | 6.4 | $H_2O$ (control) |
| 12 | 0.010 | — | 0.90 | — | 0.04 | 7.2 (pD) | $D_2O$ |
| 13 | 0.010 | — | 0.90 | — | 0.04 | 6.8 | $H_2O$ (control) |

The values are % w/v. The formulations were prepared at 100 mL scale in volumetric glassware and filled into LDPE eye droppers. In some instances, the pD is calculated as pD=0.4+pH*, in which pH* is the measured or observed pH of the solution formulated in a solution containing deuterated water.

Table 23B illustrates analysis time points for the formulations listed in Table 23A.

TABLE 23B

Schedule for atropine sulfate formulation testing

| Storage | Time Point | | |
|---|---|---|---|
| Condition (Horizontal) | Initial (t = 0) | 2 Week | 4 Week |
| 25° C./60% RH | X | X | X |
| 40° C./75% RH |   | X | X |
| 60° C. |   | X | X |

Table 24A and Table 24B illustrate atropine sulfate purity data associated with the atropine sulfate formulations. Purity is indicated as percentage of area under the curve. The ↑ & ↓ indicate the high or low concentration of atropine sulfate monohydrate (0.01% and 0.025%). The A & C indicate the buffer species used, acetic acid and citric acid respectively.

TABLE 24A

Atropine Sulfate Purity as Area-% for $H_2O$ Formulations

| Solvent | Condition | t = 0 | t = 2 weeks | t = 4 weeks |
|---|---|---|---|---|
| Formulation 3 | 25/60 | 98.16 | 98.16 | 98.45 |
| ↓A $H_2O$ pH 4.8 | 40/75 |  | 97.98 | 97.35 |
|  | 60° C. |  | 95.94 | 94.65 |
| Formulation 5 | 25/60 | 98.16 | 97.92 | 97.54 |
| ↓C $H_2O$ pH 5.8 | 40/75 |  | 95.88 | 93.51 |
|  | 60° C. |  | 80.94 | 66.83 |
| Formulation 10 | 25/60 | 98.66 | 96.67 | 95.81 |
| ↓C $H_2O$ pH 6.4 | 40/75 |  | 91.07 | 85.27 |
|  | 60° C. |  | 59.77 | 42.87 |
| Formulation 11 | 25/60 | 99.47 | 97.87 | 96.69 |
| ↓C(2x) $H_2O$ pH 6.4 | 40/75 |  | 90.97 | 84.26 |
|  | 60° C. |  | 54.96 | 34.40 |

TABLE 24A-continued

Atropine Sulfate Purity as Area-% for $H_2O$ Formulations

| Solvent | Condition | t = 0 | t = 2 weeks | t = 4 weeks |
|---|---|---|---|---|
| Formulation 13 | 25/60 | 97.21 | 95.42 | 93.24 |
| ↓C $H_2O$ pH 6.8 | 40/75 |  | 83.05 | 73.00 |
|  | 60° C. |  | 43.99 | 27.50 |

TABLE 24B

Atropine Sulfate Purity as Area-% for $D_2O$ Formulations

| Solvent | Condition | t = 0 | t = 2 weeks | t = 4 weeks |
|---|---|---|---|---|
| Formulation 7 | 25/60 | 98.93 | 99.07 | 98.39 |
| ↓A $D_2O$ pD 5.2 | 40/75 |  | 98.51 | 97.55 |
|  | 60° C. |  | 96.70 | 94.01 |
| Formulation 8 | 25/60 | 98.93 | 98.95 | 98.51 |
| ↓C $D_2O$ pD 6.2 | 40/75 |  | 98.53 | 97.44 |
|  | 60° C. |  | 95.97 | 92.72 |
| Formulation 9 | 25/60 | 99.29 | 98.42 | 98.07 |
| ↓C $D_2O$ pD 6.8 | 40/75 |  | 95.20 | 93.22 |
|  | 60° C. |  | 75.17 | 65.97 |
| Formulation 12 | 25/60 | 98.53 | 97.17 | 95.99 |
| ↓C $D_2O$ pD 7.2 | 40/75 |  | 90.75 | 84.64 |
|  | 60° C. |  | 56.78 | 46.05 |

Table 25A and Table 25B illustrate tropic acid formation associated with the atropine sulfate formulations. Tropic acid is a degradant of atropine sulfate, and is indicated as percentage of area under the curve. LOQ was found to be 0.05% for the RP-HPLC method. The ↑ & ↓ indicate the high or low concentration of atropine sulfate monohydrate (0.01% and 0.025%). The A & C indicate the buffer species used, acetic acid and citric acid, respectively.

TABLE 25A

Tropic Acid as Area-% for $H_2O$ Formulations

| Solvent | Condition | t = 0 | t = 2 weeks | t = 4 weeks |
|---|---|---|---|---|
| Formulation 3 | 25/60 | <LOQ | 0.12 | 0.05 |
| ↓A $H_2O$ pH 4.8 | 40/75 |  | 0.19 | 0.27 |
|  | 60° C. |  | 0.90 | 1.58 |

TABLE 25A-continued

Tropic Acid as Area-% for H₂O Formulations

| Solvent | Condition | t = 0 | t = 2 weeks | t = 4 weeks |
|---|---|---|---|---|
| Formulation 5 | 25/60 | <LOQ | 0.40 | 0.71 |
| ↓C H₂O pH 5.8 | 40/75 | | 2.22 | 4.35 |
| | 60° C. | | 16.62 | 29.13 |
| Formulation 10 | 25/60 | 0.74 | 1.90 | 3.21 |
| ↓C H₂O pH 6.4 | 40/75 | | 7.61 | 13.49 |
| | 60° C. | | 37.44 | 54.06 |
| Formulation 11 | 25/60 | 0.09 | 1.31 | 2.64 |
| ↓C(2x) H₂O pH 6.4 | 40/75 | | 7.61 | 14.68 |
| | 60° C. | | 42.43 | 62.23 |
| Formulation 13 | 25/60 | 2.21 | 3.66 | 6.11 |
| ↓C H₂O pH 6.8 | 40/75 | | 15.47 | 25.80 |
| | 60° C. | | 53.24 | 69.34 |

TABLE 25B

Tropic Acid as Area-% for D₂O Formulations

| Solvent | Condition | t = 0 | t = 2 weeks | t = 4 weeks |
|---|---|---|---|---|
| Formulation 7 | 25/60 | <LOQ | 0.07 | 0.08 |
| ↓A D₂O pD 5.2 | 40/75 | | 0.14 | 0.24 |
| | 60° C. | | 0.71 | 1.07 |
| Formulation 8 | 25/60 | <LOQ | 0.11 | 0.14 |
| ↓C D₂O pD 6.2 | 40/75 | | 0.33 | 0.65 |
| | 60° C. | | 2.32 | 4.03 |
| Formulation 9 | 25/60 | 0.06 | 0.55 | 1.06 |
| ↓C D₂O pD 6.8 | 40/75 | | 3.16 | 6.29 |
| | 60° C. | | 21.09 | 29.25 |
| Formulation 12 | 25/60 | 0.42 | 1.35 | 2.62 |
| ↓C D₂O pD 7.2 | 40/75 | | 7.27 | 13.53 |
| | 60° C. | | 38.58 | 48.15 |

Table 26A and Table 26B illustrate the percentage of potency of atropine in the formulations. The ↑ & ↓ indicate the high or low concentration of atropine sulfate monohydrate (0.01% and 0.025%). The A & C indicate the buffer species used, acetic acid and citric acid respectively.

TABLE 26A

Percentage of potency for H₂O Formulations

| Solvent | Condition | t = 0 | t = 2 weeks | t = 4 weeks |
|---|---|---|---|---|
| Formulation 3 | 25/60 | 106.3 | 108.0 | 109.6 |
| ↓A H₂O pH 4.8 | 40/75 | | 108.1 | 110.0 |
| | 60° C. | | 108.0 | 109.9 |
| Formulation 5 | 25/60 | 105.0 | 105.9 | 107.1 |
| ↓C H₂O pH 5.8 | 40/75 | | 103.8 | 103.5 |
| | 60° C. | | 90.2 | 77.7 |
| Formulation 10 | 25/60 | 101.7 | 100.0 | 98.0 |
| ↓C H₂O pH 6.4 | 40/75 | | 89.4 | 87.0 |
| | 60° C. | | 63.7 | 45.7 |
| Formulation 11 | 25/60 | 97.5 | 96.1 | 94.3 |
| ↓C(2x) H₂O pH 6.4 | 40/75 | | 89.4 | 82.0 |
| | 60° C. | | 55.7 | 35.20 |
| Formulation 13 | 25/60 | 99.4 | 96.9 | 94.1 |
| ↓C H₂O pH 6.8 | 40/75 | | 85.0 | 74.0 |
| | 60° C. | | 46.4 | 29.8 |

TABLE 26B

Percentage of potency for D₂O Formulations

| Solvent | Condition | t = 0 | t = 2 weeks | t = 4 weeks |
|---|---|---|---|---|
| Formulation 7 | 25/60 | 107.3 | 111.3 | 112.9 |
| ↓A D₂O pD 5.2 | 40/75 | | 111.6 | 113.5 |
| | 60° C. | | 111.8 | 113.5 |

TABLE 26B-continued

Percentage of potency for D₂O Formulations

| Solvent | Condition | t = 0 | t = 2 weeks | t = 4 weeks |
|---|---|---|---|---|
| Formulation 8 | 25/60 | 99.0 | 103.0 | 105.0 |
| ↓C D₂O pD 6.2 | 40/75 | | 104.9 | 104.7 |
| | 60° C. | | 101.6 | 103.0 |
| Formulation 9 | 25/60 | 101.4 | 99.9 | 100.1 |
| ↓C D₂O pD 6.8 | 40/75 | | 97.4 | 93.2 |
| | 60° C. | | 78.7 | 68.9 |
| Formulation 12 | 25/60 | 104.9 | 103.5 | 101.6 |
| ↓C D₂O pD 7.2 | 40/75 | | 96.9 | 89.1 |
| | 60° C. | | 62.5 | 50.9 |

Table 27A and Table 27B illustrate the stability of pH or pD for the atropine sulfate formulations. The ↑ & ↓ indicate the high or low concentration of atropine sulfate monohydrate (0.01% and 0.025%). The A & C indicate the buffer species used, acetic acid and citric acid respectively.

TABLE 27A

Stability of pH for H₂O Formulations

| Solvent | Condition | t = 0 | t = 2 weeks | t = 4 weeks |
|---|---|---|---|---|
| Formulation 3 | 25/60 | 4.85 | 4.44 | 4.61 |
| ↓A H₂O pH 4.8 | 40/75 | | 4.41 | 4.54 |
| | 60° C. | | 4.32 | 4.40 |
| Formulation 5 | 25/60 | 5.87 | 5.93 | 6.03 |
| ↓C H₂O pH 5.8 | 40/75 | | 5.96 | 5.96 |
| | 60° C. | | 5.82 | 5.78 |
| Formulation 10 | 25/60 | 6.43 | 6.41 | 6.46 |
| ↓C H₂O pH 6.4 | 40/75 | | 6.62 | 6.67 |
| | 60° C. | | 6.01 | 5.92 |
| Formulation 11 | 25/60 | 6.44 | 6.47 | 6.72 |
| ↓C(2x) H₂O pH 6.4 | 40/75 | | 6.66 | 6.61 |
| | 60° C. | | 6.27 | 6.23 |
| Formulation 13 | 25/60 | 6.77 | 6.91 | 6.91 |
| ↓C H₂O pH 6.8 | 40/75 | | 6.65 | 6.62 |
| | 60° C. | | 6.30 | 6.19 |

TABLE 27B

Stability of pD for D₂O Formulations

| Solvent | Condition | t = 0 | t = 2 weeks | t = 4 weeks |
|---|---|---|---|---|
| Formulation 7 | 25/60 | 5.31 | 5.10 | 5.24 |
| ↓A D₂O pD 5.2 | 40/75 | | 5.08 | 5.15 |
| | 60° C. | | 5.00 | 4.93 |
| Formulation 8 | 25/60 | 6.25 | 5.72 | 5.88 |
| ↓C D₂O pD 6.2 | 40/75 | | 5.74 | 5.78 |
| | 60° C. | | 5.58 | 5.50 |
| Formulation 9 | 25/60 | 6.76 | 6.80 | 6.81 |
| ↓C D₂O pD 6.8 | 40/75 | | 6.78 | 6.86 |
| | 60° C. | | 6.45 | 6.24 |
| Formulation 12 | 25/60 | 7.25 | 7.18 | 7.26 |
| ↓C D₂O pD 7.2 | 40/75 | | 7.14 | 7.15 |
| | 60° C. | | 6.52 | 6.36 |

Example 12. Determination of Shelf Life and Activation Energy for Atropine Sulfate Formulations of Example 11

Figure 10:
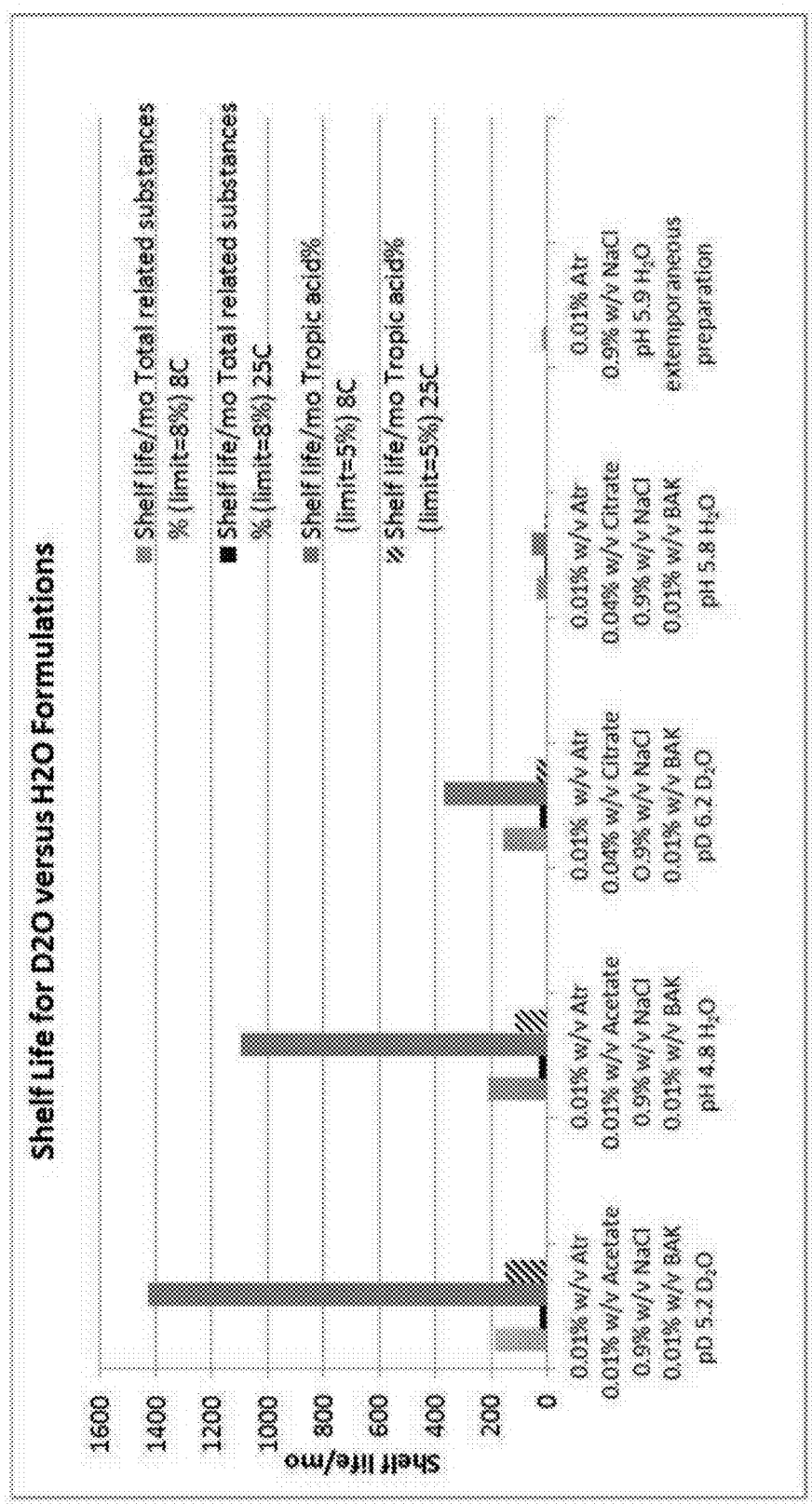
FIG. 10 illustrates estimated shelf lifes for $D_2O$ and $H_2O$ formulations disclosed in Examples 11 and 12.

Activation energy was calculated for the atropine sulfate formulations disclosed in Example 11. Specifically, activation energies were calculated from the total % of related substances (RS) at 40° C. and 60° C. (2 point calculations) and from tropic acid formation at 40° C. and 60° C. (2 point calculations). These values were then averaged. Table 28 illustrates the activation energy calculation. Table 29 illustrates estimated shelf-lifes from the 40° C. rate of formation of % RS and tropic acid, respectively. FIG. 10 illustrates estimated shelf lifes for $D_2O$ and $H_2O$ formulations.

TABLE 28

Activation Energy

| Atropine Formulations | Total RS | Tropic Acid |
|---|---|---|
| 7 | 14 | 19 |
| 3 | 16 | 17 |
| 8 | 20 | 21 |
| 5 | 14 | Poor Corr |
| 6 | 15 | 16 |
| Mean | 16.3 | 18.7 |
| Stdev | 2.68 | 1.90 |
| RSD | 16% | 10% |
| Poor Corr: | One or more curve had $R^2 < 0.95$ | |

TABLE 29

Estimated Shelf Life

| | Estimated Shelf life/mo | | | |
|---|---|---|---|---|
| | Total related substances % (limit = 8%) | | Tropic acid % (limit = 5%) | |
| Formulation | 8° C. | 25° C. | 8° C. | 25° C. |
| 0.01% w/v Atr 0.01% w/v Acetate 0.9% w/v NaCl 0.01% w/v BAK pD 5.2 $D_2O$ (Formulation 7) | 189 | 26 | 1427 | 147 |
| 0.01% w/v Atr 0.01% w/v Acetate 0.9% w/v NaCl 0.01% w/v BAK pH 4.8 $H_2O$ (Formulation 3) | 211 | 29 | 1095 | 113 |
| 0.01% w/v Atr 0.04% w/v Citrate 0.9% w/v NaCl 0.01% w/v BAK pD 6.2 $D_2O$ (Formulation 8) | 158 | 22 | 369.8 | 38 |
| 0.01% w/v Atr 0.04% w/v Citrate 0.9% w/v NaCl 0.01% w/v BAK pH 5.8 $H_2O$ (Formulation 5) | 37 | 5.2 | 54 | 5.5 |
| 0.01% Atr 0.9% w/v NaCl pH 5.9 $H_2O$ extemporaneous preparation | 13.6 | 2.6 | | |

Tables 30 illustrate the predicted shelf life at temperatures of 40° C., 30° C., 25° C., and 2-8° C. for Formulations 2-8 for total RS and tropic acid, respectively.

TABLE 30

Stability Prediction

| | Temperature | RS | | Temperature | Tropic Acid | |
|---|---|---|---|---|---|---|
| Formulation | (° C.) | weeks | months | (° C.) | weeks | months |
| 2 | 40 | 64.5 | 16.1 | 40 | — | — |
| | 30 | 153.2 | 38.3 | 30 | — | — |
| | 25 | 241.2 | 60.3 | 25 | — | — |
| | 2-8 | 1747.9 | 437.0 | 2-8 | — | — |
| 3 | 40 | 31.1 | 7.8 | 40 | 99.5 | 24.9 |
| | 30 | 73.9 | 18.5 | 30 | 268.3 | 67.1 |
| | 25 | 116.3 | 29.1 | 25 | 451.8 | 113.0 |
| | 2-8 | 842.9 | 210.7 | 2-8 | 4382.0 | 1095.5 |
| 4 | 40 | 30.7 | 7.7 | 40 | 42.1 | 10.5 |
| | 30 | 73.0 | 18.2 | 30 | 113.7 | 28.4 |
| | 25 | 114.9 | 28.7 | 25 | 191.5 | 47.9 |
| | 2-8 | 832.6 | 208.1 | 2-8 | 1857.0 | 464.2 |
| 5 | 40 | 5.5 | 1.4 | 40 | 4.9 | 1.2 |
| | 30 | 13.1 | 3.3 | 30 | 13.2 | 3.3 |
| | 25 | 20.6 | 5.2 | 25 | 22.2 | 5.5 |
| | 2-8 | 149.3 | 37.3 | 2-8 | 215.0 | 53.8 |
| 6 | 40 | 10.7 | 2.7 | 40 | 8.8 | 2.2 |
| | 30 | 25.5 | 6.4 | 30 | 23.7 | 5.9 |
| | 25 | 40.1 | 10.0 | 25 | 39.8 | 10.0 |
| | 2-8 | 290.5 | 72.6 | 2-8 | 386.5 | 96.6 |
| 7 | 40 | 27.9 | 7.0 | 40 | 129.6 | 32.4 |
| | 30 | 66.4 | 16.6 | 30 | 349.6 | 87.4 |
| | 25 | 104.5 | 26.1 | 25 | 588.7 | 147.2 |
| | 2-8 | 757.3 | 189.3 | 2-8 | 5709.4 | 1427.4 |
| 8 | 40 | 23.3 | 5.8 | 40 | 33.6 | 8.4 |
| | 30 | 55.3 | 13.8 | 30 | 90.6 | 22.6 |
| | 25 | 87.2 | 21.8 | 25 | 152.5 | 38.1 |
| | 2-8 | 631.6 | 157.9 | 2-8 | 1479.2 | 369.8 |

Example 13—Effect of pH on Ophthalmic Acceptance in Guinea Pigs

A cohort of guinea pigs is administered 50 μL of ophthalmic formulations having different pH values described herein. For example, ophthalmic formulations comprising $H_2O$ or deuterated water (e.g., $D_2O$) are administered to the animals Animal behavior is recorded at predetermined time intervals to evaluate the acceptance of the ophthalmic formulations Example 14—In Vivo Rabbit Eye Irritation Test The exemplary compositions disclosed herein are subjected to rabbit eye irritation test to evalaute their safety profile. The test composition are tested for eye irritation test in New Zealand Rabbits (see for example Abraham M H, et al., *Draize rabbit eye test compatibility with eye irritation thresholds in humans: a quantitative structure-activity relationship analysis*. Toxicol Sci. 2003 December; 76(2):384-91. Epub 2003 Sep. 26; see also Gettings S D et al., *A comparison of low volume, Draize and in vitro eye irritation test data. III. Surfactant-based formulations*. Food Chem Toxicol. 1998 March; 36(3):209-31). The study involves single ocular administration into the right eye and the same volume of its placebo in the left eye of each of the three rabbits. Rabbits are examined immediately and after instillation of the compositions for 4, 24, 48 and 72 hours post instillation to note the signs/symptoms of eye irritation, if any. The test compositions show no sign of irritancy in cornea, iris and conjunctivae of the rabbit eyes.

Example 15—In Vivo Testing of Ophthalmic Aqueous Formulation in Guinea Pigs

Focus deprivation myopia (FDM) is achieved using a latex shield to cover one eye. For defocus-induced myopia, a latex-made facemask was held in place by a rubber-band around the head of animals, leaving both eyes, the nose, mouth and ears freely exposed. A −4.00 D lens is glued onto a plastic lens frame. The lens frame is then attached to the facemask around one eye by a fabric hook-and-loop fastener after the optical center of the lens was aligned with the pupil center. The lens is detached and cleaned on both sides with a water-wetted gauze at least once daily followed by re-attachment to the facemask. All the animals are maintained on a cycle of 12-h illumination (500 Lux) and 12-h darkness during the experimental period A cohort of guinea pigs at age of 3 weeks are randomly assigned to FDM (a facemask worn monocularly) or defocus-induced myopia (a −4.00 D lens worn monocularly) and control groups. The FDM groups were treated with the ophthalmic aqueous formulation, the ophthalmic carrier (without the opthalmic agent), or FDM-only. The defocus-induced myopia groups were treated with the ophthalmic aqueous formulation, the ophthalmic carrier (without the opthalmic agent), or defocus-only. The control groups were treated with the ophthalmic aqueous formulation, the ophthalmic carrier (without the opthalmic agent), or no treatment. Ocular biometric parameters are measured in both eyes of individual animals before and at 11 days of treatment Biometric parameters (e.g. refraction, corneal curvature, and axial components of the eye) are measured by an optometrist, orthoptist, or ophthamologist with help from an animal care assistant during the light cycle (daytime) after removal of the facemask or lens. The optometrist, orthoptist, or ophthamologist is masked in regard to the treatment conditions for each animal.

Refraction is measured by retinoscopy after the pupil is completely dilated by topical administration of 1% cyclopentolate hydrochloride. The results of retinoscopy are recorded as the mean value of the horizontal and vertical meridians.

Corneal curvature is measured with a keratometer modified by attachment of an +8 D lens onto the anterior surface of the keratometer. A group of stainless steel balls with diameters from 5.5 to 11.0 mm are measured by the modified keratometer. Three readings are recorded for each measurement to provide a mean result. The radius of corneal curvature is then deduced from the readings on the balls with known radii.

A-scan ultrasonagraph is used to measure axial components of the eye (lens thickness and vitreous length and axial length). The conducting velocity was 1,723.3 m/s for measurement of the lens thickness and 1,540 m/s for measurement of the vitreous length as described previously. Each of the axial components is calculated as the mean of 10 repeated measurements.

Example 16—Safety and Efficacy Studies of Ophthalmic Aqueous Formulation

A clinical trial is performed to investigate the efficacy and safety of ophthalmic aqueous formulations described herein in patents with myopia. In some instances, the study is open-label, single blind, or double blind study. Patient selection criteria include myopic refraction of at least 1.0D in both eyes, and additional factors such as astigmatism, a documented myopic progression, age, sex, and/or health conditions.

The patients are randomized to receive 0.05%, 0.01%, or 0.001 atropine aqueous formulation formulated in either $H_2O$ or deuterated water (e.g., $D_2O$) once nightly in both eyes. Allocation ratio in some instances is defined based the patient population.

The patients are evaluated on day 0 (baseline), day 14, day 30, and then at 2, 3, 4, 5, 6, 8, 10, 12, 18, 20, 24, and 36 months. At each visit, best-coorected distance log Mar visual acuity (BCVA) is assessed by an optometrist, orthoptist, or ophthamologist using the Early Treatment Diabetic Retinopathy study chart. Near visual acuity is assessed using best-corrected distance spectable correction with a reduced log Mar reading chart placed at 40 cm under well-lit conditions. The near point of accommodation (NPA) is measured using a RAF rule using best-corrected distance spectable correction. Patients are instructed to move the target inwards till the N5 print becomes slightly blurred and then outwards till it just becomes clear. Accommodation amplitude is calculated as the inverse of NPA. Mesopic pupil size is measured with Procyon 3000 pupillometer. Photopic pupil size is measured using the Neuroptics pupillometer.

Cycloplegic autorefraction is determined 30 minutes after 3 drops of cyclopentolate 1% are administered at 5 minutes apart using a Canon RK-F1 autorefractor. A Zeiss IOL Master, a non-contact partial coherence interferometry, is used to measure the ocular axial length.

The primary outcome is myopia progression over the time period of the study. Safety is assessed by adverse events including allergic reactions, irritation, or development of blurring of vision in one or both eyes.

Example 17—Preparation of an Ointment Formulation Containing Atropine Sulfate

Atropine sulfate is mixed with the dispersing agent (e.g., polyethyleneglycol) under heating and sonication and this mixture is further thoroughly mixed with a molten ointment base (e.g., a mixture of wool wax, white petrolatum, and liquid paraffin). The mixture is placed in a pressure vessel, and sterilized at 125° C. for 30-45 minutes and cooled to room temperature. In another embodiment, autoclaving is conducted under nitrogen. The resulting ophthalmic ointment is aseptically filled into pre-sterilized containers (e.g. tubes).

Example 18—Atropine-Mucus Penetrating Particle Composition

A 0.01% atropine-mucus penetrating particle composition was prepared utilizing a milling procedure. An aqueous dispersion containing atropine particles and an MPP-enabling mucus penetrating agent was milled with grinding medium until particle size was reduced to approximately 200 nm with a polydispersity index less than 0.15 as measured by dynamic light scattering. Additional agents such as preservatives are also added during the milling procedure. Subsequently, the atropine-MPP composition are be stored at temperatures of between about 15° C. and about 25° C.

Example 19—Atropine Sulfate-Mucus Penetrating Particle Composition

A 0.01% atropine sulfate-mucus penetrating particle composition was prepared utilizing a milling procedure. An aqueous dispersion containing atropine particles and an MPP-enabling mucus penetrating agent was milled with grinding medium until particle size was reduced to approximately 200 nm with a polydispersity index less than 0.15 as measured by dynamic light scattering. Additional agents such as preservatives are also be added during the milling procedure. Subsequently, the atropine-MPP composition are be stored at temperatures of between about 15° C. and about 25° C.

According to another aspect of the disclosure, described herein is an ophthalmic composition that comprises from about 0.001 wt % to about 0.05 wt % of a muscarinic antagonist and water, at a pH of from about 3.8 to about 7.5.

In some instances, the muscarinic antagonist comprises atropine, atropine sulfate, noratropine, atropine-N-oxide, tropine, tropic acid, hyoscine, scopolomine, tropicamide, cyclopentolate, pirenzapine, homatropine, or a combination thereof. In some cases, the muscarinic antagonist is atropine. In some cases, the muscarinic antagonist is atropine sulfate.

In some instances, the ophthalmic composition comprises one of: at least about 80%, at least about 85%, at least about 90%, at least about 93%, at least about 95%, at least about 97%, at least about 98%, or at least about 99% of the muscarinic antagonist based on initial concentration after extended period of time under storage condition.

In some instances, the ophthalmic composition has a pH of one of: less than about 7.3, less than about 7.2, less than about 7.1, less than about 7, less than about 6.8, less than about 6.5, less than about 6.4, less than about 6.3, less than about 6.2, less than about 6.1, less than about 6, less than about 5.9, less than about 5.8, less than about 5.2, less than about 4.8, or less than about 4.2 after extended period of time under storage condition.

In some instances, the ophthalmic composition further has a potency of one of: at least 80%, at least 85%, at least 90%, at least 93%, at least 95%, at least 97%, at least 98%, or at least 99% after extended period of time under storage condition.

In some instances, the extended period of time is one of: about 1 week, about 2 weeks, about 3 weeks, about 1 month, about 2 months, about 3 months, about 4 months, about 5 months, about 6 months, about 8 months, about 10 months, about 12 months, about 18 months, about 24 months, about 36 months, about 4 years, or about 5 years.

In some instances, the storage condition has a storage temperature of one of: about 25° C., about 40° C., or about 60° C. In some cases, the storage condition has a storage temperature of from about 2° C. to about 10° C. or from about 16° C. to about 26° C. In some cases, the storage condition has a relative humidity of about 60% or about 75%.

In some instances, the ophthalmic composition is in the form of an aqueous solution. In some cases, the muscarinic antagonist is present in the composition at a concentration of one of: from about 0.001 wt % to about 0.04 wt %, from about 0.001 wt % to about 0.03 wt %, from about 0.001 wt % to about 0.025 wt %, from about 0.001 wt % to about 0.02 wt %, from about 0.001 wt % to about 0.01 wt %, from about 0.001 wt % to about 0.008 wt %, or from about 0.001 wt % to about 0.005 wt %.

In some instances, the ophthalmic composition further comprises an osmolarity adjusting agent. In some cases, the osmolarity adjusting agent is sodium chloride.

In some instances, the ophthalmic composition further comprises a preservative. In some cases, the preservative is selected from benzalkonium chloride, cetrimonium, sodium perborate, stabilized oxychloro complex, SofZia, polyquaternium-1, chlorobutanol, edetate disodium, polyhexamethylene biguanide, or combinations thereof.

In some instances, the ophthalmic composition further comprises a buffer agent. In some cases, the buffer agent is selected from borates, borate-polyol complexes, phosphate buffering agents, citrate buffering agents, acetate buffering agents, carbonate buffering agents, organic buffering agents, amino acid buffering agents, or combinations thereof.

In some instances, the ophthalmic composition further comprises a tonicity adjusting agent. In some cases, the tonicity adjusting agent is selected from sodium chloride, sodium nitrate, sodium sulfate, sodium bisulfate, potassium chloride, calcium chloride, magnesium chloride, zinc chloride, potassium acetate, sodium acetate, sodium bicarbonate, sodium carbonate, sodium thiosulfate, magnesium sulfate, disodium hydrogen phosphate, sodium dihydrogen phosphate, potassium dihydrogen phosphate, dextrose, mannitol, sorbitol, dextrose, sucrose, urea, propylene glycol, glycerin, or a combination thereof.

In some instances, the ophthalmic composition is stored in a plastic container. In some cases, the material of the plastic container comprises low-density polyethylene (LDPE).

In some instances, the ophthalmic composition has a dose-to-dose muscarinic antagonist concentration variation of one of: less than 50%, less than 40%, less than 30%, less than 20%, less than 10%, or less than 5%. In some cases, the dose-to-dose muscarinic antagonist concentration variation is based on one of: 10 consecutive doses, 8 consecutive doses, 5 consecutive doses, 3 consecutive doses, or 2 consecutive doses.

In some instances, the ophthalmic composition has a pH of one of: from about 3.8 to about 7.5, from about 4.2 to about 7.5, from about 4.8 to about 7.3, from about 5.2 to about 7.2, from about 5.8 to about 7.1, from about 6.0 to about 7.0, or from about 6.2 to about 6.8.

In some instances, the ophthalmic composition further comprises a pH adjusting agent. In some cases, the pH adjusting agent comprises HCl, NaOH, $CH_3COOH$, or $C_6H_8O_7$.

In some instances, the ophthalmic composition comprises one of: less than 5% of $D_2O$, less than 4% of $D_2O$, less than 3% of $D_2O$, less than 2% of $D_2O$, less than 1% of $D_2O$, less than 0.5% of $D_2O$, less than 0.1% of $D_2O$, or 0% $D_2O$. In some cases, the ophthalmic composition is essentially free of $D_2O$.

In some instances, the ophthalmic composition further comprises a pharmaceutically acceptable carrier.

In some instances, the ophthalmic composition is formulated as an ophthalmic solution for the treatment of an ophthalmic disorder. In some cases, the ophthalmic disorder or condition is pre-myopia, myopia, or progression of myopia.

In some instances, the ophthalmic composition is not formulated as an injectable formulation.

While preferred embodiments of the present disclosure have been shown and described herein, such embodiments are provided by way of example only. Various alternatives to the embodiments described herein are optionally employed in practicing the disclosure. It is intended that the following claims define the scope of the disclosure and that methods and structures within the scope of these claims and their equivalents be covered thereby.

What is claimed is:

1. A method of treating an ophthalmic disorder or condition in an individual in need thereof, comprising: administering to an eye of the individual an effective amount of an ophthalmic composition comprising from about 0.001 wt % to about 0.05 wt % of a muscarinic antagonist and deuterated water, at a pD of from about 4.2 to about 7.9, wherein the muscarinic antagonist is atropine or atropine sulfate, wherein the ophthalmic composition is not administered through injection, and wherein the ophthalmic disorder or condition is pre-myopia, myopia, or progression of myopia.

2. The method of claim 1, wherein administration of the ophthalmic composition arrests or slows down myopia progression.

3. The method of claim 1, wherein the ophthalmic composition has a pD of one of: less than about 7.3, less than about 7.2, less than about 7.1, less than about 7, less than about 6.8, less than about 6.5, less than about 6.4, less than about 6.3, less than about 6.2, less than about 6.1, less than about 6, less than about 5.9, less than about 5.8, less than about 5.2, or less than about 4.8 after extended period of time under storage condition.

4. The method of claim 1, wherein the ophthalmic composition comprises one of: at least about 80%, at least about 85%, at least about 90%, at least about 93%, at least about 95%, at least about 97%, at least about 98%, or at least about 99% of the muscarinic antagonist based on initial concentration after extended period of time under storage condition.

5. The method of claim 1, wherein the ophthalmic composition is stored for an extended period of time comprising one of: about 1 week, about 2 weeks, about 3 weeks, about 1 month, about 2 months, about 3 months, about 4 months, about 5 months, about 6 months, about 8 months, about 10 months, about 12 months, about 18 months, about 24 months, about 36 months, about 4 years, or about 5 years.

6. The method of claim 1, wherein the ophthalmic composition is stored at a storage temperature of from about 2° C. to about 10° C. or from about 16° C. to about 26° C.

7. The method of claim 1, wherein the muscarinic antagonist is present in the composition at a concentration of one of: from about 0.001 wt % to about 0.04 wt %, from about 0.001 wt % to about 0.03 wt %, from about 0.001 wt % to about 0.025 wt %, from about 0.001 wt % to about 0.02 wt %, from about 0.001 wt % to about 0.01 wt %, from about 0.001 wt % to about 0.008 wt %, or from about 0.001 wt % to about 0.005 wt %.

8. The method of claim 1, wherein the ophthalmic composition further comprises an osmolarity adjusting agent.

9. The method of claim 8, wherein the osmolarity adjusting agent is sodium chloride.

10. The method of claim 1, wherein the ophthalmic composition further comprises a preservative.

11. The method of claim 10, wherein the preservative is selected from benzalkonium chloride, cetrimonium, sodium perborate, stabilized oxychloro complex, polyquaternium-1, chlorobutanol, edetate disodium, polyhexamethylene biguanide, or combinations thereof.

12. The method of claim 1, wherein the ophthalmic composition further comprises a buffer agent.

13. The method of claim 12, wherein the buffer agent is selected from borates, borate-polyol complexes, phosphate buffering agents, citrate buffering agents, acetate buffering agents, carbonate buffering agents, organic buffering agents, amino acid buffering agents, or combinations thereof.

14. The method of claim 1, wherein the ophthalmic composition is essentially free of procaine and benactyzine, or pharmaceutically acceptable salts thereof.

15. The method of claim 1, wherein the ophthalmic composition further comprises a pD adjusting agent.

16. The method of claim 15, wherein the pD adjusting agent comprises deuterated hydrochloric acid, deuterated sodium hydroxide, deuterated acetic acid, or deuterated citric acid.

17. The method of claim 1, wherein the ophthalmic composition comprises one of: less than 5% of $H_2O$, less than 4% of $H_2O$, less than 3% of $H_2O$, less than 2% of $H_2O$, less than 1% of $H_2O$, less than 0.5% of $H_2O$, less than 0.1% of $H_2O$, or 0% of $H_2O$.

18. The method of claim 1, wherein the ophthalmic composition is topically administered.

19. The method of claim 1, wherein the ophthalmic composition is administered by instillation.

20. The method of claim 1, wherein the ophthalmic composition is administered through an eye drop bottle containing the ophthalmic composition.

* * * * *